United States Patent
Girijavallabhan et al.

(10) Patent No.: US 9,457,039 B2
(45) Date of Patent: Oct. 4, 2016

(54) 2'-DISUBSTITUTED NUCLEOSIDE DERIVATIVES AND METHODS OF USE THEREOF FOR THE TREATMENT OF VIRAL DISEASES

(71) Applicant: Merck Sharp & Dohme Corp., Rahway, NJ (US)

(72) Inventors: Vinay Girijavallabhan, Whippany, NJ (US); Stephane Bogen, Somerset, NJ (US); Weidong Pan, Hillsborough, NJ (US); Qun Dang, Westfield, NJ (US); Ian Davies, Princeton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/436,687

(22) PCT Filed: Oct. 11, 2013

(86) PCT No.: PCT/CN2013/085069
§ 371 (c)(1),
(2) Date: Apr. 17, 2015

(87) PCT Pub. No.: WO2014/059902
PCT Pub. Date: Apr. 24, 2014

(65) Prior Publication Data
US 2016/0045526 A1  Feb. 18, 2016

Related U.S. Application Data

(60) Provisional application No. 61/715,017, filed on Oct. 17, 2012.

(51) Int. Cl.
| | | |
|---|---|---|
| *C07H 19/12* | (2006.01) | |
| *C07H 19/23* | (2006.01) | |
| *C07D 487/04* | (2006.01) | |
| *A61K 31/706* | (2006.01) | |
| *A61K 31/53* | (2006.01) | |
| *A61P 31/14* | (2006.01) | |
| *A61K 45/06* | (2006.01) | |
| *A61K 31/7056* | (2006.01) | |
| *A61K 38/21* | (2006.01) | |
| *C07H 7/06* | (2006.01) | |

(52) U.S. Cl.
CPC ......... *A61K 31/706* (2013.01); *A61K 31/7056* (2013.01); *A61K 38/21* (2013.01); *A61K 45/06* (2013.01); *C07D 487/04* (2013.01); *C07H 7/06* (2013.01)

(58) Field of Classification Search
CPC ... C07H 19/12; C07H 19/23; A61K 31/7052
USPC .............. 536/27.1, 28.1; 514/43, 52
See application file for complete search history.

(56) References Cited

U.S. PATENT DOCUMENTS

| 7,879,815 B2 | 2/2011 | MacCoss et al. |
| 7,973,013 B2 | 7/2011 | Cho et al. |
| 8,492,539 B2 | 7/2013 | Chun et al. |
| 9,156,872 B2 * | 10/2015 | Girijavallabhan ..... C07H 19/10 |
| 2009/0081636 A1 | 3/2009 | Huang |
| 2010/0081628 A1 | 4/2010 | Du et al. |
| 2011/0230654 A1 | 9/2011 | Butler et al. |

FOREIGN PATENT DOCUMENTS

| CN | 101437524 | 5/2009 |
| CN | 102596958 | 7/2012 |
| CN | 102596979 | 7/2012 |
| WO | WO02057287 | 7/2002 |
| WO | WO2005003147 | 1/2005 |
| WO | WO2006031725 | 3/2006 |
| WO | WO2008082484 | 7/2008 |
| WO | WO2008082488 | 7/2008 |
| WO | WO2008082602 | 7/2008 |
| WO | WO2008083351 | 7/2008 |

(Continued)

OTHER PUBLICATIONS

Asselah et al., Protease and polymerase inhibitors for the treatmentof hepatitis C, Liver International, 2009, 57-67, 29(s1).
Balsano, Recent Advances in Antiviral Agents: Established and Innovative Therapies for Viral Hepatitis, Mini-Reviews in Medicinal Chemistry, 2008, pp. 307-318, 8(4).

(Continued)

*Primary Examiner* — Venkataraman Balasubramanian
(74) *Attorney, Agent, or Firm* — Alysia A. Finnegan; Gloria Fuentes

(57) ABSTRACT

2'-disubstituted substituted nucleoside derivatives of formula (I) and pharmaceutically acceptable salts thereof are disclosed: (1), wherein A is $N^3$ or $NH_2$ and X, Y, $R^1$, $R^2$, $R^3$, $R^4$, $R^5$ and $R^{18}$ are as defined herein. Compositions comprising at least one 2'-disubstituted nucleoside derivative, and methods of using the 2'-disubstituted nucleoside derivatives for treating or preventing HCV infection in a patient are disclosed.

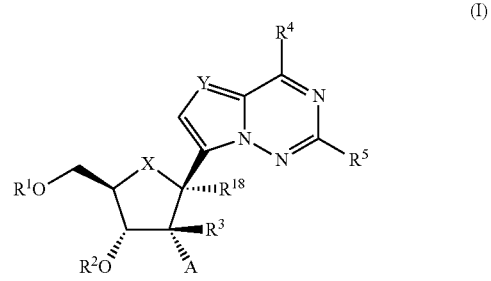

(I)

16 Claims, No Drawings

(56) References Cited

FOREIGN PATENT DOCUMENTS

| WO | WO2008136815 | 11/2008 |
| WO | WO2009032116 | 3/2009 |
| WO | WO2009032123 | 3/2009 |
| WO | WO2009032124 | 3/2009 |
| WO | WO2009032125 | 3/2009 |
| WO | WO2009132123 | 10/2009 |
| WO | WO2010002877 | 1/2010 |
| WO | WO2010075517 | 7/2010 |
| WO | WO2010075549 | 7/2010 |
| WO | WO2010111483 | 9/2010 |
| WO | WO2011035231 | 3/2011 |
| WO | WO2011035250 | 3/2011 |
| WO | WO2011150288 | 12/2011 |
| WO | WO2011150356 | 12/2011 |
| WO | WO2012142075 | 10/2012 |
| WO | WO2012142093 | 10/2012 |
| WO | WO2014059901 | 4/2014 |

OTHER PUBLICATIONS

Beaulieu et al., Inhibitors of the HCV NS5B polymerase: New hope for the treatment of hepatitis C infections, Current Opinions in Investigational Drugs, 2004, 838, 5.

Bobeck et al., Advances in nucleoside monophosphate prodrugs as anti-HCV agents, Antiviral Therapy, 2010, 935-950, 15.

Chatel-Chaix et al., Direct-acting and host-targeting HCV inhibitors: current and future directions, Current Opinion in Virology, 2012, 588-598, 2.

Dore et al., The changing therapeutic landscape for hepatitis C, Med. J. Australia, 2012, 629-632, 196.

Dudfield et al., Synthesis of C-ribosyl imidazo[2,1-f][1,2,4]triazines as inhibitors of adenosine and AMP deaminases, Journal of the Chemical Society, Perkin Transactions 1, 1999, 2929-2936, 20.

Eldrup et al., Structure-Activity Relationship of Purine Ribonucleosides for Inhibition of Hepatitis C Virus RNA-Dependent RNA Polymerase, J. Med. Chem., 2004, 2283-2295, 47.

Furman et al., Nucleoside analog inhibitors of hepatitis C viral replication: recent advances, challenges and trends, Future Medicinal Chemistry, 2009, 1429-1452, 1.

Holland et al., Hepatitis C genotyping by direct sequencing of the product from the Roche amplicor test: Methodology and application to a South Australian population, Pathology, 1998, 192-195, 30.

Ishii et al., Expression of Hepatitis C Virus NS5B Protein: Characterization of Its RNA Polymerase Activity and RNA Binding, Hepatology, 1999, 1227-1235, 29.

Lohmann et al., Biochemical and Kinetic Analyses of NS5B RNA-Dependent RNA Polymerase of the Hepatitis C Virus, Virology, 1998, 108-118, 249.

Malcolm et al., SCH 503034, a Mechanism-Based Inhibitor of Hepatitis C Virus NS3 Protease, Suppresses Polyprotein Maturation and Enhances the Antiviral Activity of Alpha Interferon in Replicon Cells, Antimicrobial Agents and Chemotherapy, 2006, 1013-1020, 50.

Mehellou, Phosphoramidate Prodrugs Deliver with Potency Against Hepatitis C Virus, ChemMedChem, 2010, 1841-1842, 5.

Ni et al., Progress and Development of Small Molecule HCV Antivirals, Current Opinion in Drug Discovery and Development, 2004, 446, 7(4).

Ott et al., 2,7-Disubstituted-pyrrolo[2,1-f][1,2,4]triazines: New Variant of an Old Template and Application to the Discovery of Anaplastic Lymphoma Kinase (ALK) Inhibitors with in Vivo Antitumor Activity, Journal of Medicinal Chemistry, 2011, 6328-41, 54.

Poordad et al., Treating hepatitis C: current standard of care and emerging direct-acting antiviral agents, Journal of Viral Hepatitis, 2012, 449-464, 19.

Simmonds et al., Classification of hepatitis C virus into six major genotypes and a series of, J. Gen Virol, 1993, 2391-2399, 74(Pt11).

Tan et al., Hepatitis C Therapeutics: Current Status and Emerging Strategies, Nature Reviews, 2002, 867-881, 1.

\* cited by examiner

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: oligonucleotide primer

<400> SEQUENCE: 1
atggacaggc gccctga                                                  17

<210> SEQ ID NO 2
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 2
ttgatgggca gcttggtttc                                               20
```

```
<210> SEQ ID NO 3
<211> LENGTH: 17
<212> TYPE: DNA
<213> ORGANISM: Artificial Sequence
<220> FEATURE:
<223> OTHER INFORMATION: oligonucleotide probe

<400> SEQUENCE: 3
cacgccatgc gctgcgg                                                    17
```

2'-DISUBSTITUTED NUCLEOSIDE DERIVATIVES AND METHODS OF USE THEREOF FOR THE TREATMENT OF VIRAL DISEASES

CROSS-REFERENCE TO RELATED APPLICATIONS

This application is a §371 National Stage Application of PCT/CN2013/085069, international filing date of Oct. 11, 2013, which claims the benefit of U.S. Provisional Application No. 61/715,017, filed Oct. 17, 2012, the contents of which are hereby incorporated by reference in their entirety.

FIELD OF THE INVENTION

The present invention relates to 2'-Disubstituted Nucleoside Derivatives, compositions comprising at least one 2'-Disubstituted Nucleoside Derivative, and methods of using the 2'-Disubstituted Nucleoside Derivatives for treating or preventing HCV infection in a patient.

REFERENCE TO SEQUENCE LISTING SUBMITTED ELECTRONICALLY

The sequence listing of the present application is submitted electronically via EFS-Web as an ASCII formatted sequence listing with a file name "23337USPCT-SEQLIST-17APR2015.TXT", creation date of Mar. 6, 2015, and a size of 4.00 KB. This sequence listing submitted via EFS-Web is part of the specification and is herein incorporated by reference in its entirety.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are over 3 million chronically infected people in the United States alone, according to the U.S. Center for Disease Control. About 150 million individuals are chronically infected worldwide, with at least 3 to 4 million people being infected each year. Hepatitis C Fact Sheet, World Health Organization, July 2012. Once infected, about 20% of people clear the virus, but the rest harbor HCV the rest of their lives. Ten to twenty percent of chronically infected individuals eventually develop liver-destroying cirrhosis or cancer. HCV is transmitted parenterally by contaminated blood and blood products, contaminated needles, or sexually and vertically from infected mothers or carrier mothers to their off-spring.

Different approaches to HCV therapy have been taken, which include the inhibition of viral serine proteinase (NS3 protease), helicase, and RNA-dependent RNA polymerase (NS5B), and the development of a vaccine. Current and investigational treatments for HCV infection are reviewed in Poordad et al., Treating hepatitis C: current standard of care and emerging direct-acting antiviral agents. *Journal of Viral Hepatitis* 19: 449-464 (2012); Asselah et al., Protease and polymerase inhibitors for the treatment of hepatitis C. *Liver International* 29(s1): 57-67 (2009); G. J. Dore. The changing therapeutic landscape for hepatitis C. *Med. J. Australia* 196: 629-632 (2012); and Balsano, *Mini Rev. Med. Chem.* 8(4): 307-318, 2008. Despite the availability of therapeutic treatment options, chronic HCV infection remains a major healthcare concern. Moreover, there is no established vaccine for HCV. Consequently, there is a need for improved therapeutic agents that effectively combat chronic HCV infection.

The HCV virion is an enveloped positive-strand RNA virus with a single oligoribonucleotide genomic sequence of about 9400 bases which encodes a polyprotein of about 3,000 amino acids. The protein products of the HCV gene consist of the structural proteins C, E1, and E2, and the non-structural proteins NS2, NS3, NS4A, NS4B, NS5A and NS5B. The nonstructural (NS) proteins are believed to provide the catalytic machinery for viral replication.

The NS3 protease releases NS5B, the RNA-dependent RNA polymerase from the polyprotein chain. HCV NS5B polymerase is required for the synthesis of a negative-strand RNA intermediate from a positive-strand genomic viral RNA that serves as a template in the replication cycle of HCV. NS5B polymerase is an essential component in the HCV replication complex. See K. Ishi, et al., "Expression of Hepatitis C Virus NS5B Protein: Characterization of Its RNA Polymerase Activity and RNA Binding," *Hepatology*, 29:1227-1235 (1999) and V. Lohmann, et al., "Biochemical and Kinetic Analyses of NS5B RNA-Dependent RNA Polymerase of the Hepatitis C Virus," *Virology*, 249: 108-118 (1998). Inhibition of HCV NS5B polymerase prevents formation of the double-stranded HCV RNA and therefore constitutes an attractive approach to the development of HCV-specific antiviral therapies.

The development of inhibitors of HCV NS5B polymerase with potential for the treatment of HCV infection has been reviewed in Poordad et al. (2012), supra; Asselah et al. (2009), supra; and Chatel-Chaix et al. Direct-acting and host-targeting HCV inhibitors: current and future directions. *Current Opinion in Virology*, 2:588-598 (2012). The activity of purine ribonucleosides against HCV polymerase was reported by A. E. Eldrup et al., "Structure-Activity Relationship of Purine Ribonucleosides for Inhibition of HCV RNA-Dependent RNA Polymerase," *J. Med. Chem.*, 47:2283-2295 (2004). Nucleoside analogs said to be useful in the treatment of hepatitis C are disclosed in WO 2011/035231, WO 2005/003147, WO 2010/0081628, U.S. Pat. No. 7,879,815, WO 2010/075517, WO 2010/002877, and WO 2009/132123.

SUMMARY OF THE INVENTION

In one aspect, the present invention provides Compounds of Formula (I):

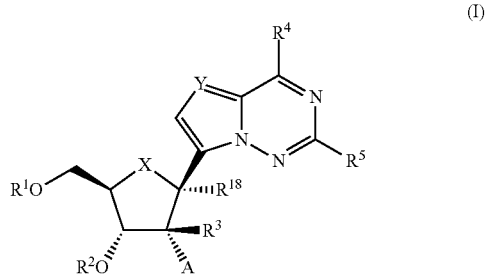

or a pharmaceutically acceptable salt thereof,
wherein:
A is —NH$_2$ or —N$_3$;
X is O, N, S or CH$_2$;
Y is N or —C(R$^6$)—;
R$^1$ is H,

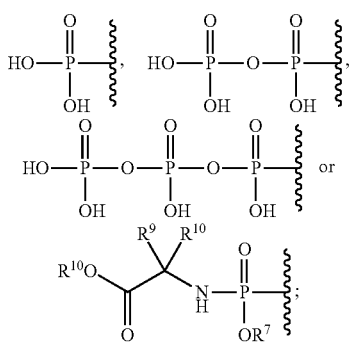

$R^2$ is H, —C(O)—($C_1$-$C_6$ alkyl) or

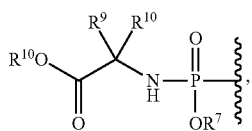

or $R^1$ and $R^2$ join to form a group having the formula:

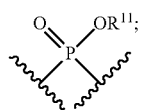

$R^3$ is $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl or $C_3$-$C_7$ cycloalkyl;

$R^4$ and $R^5$ are each independently selected from H, —$OR^{12}$, —$NHC(O)OR^{12}$, —$NHC(O)N(R^{12})_2$, —$N(R^{12})_2$ and —$NHC(O)R^{12}$;

$R^6$ is H, $C_1$-$C_6$ alkyl, $C_1$-$C_6$ haloalkyl, $C_1$-$C_6$ hydroxyalkyl, halo, —$OR^{12}$, —$SR^{12}$, —$N(R^{12})_2$, $C_3$-$C_7$ cycloalkyl, $C_6$-$C_{10}$ aryl, 5- or 6-membered monocyclic heteroaryl or 9- or 10-membered bicyclic heteroaryl;

$R^7$ is H, $C_6$-$C_{10}$ aryl, 5- or 6-membered monocyclic heteroaryl, 9- or 10-membered bicyclic heteroaryl, or —($C_1$-$C_3$ alkylene)-C(O)O—($C_1$-$C_6$ alkyl), wherein said $C_6$-$C_{10}$ aryl group, said 5- or 6-membered monocyclic heteroaryl group and said 9- or 10-membered bicyclic heteroaryl group can be optionally substituted with $R^{13}$, $R^8$ is H, $C_1$-$C_6$ alkyl, $C_3$-$C_7$ cycloalkyl, phenyl or benzyl, wherein said $C_1$-$C_6$ alkyl can be optionally substituted with a group selected from halo, —$OR^{12}$, —$SR^{12}$, guanidino, —$N(R^{12})_2$, —$C(O)OR^{12}$, —$C(O)N(R^{12})_2$, —$NHC(O)R^{12}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —$OR^{12}$;

$R^9$ is H, $C_1$-$C_6$ alkyl, $C_3$-$C_7$ cycloalkyl, phenyl or benzyl, wherein said $C_1$-$C_6$ alkyl can be optionally substituted with a group selected from halo, —$OR^{12}$, —$SR^{12}$, guanidino, —$N(R^{12})_2$, —$C(O)OR^{12}$, —$C(O)N(R^{12})_2$, —$NHC(O)R^{12}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —$OR^{12}$;

$R^{10}$ is H, $C_1$-$C_{20}$ alkyl, $C_2$-$C_{20}$ alkenyl, —($C_1$-$C_3$ alkylene)$_m$-($C_3$-$C_7$ cycloalkyl), —($C_1$-$C_3$ alkylene)$_m$-($C_6$-$C_{10}$ aryl) or —($C_1$-$C_3$ alkylene)$_m$-adamantyl, wherein said $C_1$-$C_{20}$ alkyl group, said $C_2$-$C_{20}$ alkenyl group, said $C_6$-$C_{10}$ aryl group and said adamantyl group can be optionally substituted with up to three groups, each independently selected from halo, —$OR^{12}$, —$C(O)OR^{12}$, CN, $NO_2$, $C_1$-$C_6$ haloalkyl, $C_1$-$C_6$ hydroxyalkyl, $C_3$-$C_7$ cycloalkyl, $C_6$-$C_{10}$ aryl, 5- or 6-membered monocyclic heteroaryl, 9- or 10-membered bicyclic heteroaryl, —$N(R^{12})_2$, —$C(O)N(R^{12})_2$—$SR^{12}$, —$S(O)R^{12}$, —$S(O)_2R^{12}$, —$S(O)_2N(R^{12})_2$, —$NHC(O)R^{12}$, —$NHC(O)OR^{12}$ and —$NHC(O)N(R^{12})_2$;

$R^{11}$ is H, $C_1$-$C_{20}$ alkyl, $C_2$-$C_{20}$ alkenyl, —($C_1$-$C_3$ alkylene)$_m$-($C_3$-$C_7$ cycloalkyl), $C_3$-$C_7$ cycloalkyl, —($C_1$-$C_3$ alkylene)$_m$-$C_6$-$C_{10}$ aryl or —($C_1$-$C_3$ alkylene)$_m$-adamantyl, 5- or 6-membered monocyclic heteroaryl, 9- or 10-membered bicyclic heteroaryl, wherein said $C_1$-$C_{20}$ alkyl group, said $C_2$-$C_{20}$ alkenyl group, said $C_6$-$C_{10}$ aryl group, said adamantyl group, said 5- or 6-membered monocyclic heteroaryl group and said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5- or 6-membered monocyclic heteroaryl, 9- or 10-membered bicyclic heteroaryl, halo, —$OR^{12}$, —$SR^{12}$, —$S(O)R^{12}$, —$S(O)_2R^{12}$, —$S(O)_2N(R^{12})_2$, $C_1$-$C_6$ haloalkyl, $C_1$-$C_6$ hydroxyalkyl, —O—($C_1$-$C_6$ haloalkyl), —CN, —$NO_2$, —$N(R^{12})_2$, —$C(O)OR^{12}$, —$C(O)N(R^{12})_2$ and —$NHC(O)R^{12}$, —$NHC(O)OR^{12}$ and —$NHC(O)N(R^{12})_2$;

each occurrence of $R^{12}$ is independently H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -5- or 6-membered monocyclic heteroaryl group or said 9- or 10-membered bicyclic heteroaryl group can be optionally substituted with $R^{16}$;

$R^{13}$ represents from one to five substituent groups, each independently selected from $C_1$-$C_6$ alkyl, halo, —$OR^{12}$, —$SR^{12}$, $C_1$-$C_6$ haloalkyl, $C_1$-$C_6$ hydroxyalkyl, —O—($C_1$-$C_6$ haloalkyl), —CN, —$NO_2$, —$N(R^{12})_2$, —$C(O)OR^{12}$, —$C(O)N(R^{12})_2$ and —$NHC(O)R^{12}$, or any two $R^{13}$ groups on adjacent ring carbon atoms can combine to form —O—$R^{14}$—O—;

$R^{14}$ is $[C(R^{15})_2]_n$—;

each occurrence of $R^{15}$ is independently H or $C_1$-$C_6$ alkyl;

$R^{16}$ represents from one to five substituent groups, each independently selected from $C_1$-$C_6$ alkyl, $C_2$-$C_6$ alkenyl, $C_2$-$C_6$ alkynyl, halo, —$OR^{17}$, —$SR^{17}$, $C_1$-$C_6$ haloalkyl, $C_1$-$C_6$ hydroxyalkyl, —O—($C_1$-$C_6$ haloalkyl), —CN, —$NO_2$, —$N(R^{17})_2$, —$C(O)OR^{17}$, —$C(O)N(R^{17})_2$ and —$NHC(O)R^{17}$;

each occurrence of $R^{17}$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl);

$R^{18}$ is H, $C_1$-$C_6$ alkyl, —O($C_1$-$C_6$ alkyl), $C_1$-$C_6$ alkynyl, $C_1$-$C_6$ alkenyl, or CN; and each occurrence of m is independently 0 or 1, and each occurrence of n is independently 1, 2, or 3.

The Compounds of Formula (I) (also referred to herein as the "2'-Disubstituted Nucleoside Derivatives") and pharmaceutically acceptable salts thereof can be useful, for example, for inhibiting HCV viral replication or replicon activity, and for treating or preventing HCV infection in a patient. Without being bound by any specific theory, it is believed that the 2'-Disubstituted Nucleoside Derivatives inhibit HCV viral replication by inhibiting HCV NS5B.

Accordingly, the present invention provides methods for treating or preventing HCV infection in a patient, comprising administering to the patient an effective amount of at least one 2'-Disubstituted Nucleoside Derivative.

The details of the invention are set forth in the accompanying detailed description set forth below.

Other embodiments, aspects and features of the present invention are either further described in or will be apparent from the ensuing description, examples and appended claims.

DETAILED DESCRIPTION OF THE INVENTION

The present invention relates to 2'-Disubstituted Nucleoside Derivatives, compositions comprising at least one 2'-Disubstituted Nucleoside Derivative, and methods of using the 2'-Disubstituted Nucleoside Derivatives for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of 2'-Disubstituted Nucleoside Derivative and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood or severity of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)— cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)— alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH$ (CH₃)CH₂—. In one embodiment, an alkylene group has from 1 to about 6 carbon atoms. In another embodiment, an alkylene group is branched. In another embodiment, an alkylene group is linear. In one embodiment, an alkylene group is —CH₂—. The term "$C_1$-$C_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

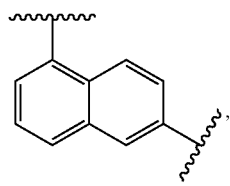 [SMILES: *c1ccc2c(*)cccc2c1]

is understood to represent both:

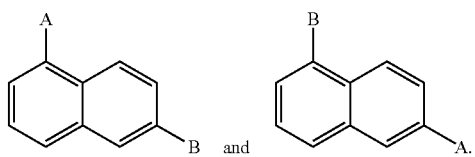

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

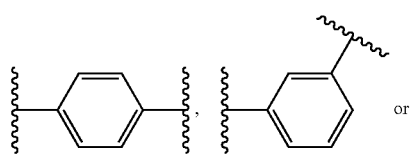

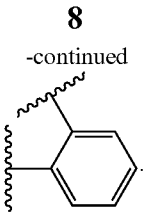

Unless otherwise indicated, an arylene group is unsubstituted.

The term "cycloalkyl," as used herein, refers to a non-aromatic mono- or multicyclic ring system comprising from 3 to about 10 ring carbon atoms. In one embodiment, a cycloalkyl contains from about 5 to about 10 ring carbon atoms. In another embodiment, a cycloalkyl contains from 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

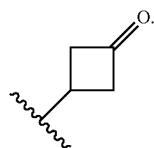 [SMILES: *C1CC(=O)C1]

The term "halo," as used herein, means —F, —Cl, —Br or —I.

The term "haloalkyl," as used herein, refers to an alkyl group as defined above, wherein one or more of the alkyl group's hydrogen atoms have been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH₂F, —CHF, —CF₃, —CH₂Cl and —CCl₃. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH₂OH, —CH₂CH₂OH, —CH₂CH₂CH₂OH and —CH₂CH(OH)CH₃. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

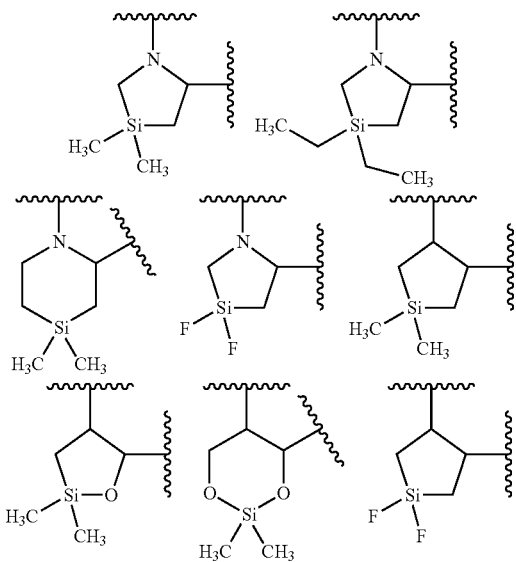

A ring carbon atom of a heterocycloalkyl group may be functionalized as a carbonyl group. An illustrative example of such a heterocycloalkyl group is:

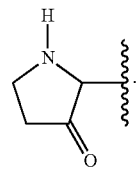

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "ring system substituent," as used herein, refers to a substituent group attached to an aromatic or non-aromatic ring system which, for example, replaces an available hydrogen on the ring system. Ring system substituents may be the same or different, and are each independently selected. Examples of ring system substituents include alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S- alkyl, —S-aryl, —S-heteroaryl, —S-alkylene-aryl, —S—alkylene-heteroaryl, —S(O)₂-alkylene-aryl, —S(O)₂-alkylene-heteroaryl, —Si(alkyl)₂, —Si(aryl)₂, —Si(heteroaryl)₂, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH₂, —C(=NH)—NH₂, —C(=NH)—NH(alkyl), —N(Y₁)(Y₂), -alkylene-N(Y₁)(Y₂), —C(O)N(Y₁)(Y₂) and —S(O)₂N(Y₁)(Y₂), wherein Y₁ and Y₂ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH₃)₂— and the like which form moieties such as, for example:

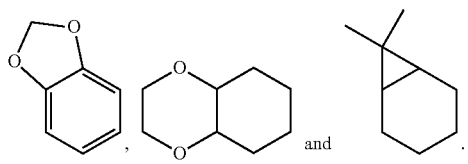

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^6$, $R^a$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a 2'-Disubstituted Nucleoside Derivative or a pharmaceutically acceptable salt of the compound. The transformation may occur by various mechanisms (e.g., by metabolic or chemical processes), such as, for example, through hydrolysis in blood.

For example, if a 2'-Disubstituted Nucleoside Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylamino-ethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a 2'-Disubstituted Nucleoside Derivative contains an alcohol functional group, a prodrug can be formed by the replacement of one or more of the hydrogen atoms of the alcohol groups with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$) alkoxycarbonyloxymethyl, N—($C_1$-$C_6$)alkoxycarbonylaminomethyl, succinoyl, ($C_1$-$C_6$)alkanoyl, α-amino($C_1$-$C_4$) alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate). Other non-limiting example of alcohol-derived prodrugs include —P(O)(OH)₂; —P(O)(—O—$C_1$-$C_6$alkyl)₂; —P(O)(—NH-(α-aminoacyl group))(-O-aryl); —P(O)(—O—($C_1$-$C_6$ alkylene)-S-acyl)(-NH-arylalkyl); any cyclic phosphate ester that forms a bridge between two ribose hydroxyl groups, such as:

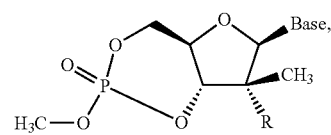

wherein the cyclic phosphate ester forms a bridge between the 3'-OH group and 5'-OH groups; and those described in U.S. Pat. No. 7,879,815; International Publication Nos. WO2005/003047, WO2008/082602, WO2010/0081628, WO2010/075517 and WO2010/075549; Mehellou, *Chem. Med. Chem.*, 5:1841-1842 (2005); Bobeck et al., *Antiviral Therapy* 15:935-950 (2010); Furman et al., Future Medicinal Chemistry, 1:1429-1452 (2009); and Erion, *Microsomes and Drug Oxidations, Proceedings of the International Symposium*, 17th, Saratoga Springs, N.Y., United States, Jul. 6-10, 2008, 7-12 (2008).

If a 2'-Disubstituted Nucleoside Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$ alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino$(C_1-C_4)$alkyl or mono-N— or di-N,N—$(C_1-C_6)$alkylaminoalkyl; —C(Y$^4$)Y$^5$ wherein Y$^4$ is H or methyl and Y$^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—$(C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The 2'-Disubstituted Nucleoside Derivatives can form salts which are also within the scope of this invention. Reference to a 2'-Disubstituted Nucleoside Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a 2'-Disubstituted Nucleoside Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a 2'-Disubstituted Nucleoside Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the 2'-Disubstituted Nucleoside Derivatives may be atropisomers (e.g., substituted biaryls) and are considered as part of this invention. Enantiomers can also be directly separated using chiral chromatographic techniques.

It is also possible that the 2'-Disubstituted Nucleoside Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a 2'-Disubstituted Nucleoside Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the 2'-Disubstituted Nucleoside Derivatives, and of the salts, solvates, hydrates, esters and prodrugs of the 2'-Disubstituted Nucleoside Derivatives, are intended to be included in the present invention.

In some instances, the compounds of the present invention are designated as "isomer 1" and "isomer 2." This designation refers to stereoisomers at the chiral phosphorus atom of the 5'-prodrug moiety as illustrated below for cyclic and non-cyclic prodrugs, wherein the structure:

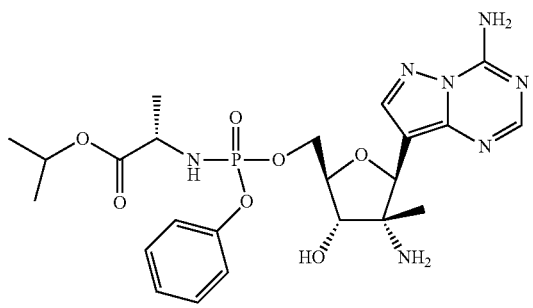 [SMILES: CC(C)OC(=O)[C@H](C)NP(=O)(OC[C@H]1O[C@@H](c2cnn3c(N)ncnc23)[C@](C)(N)[C@@H]1O)Oc1ccccc1]

is understood to represent the following two phosphorus stereoisomers:

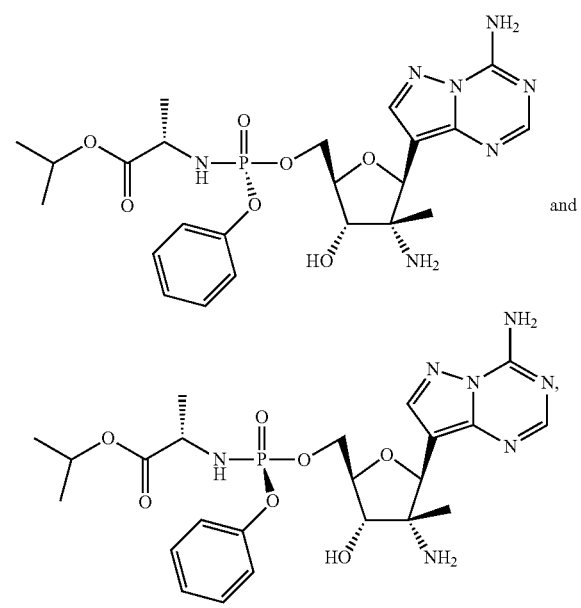

and the structure:

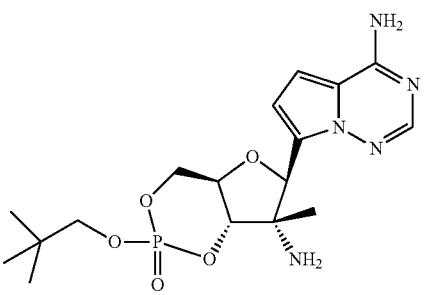

is understood to represent the following two phosphorus stereoisomers:

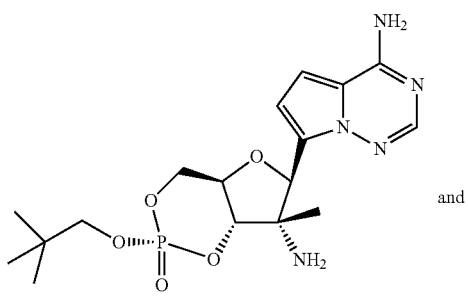

and

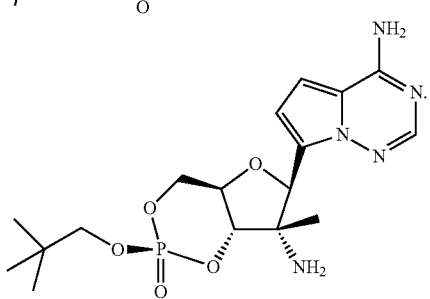

The terms "isomer 1" and "isomer 2" can be assigned to isomers of known absolute configuration or can be used to describe stereoisomers of unknown absolute configuration. Thus, the use of the terms "isomer 1" and "isomer 2" is not to be interpreted as indicating that the absolute configuration of both isomers is known.

The following abbreviations are used below and have the following meanings: Ac is acetyl or —C(O)CH$_3$, Ac$_2$O is acetic anhydride; Bu is butyl; t-BuMgCl is tert-butyl magnesium chloride; DCM is dichloromethane; Dess-Martin Periodinane is 1,1,1-triacetoxy-1,1-dihydro-1,2-benziodoxol-3(1H)-one; DIBAL-H is diisobutylaluminum hydride; DMAP is N,N-dimethylamino pyridine; Et$_3$N (alternatively NEt$_3$) is triethylamine; EtOAc is ethyl acetate; EtOH is ethanol; HPLC is high performance liquid chromatography; KHMDS is potassium hexamethyldisilazide; KOBut is potassium tert-butoxide; LCMS is liquid chromatography/mass spectrometry; LDA is lithium diisopropylamide; MeOH is methanol; NMI is N-methylimidazole; Pd(OH)$_2$ is palladium hydroxide; TBAF is tetra n-butylammonium fluoride; TEA is triethylamine; THF is tetrahydrofuran; TIPDSiCl$_2$ is 1,3-dichloro-1,1,3,3-tetraisopropyldisiloxane; TLC is thin-layer chromatography; and TMSCN is trimethylsilyl cyanide.

The Compounds of Formula (I):

The present invention provides 2'-Disubstituted Nucleoside Derivatives of Formula (I):

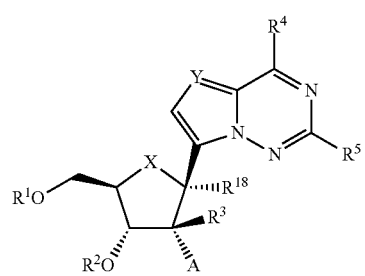

(I)

and pharmaceutically acceptable salts thereof, wherein A, X, Y, R$^1$, R$^2$, R$^3$, R$^4$, R$^5$, and R$^{18}$ are defined above for the Compounds of Formula (I).

In one embodiment, A is N$_3$.
In another embodiment A is NH$_2$.
In one embodiment, X is O.
In another embodiment, X is N.
In another embodiment, X is S.
In another embodiment, X is CH$_2$.
In another embodiment, Y is —C(R$^6$)—.
In one embodiment, R$^1$ is

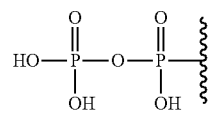

In another embodiment, R$^1$ is

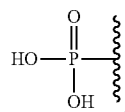

In another embodiment, R$^2$ is —C(O)—(C$_1$-C$_6$ alkyl).
In yet another embodiment, R$^2$ is —C(O)—CH(CH$_3$)$_2$.
In another embodiment, R$^2$ is:

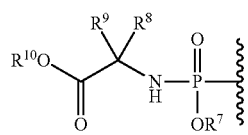

In one embodiment, R$^3$ is H.
In another embodiment, R$^3$ is C$_1$-C$_6$ haloalkyl.
In yet another embodiment, R$^3$ is C$_1$-C$_6$ hydroxyalkyl.
In an additional embodiment, R$^3$ is C$_2$-C$_6$ alkynyl.
In another embodiment R$^3$ is C$_3$-C$_7$ cycloalkyl.
In another embodiment, R$^3$ is C$_1$-C$_6$ alkyl.
In yet another embodiment, R$^3$ is methyl.
In another embodiment, R$^3$ is C$_2$-C$_6$ alkenyl.
In another embodiment, R$^4$ is —OR$^{12}$.
In another embodiment, R$^4$ is NHC(O)OR$^{12}$.
In yet another embodiment, R$^4$ is —NHC(O)N(R$^{12}$)$_2$.
In another embodiment, R$^4$ is NHC(O)R$^{12}$.
In one embodiment, R$^5$ is NHC(O)OR$^{12}$.
In yet another embodiment, R$^5$ is —NHC(O)N(R$^{12}$)$_2$.
In still another embodiment, R$^5$ is —OR$^{12}$.
In an additional embodiment, R$^5$ is —N(R$^{12}$)$_2$.
In another embodiment, R$^5$ is NHC(O)R$^{12}$.
In another embodiment, R$^{18}$ is C$_1$-C$_6$ alkyl.
In another embodiment, R$^{18}$ is C$_1$-C$_6$ alkenyl.
In another embodiment, R$^{18}$ is —O(C$_1$-C$_6$ alkyl).
In one embodiment, Y is N or CH, R$^4$ is NH$_2$, and R$^5$ is H.
In one embodiment, Y is N or CH, R$^4$ is NH$_2$, R$^5$ is H, and R$^1$ is

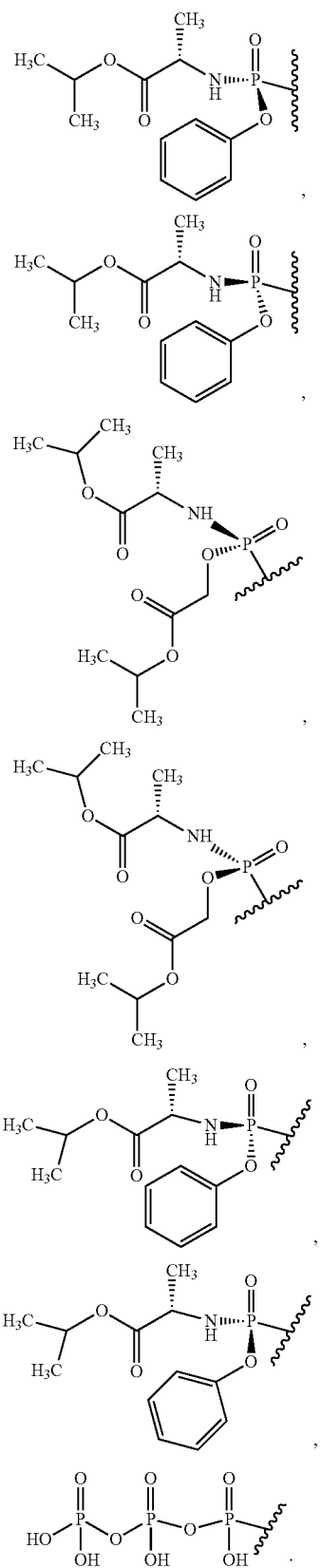

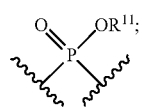

In another embodiment, Y is N or CH, $R^4$ is $NH_2$, $R^5$ is H, and $R^1$ and $R^2$ join to form a group having the structure:

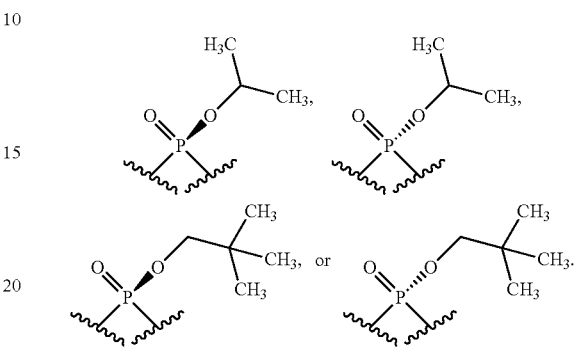

In one embodiment, the compounds of formula (I) have the formula (Ia):

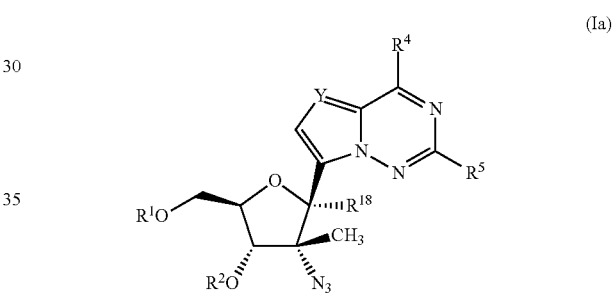

(Ia)

and pharmaceutically acceptable salts thereof,
wherein:
$R^1$ is H,

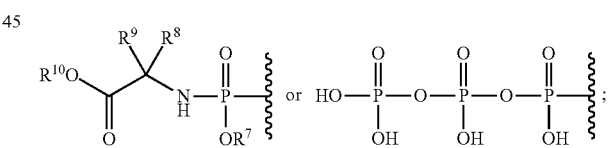

$R^2$ is H, or $R^1$ and $R^2$ join to form a group having the formula:

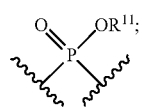

$R^4$ is H, OH or $-N(R^{12})_2$;
$R^5$ is H or $NH_2$,
$R^{18}$ is H, $-CN$ or $-OCH_3$;
$R^7$ is $-(C_1-C_3$ alkylene$)-C(O)O-(C_1-C_6$ alkyl$)$ or phenyl, wherein said phenyl group can be optionally substituted with a halo group;
$R^8$ and $R^9$ are each independently H or $C_1-C_6$ alkyl;

In another embodiment, Y is N or CH, $R^4$ is $NH_2$, $R^5$ is H, and $R^1$ and $R^2$ join to form a group having the formula:

$R^{10}$ is $C_1$-$C_6$ alkyl; and
$R^{11}$ is $C_1$-$C_6$ alkyl or $C_3$-$C_7$ cycloalkyl.

In another embodiment, the compounds of formula (I) have the formula (Ib):

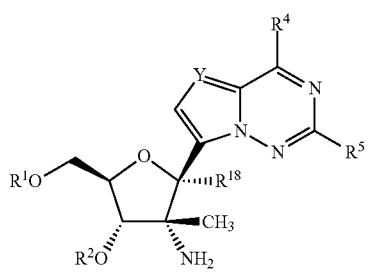

and pharmaceutically acceptable salts thereof, wherein:
$R^1$ is H,

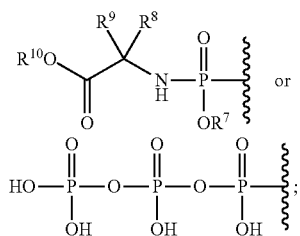

$R^2$ is H, or $R^1$ and $R^2$ join to form a group having the formula:

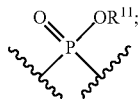

$R^4$ is H, OH or —$N(R^{12})_2$;
$R^5$ is H or $NH_2$,
$R^{18}$ is H, —CN or —$OCH_3$;
$R^7$ is —($C_1$-$C_3$ alkylene)-C(O)O—($C_1$-$C_6$ alkyl) or phenyl, wherein said phenyl group can be optionally substituted with a halo group;
$R^8$ and $R^9$ are each independently H or $C_1$-$C_6$ alkyl;
$R^{10}$ is $C_1$-$C_6$ alkyl; and
$R^{11}$ is $C_1$-$C_6$ alkyl or $C_3$-$C_7$ cycloalkyl.

In one embodiment, for the compounds of Formula (I), Formula (Ia), or Formula (Ib), Y is N.

In yet another embodiment, for the compounds of Formula (I), Formula (Ia), or Formula (Ib), Y is CH.

In one embodiment, for the compounds of Formula (I), Formula (Ia), or Formula (Ib), $R^1$ is H.

In another embodiment, for the compounds of Formula (I), Formula (Ia), or Formula (Ib), $R^1$ is

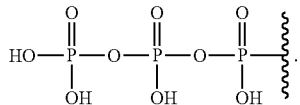 [SMILES: *P(=O)(O)OP(=O)(O)OP(=O)(O)O]

In yet another embodiment, for the compounds of Formula (I), Formula (Ia), or Formula (Ib), $R^1$ is

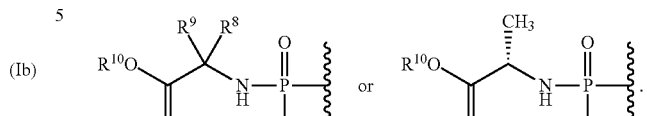

In still another embodiment, for the compounds of Formula (I), Formula (Ia), or Formula (Ib), $R^1$ is

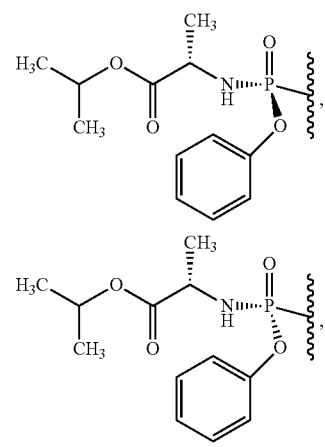

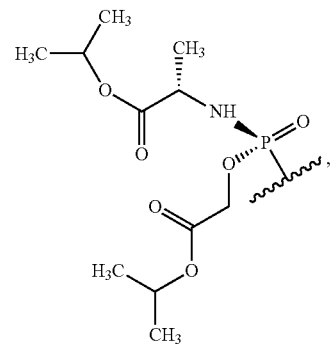

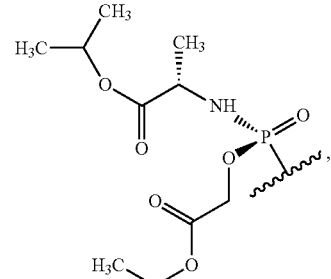

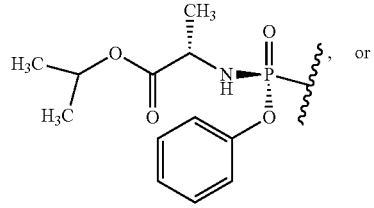

-continued

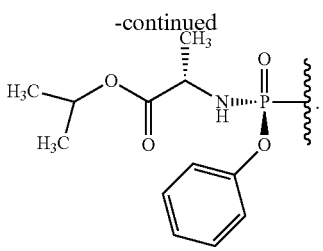

In one embodiment, for the compounds of Formula (I), Formula (Ia), or Formula (Ib), $R^2$ is H.

In one embodiment, for the compounds of Formula (I), Formula (Ia), or Formula (Ib), $R^1$ and $R^2$ join to form a group having the formula:

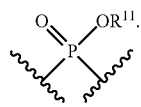

In another embodiment, for the compounds of Formula (I), Formula (Ia), or Formula (Ib), $R^1$ and $R^2$ join to form a group having the structure:

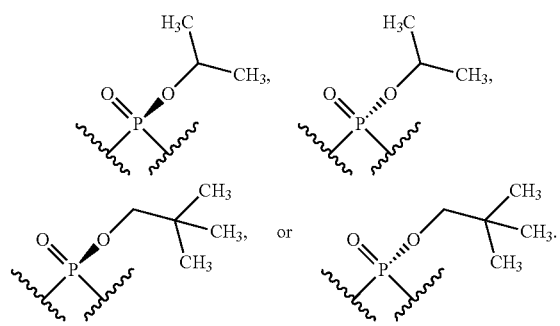

In one embodiment, for the compounds of Formula (I), Formula (Ia), or Formula (Ib), $R^4$ is H.

In another embodiment, for the compounds of Formula (I), Formula (Ia), or Formula (Ib), $R^4$ is OH.

In an additional embodiment, for the compounds of Formula (I), Formula (Ia), or Formula (Ib), $R^4$ is —N($R^{12}$)$_2$.

In another embodiment, for the compounds of Formula (I), Formula (Ia), or Formula (Ib), $R^4$ is —NH$_2$.

In one embodiment, for the compounds of Formula (I), Formula (Ia), or Formula (Ib), $R^5$ is H.

In another embodiment, for the compounds of Formula (I), Formula (Ia), or Formula (Ib), $R^5$ is —NH$_2$.

In one embodiment, for the compounds of Formula (I), Formula (Ia), or Formula (Ib), $R^{18}$ is H.

In an additional embodiment, for the compounds of Formula (I), Formula (Ia), or Formula (Ib), $R^{18}$ is —OCH$_3$.

In yet another embodiment, for the compounds of Formula (I), Formula (Ia), or Formula (Ib), $R^{18}$ is CN.

In one embodiment, for the compounds of Formula (I), Formula (Ia), or Formula (Ib), $R^7$ is —(C$_1$-C$_3$ alkylene)-C(O)O—(C$_1$-C$_6$ alkyl).

In another embodiment, for the compounds of Formula (I), Formula (Ia), or Formula (Ib), $R^7$ is phenyl, wherein said phenyl group can be optionally substituted with a halo group.

In one embodiment, for the compounds of Formula (I), Formula (Ia), or Formula (Ib), $R^8$ is H.

In another embodiment, for the compounds of Formula (I), Formula (Ia), or Formula (Ib), $R^8$ is $C_1$-$C_6$ alkyl.

In one embodiment, for the compounds of Formula (I), Formula (Ia), or Formula (Ib), $R^9$ is H.

In another embodiment, for the compounds of Formula (I), Formula (Ia), or Formula (Ib), $R^9$ is $C_1$-$C_6$ alkyl.

In one embodiment, for the compounds of Formula (I), Formula (Ia), or Formula (Ib), $R^{11}$ is $C_1$-$C_6$ alkyl.

In another embodiment, for the compounds of Formula (I), Formula (Ia), or Formula (Ib), $R^{11}$ is $C_3$-$C_7$ cycloalkyl.

In one embodiment, for the compounds of Formula (I), Formula (Ia), or Formula (Ib), the group:

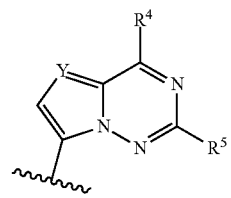

has the structure:

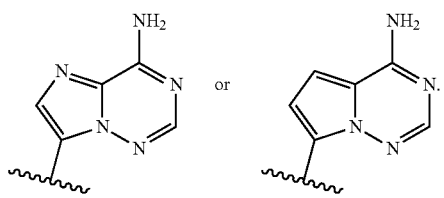 [SMILES: *c1cnc2c(N)ncnn12 ; *c1ccc2c(N)ncnn12]

In one embodiment, for the compounds of Formula (Ia) or Formula (Ib), $R^1$ is H, $R^2$ is H, and the group:

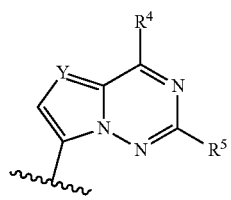

has the structure:

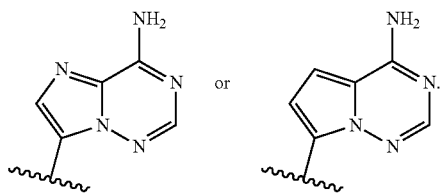 [SMILES: *c1cnc2c(N)ncnn12 ; *c1ccc2c(N)ncnn12]

In another embodiment, for the compounds of Formula (Ia) or Formula (Ib), $R^1$ is:

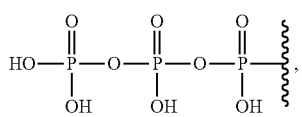
$R^2$ is H, and the group:
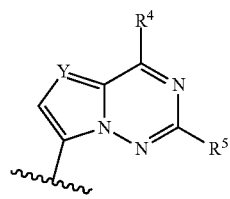
has the structure:
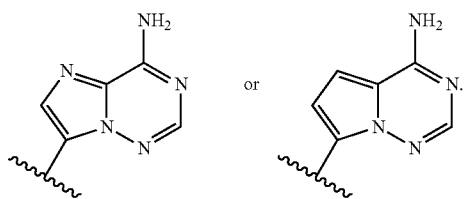 [SMILES: *c1cnc2c(N)ncnn12 ; *c1ccc2c(N)ncnn12]
In another embodiment, for the compounds of Formula (Ia) or Formula (Ib), $R^1$ is:
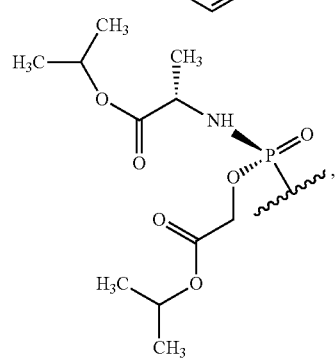
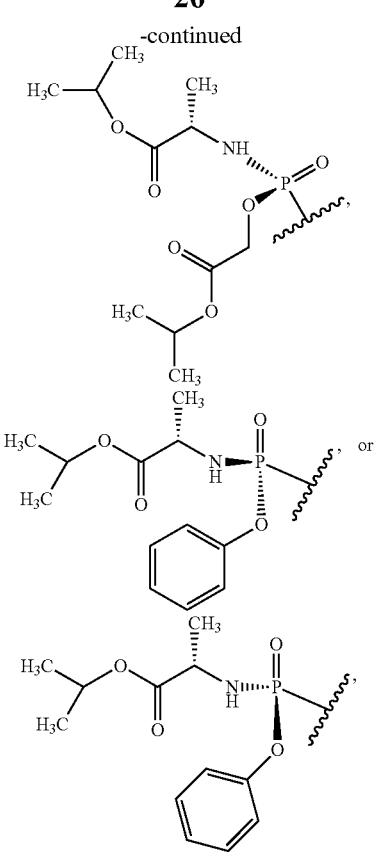
$R^2$ is H, and the group:
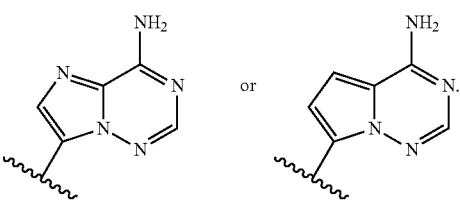
has the structure:
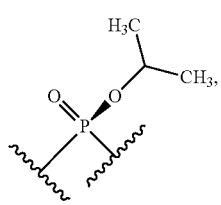
In another embodiment, for the compounds of Formula (Ia) or Formula (Ib), $R^1$ and $R^2$ join to form a group having the structure:

-continued

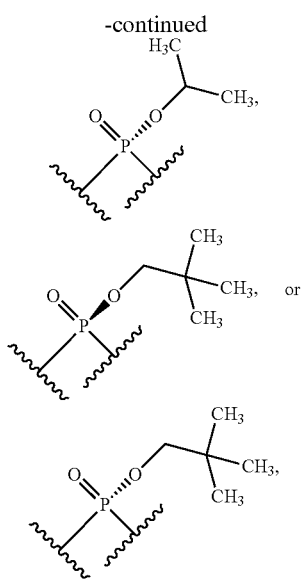

$R^2$ is H, and the group:

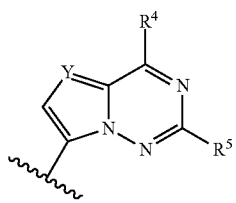

has the structure:

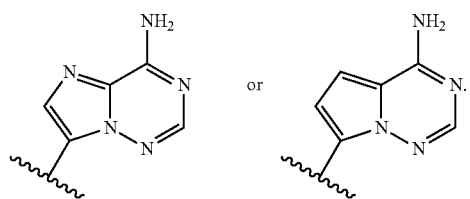 [SMILES: *c1cnc2c(N)ncnn12 ; *c1ccc2c(N)ncnn12]

In one embodiment, variables A, X, Y, $R^1$, $R^2$, $R^3$, $R^4$, $R^5$, and $R^{18}$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors, HCV NS5B polymerase inhibitors and HCV NS5A inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors, HCV NS5B polymerase inhibitors and HCV NS5A inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors, HCV NS5B polymerase inhibitors and HCV NS5A inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

Additional embodiments of the invention include the pharmaceutical compositions, combinations and methods set forth in (a)-(k) above and the uses set forth in the discussion below, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

Uses of the 2'-Disubstituted Nucleoside Derivatives

The 2'-Disubstituted Nucleoside Derivatives are useful in human and veterinary medicine for treating or preventing a viral infection in a patient. In one embodiment, the 2'-Disubstituted Nucleoside Derivatives can be inhibitors of viral replication. In another embodiment, the 2'-Disubstituted Nucleoside Derivatives can be inhibitors of HCV replication. Accordingly, the 2'-Disubstituted Nucleoside Derivatives are useful for treating viral infections, such as HCV.

The present invention also includes a compound of the present invention for use (i) in, (ii) as a medicament for, or (iii) in the preparation of a medicament for: (a) medicine, (b)

inhibiting HCV replication or (c) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators, as discussed in more detail, infra.

In one embodiment, the present invention includes the use of a compound of the present invention, or a pharmaceutically acceptable salt thereof, in a pharmaceutical composition for inhibiting HCV NS5B activity or for preventing and/or treating infection by HCV in a patient in need thereof.

In accordance with the invention, the 2'-Disubstituted Nucleoside Derivatives can be administered to a patient in need of treatment or prevention of a viral infection. Accordingly, in one embodiment, the invention provides methods for treating a viral infection in a patient comprising administering to the patient an effective amount of at least one 2'-Disubstituted Nucleoside Derivative or a pharmaceutically acceptable salt thereof.

The 2'-Disubstituted Nucleoside Derivatives are also useful in the preparation and execution of screening assays for antiviral compounds. For example the 2'-Disubstituted Nucleoside Derivatives are useful for identifying resistant HCV replicon cell lines harboring mutations within NS5B, which are excellent screening tools for more powerful antiviral compounds. Furthermore, the 2'-Disubstituted Nucleoside Derivatives are useful in establishing or determining the binding site of other antivirals to the HCV NS5B polymerase.

In addition, the triphosphate forms of the compounds of the invention can inhibit NS5B enzymatic activity. Non-triphosphate forms of the compounds of the invention may provide a starting point for phosphorylation.

Treatment or Prevention of HCV Infection:

The 2'-Disubstituted Nucleoside Derivatives are useful in the inhibition of HCV, the treatment of HCV infection and/or reduction of the likelihood or severity of symptoms of HCV infection and the inhibition of HCV viral replication and/or HCV viral production in a cell-based system. For example, the 2'-Disubstituted Nucleoside Derivatives are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one 2'-Disubstituted Nucleoside Derivative or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b.

Combination Therapy:

In another embodiment, the present methods for treating or preventing HCV infection can further comprise the administration of one or more additional therapeutic agents which are not 2'-Disubstituted Nucleoside Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one 2'-Disubstituted Nucleoside Derivative (which may include two or more different 2'-Substituted Nucleoside Derivatives), or a pharmaceutically acceptable salt thereof, and (ii) at least one additional therapeutic agent that is other than a 2'-Disubstituted Nucleoside Derivative, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 2'-Disubstituted Nucleoside Derivative and an additional therapeutic agent may be present in fixed amounts (dosage amounts) in a single dosage unit (e.g., a capsule, a tablet and the like).

In one embodiment, the at least one 2'-Disubstituted Nucleoside Derivative is administered during a time when the additional therapeutic agent(s) exert their prophylactic or therapeutic effect, or vice versa.

In another embodiment, the at least one 2'-Disubstituted Nucleoside Derivative and the additional therapeutic agent(s) are administered in doses commonly employed when such agents are used as monotherapy for treating a viral infection.

In another embodiment, the at least one 2'-Disubstituted Nucleoside Derivative and the additional therapeutic agent(s) are administered in doses lower than the doses commonly employed when such agents are used as monotherapy for treating a viral infection.

In still another embodiment, the at least one 2'-Disubstituted Nucleoside Derivative and the additional therapeutic agent(s) act synergistically and are administered in doses lower than the doses commonly employed when such agents are used as monotherapy for treating a viral infection.

In one embodiment, the at least one 2'-Disubstituted Nucleoside Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one 2'-Disubstituted Nucleoside Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one 2'-Disubstituted Nucleoside Derivative and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, one or more compounds of the invention are administered with one or more additional therapeutic agents, including but not limited to the therapeutic agents described, supra.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In another embodiment, one or more compounds of the present invention are administered with one additional therapeutic agent selected from an HCV protease inhibitor, an interferon, a pegylated interferon and ribavirin. In another embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759NX-759 (ViroChem Pharma/Vertex), HCV-371 (Wyeth/VirroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/Vertex), VCH-916 (Viro-Chem), VCH-716(ViroChem), GSK-71185 (Glaxo Smith-Kline), ANA598 (Anadys), GSK-625433 (Glaxo Smith-Kline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125; and the following compounds:

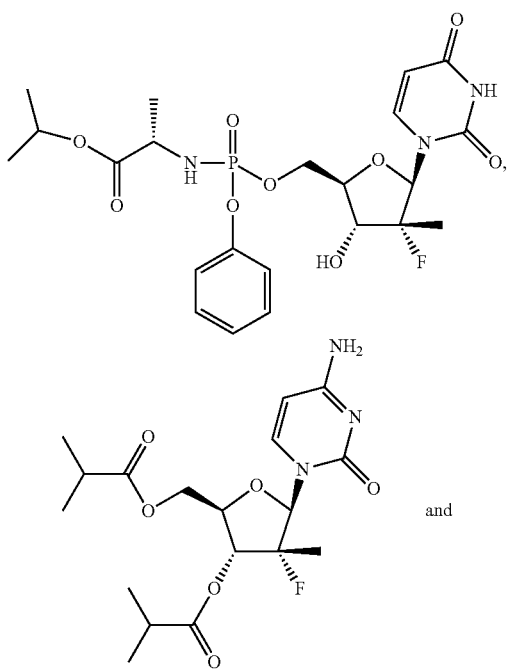

and

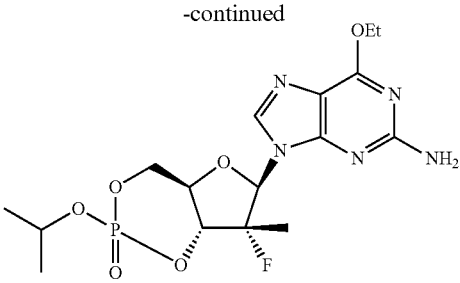

and pharmaceutically acceptable salts thereof.

Interferons useful in the present compositions and methods include, but are not limited to, interferon alfa-2a, interferon alfa-2b, interferon alfacon-1 and petroleum etherG-interferon alpha conjugates. "PEG-interferon alpha conjugates" are interferon alpha molecules covalently attached to a petroleum etherG molecule. Illustrative petroleum etherG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name petroleum etherG-Intron™ from Schering-Plough Corporation), interferon alpha-2b-XL (e.g., as sold under the trade name petroleum etherG-Intron™), interferon alpha-2c (Berofor Alpha™, Boehringer Ingelheim, Ingelheim, Germany), petroleum etherG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Examples of viral protease inhbitors useful in the present compositions and methods include, but are not limited to, an HCV protease inhibitor. Examples of HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, the following compounds:

35
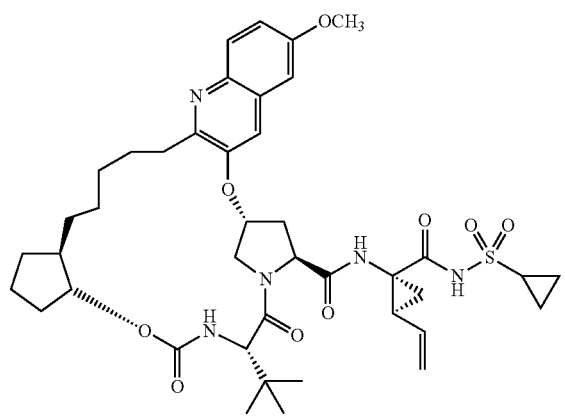
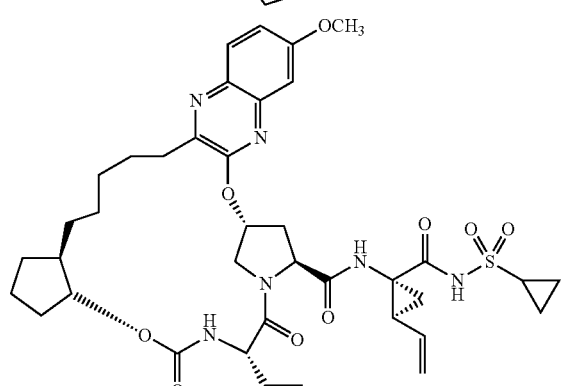
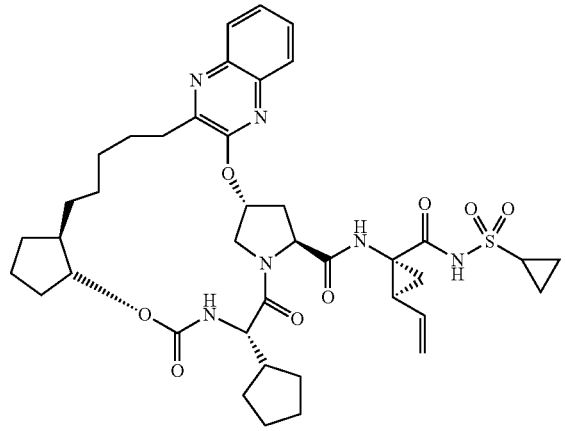
36
-continued
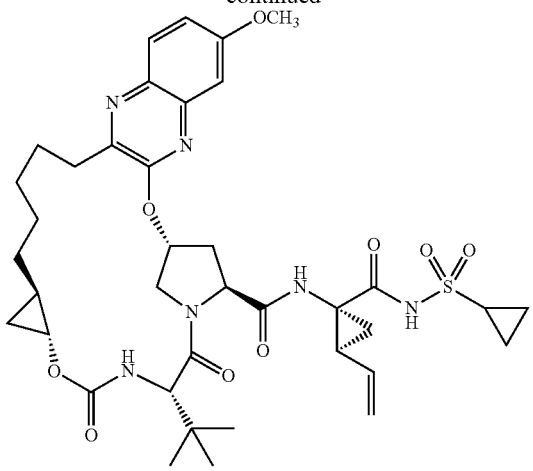
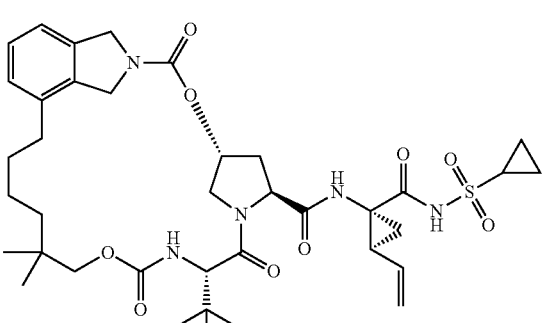
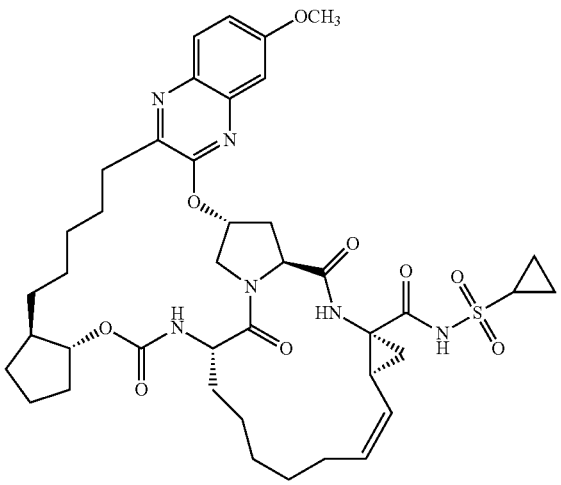

37 38
-continued -continued
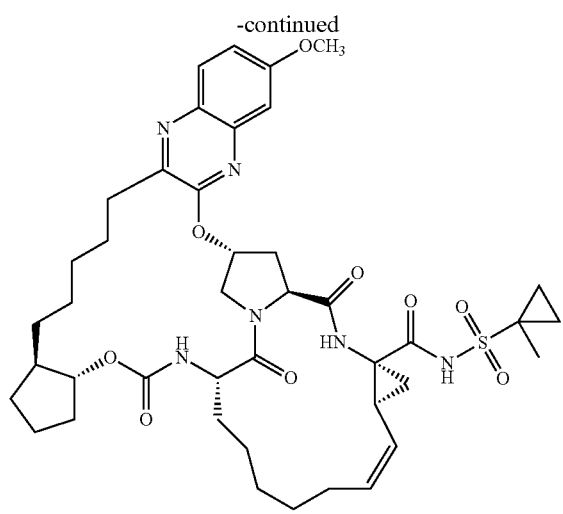
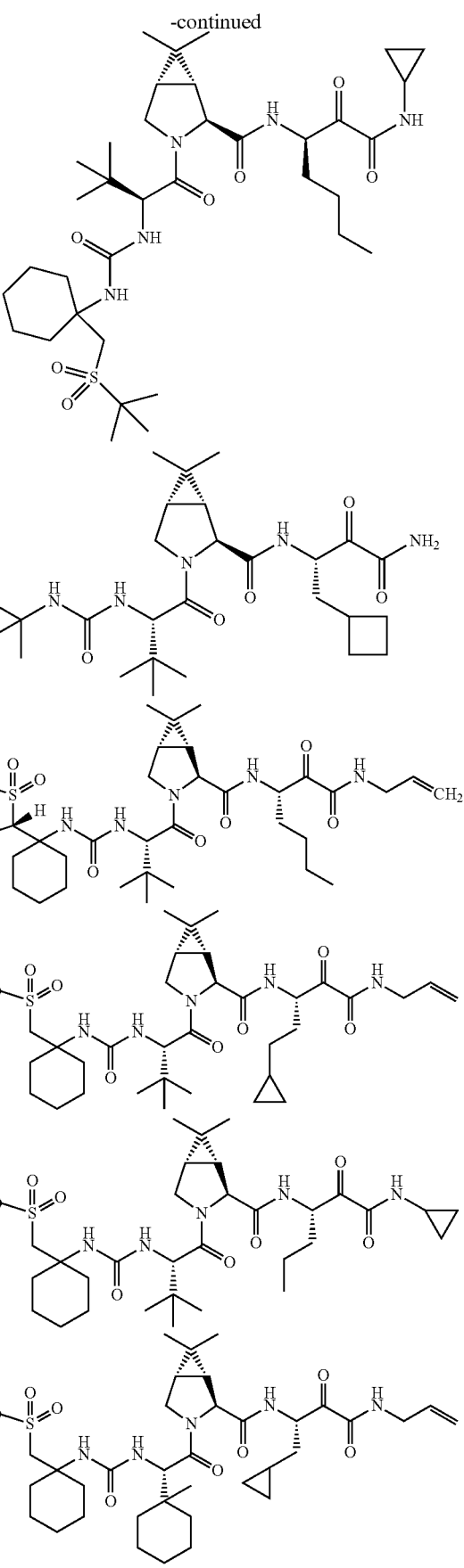

-continued
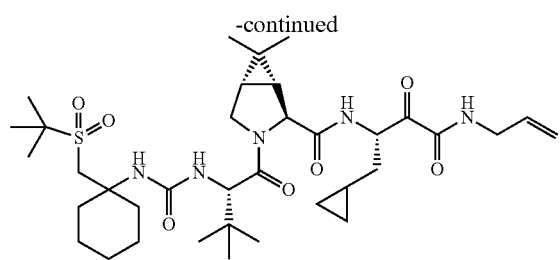
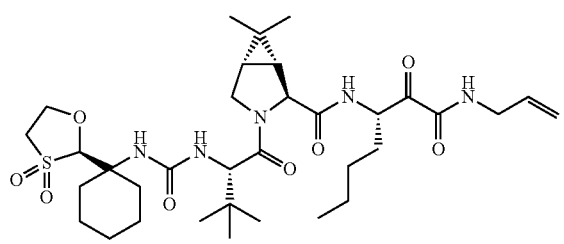
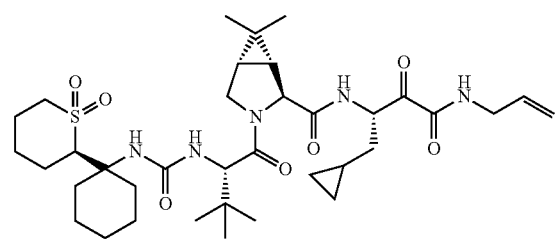
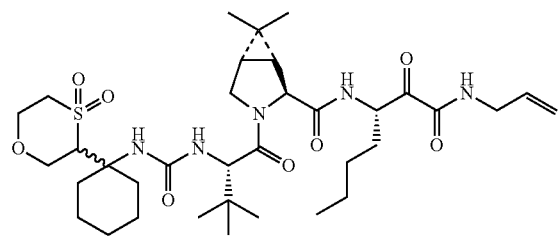
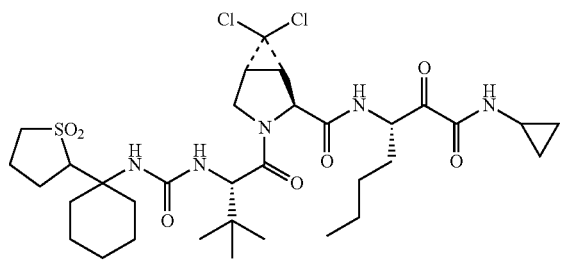
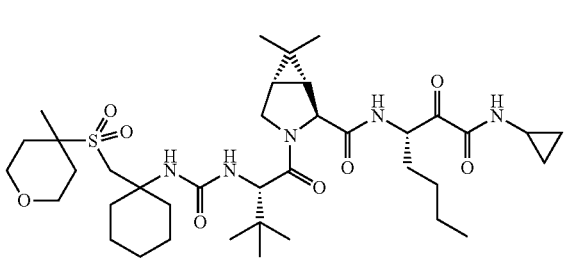
-continued
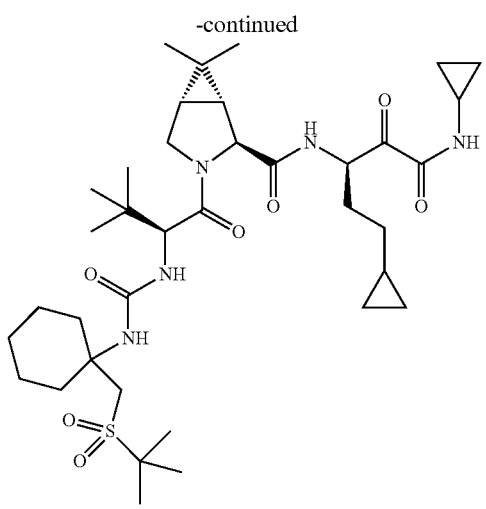
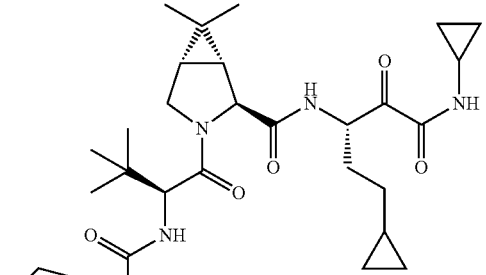
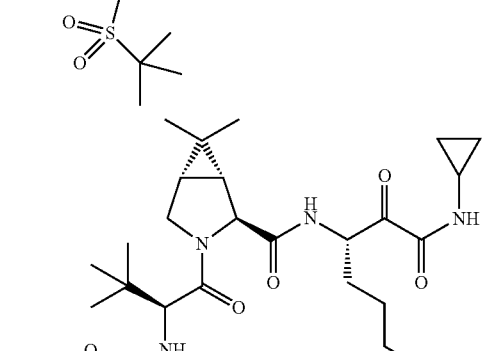
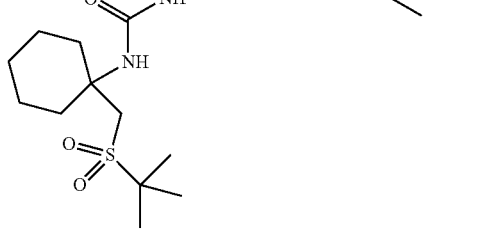
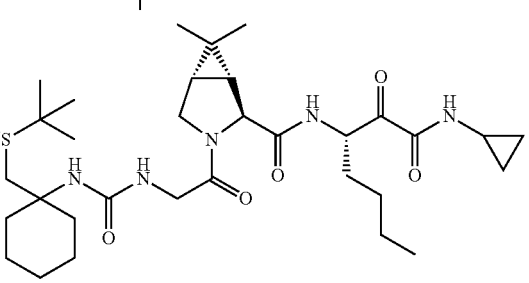

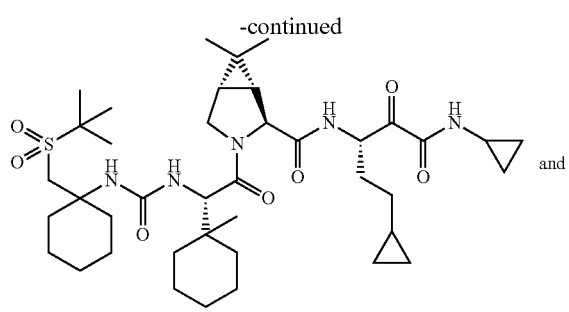

and pharmaceutically acceptable salts thereof.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

HCV NS5A inhibitors useful in the present compositions and methods include, but are not limited to, ACH-2928 (Achilon), A-832 (Arrow Therpeutics), AZD-7295 (Astra Zeneca/Arrow), GS-5885 (Gilead), PPI-461 (Presidio), PPI-1301 (Presidio), BMS-824383 (Bristol-Myers Squibb) and BMS-790052 (Bristol-Myers Squibb). Additional HCV NS5A inhibitors useful as second additional therapeutic agents in the present compositions and methods include, but are not limited to those disclosed in International Publication No. WO 2010/111483 and the following compounds:

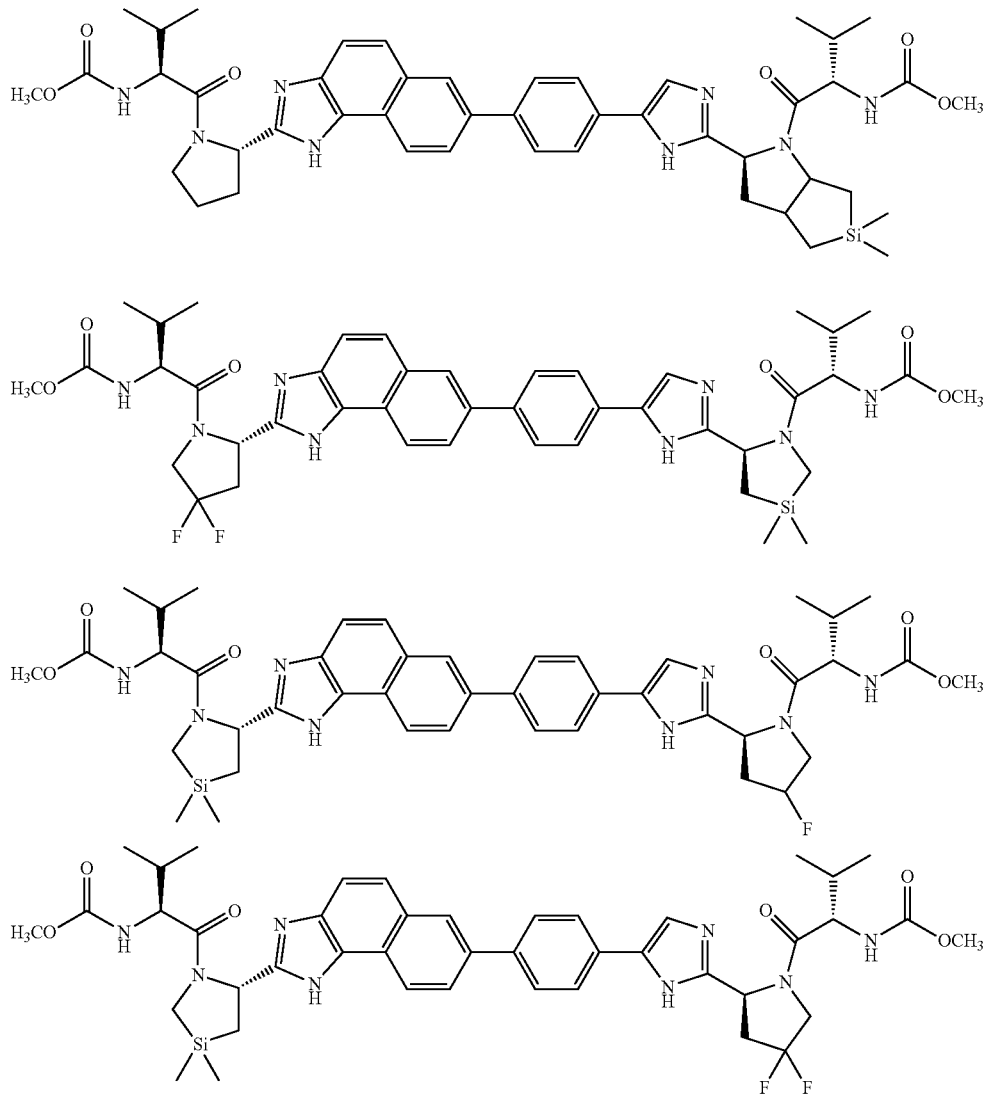

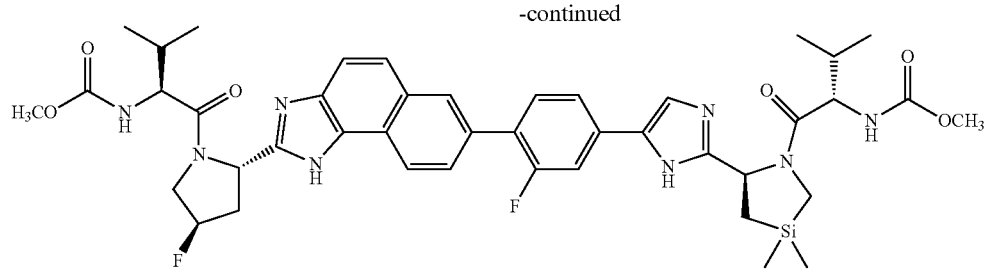
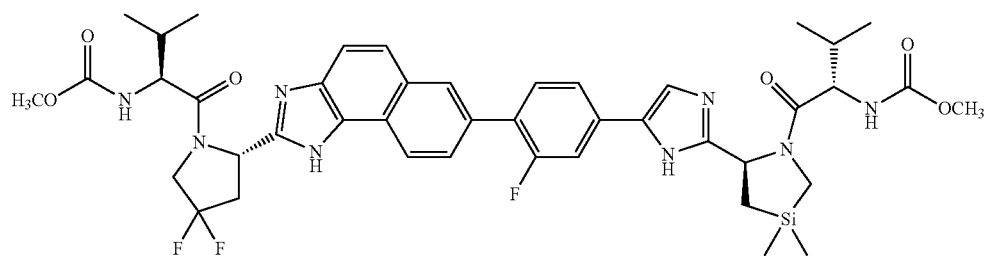
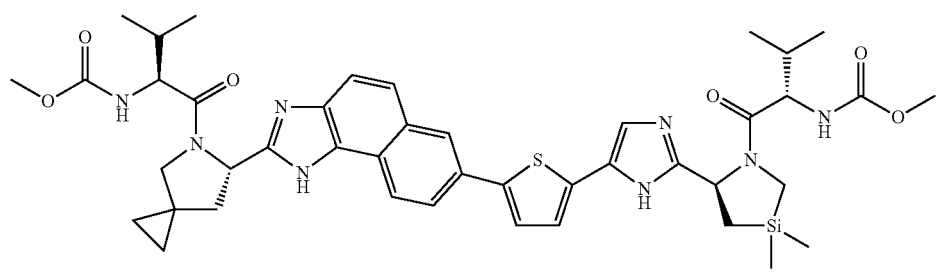
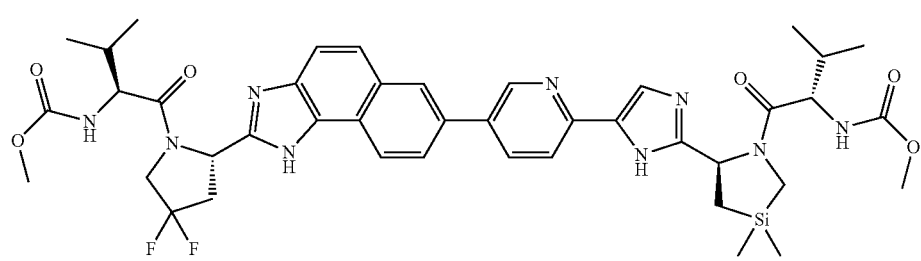
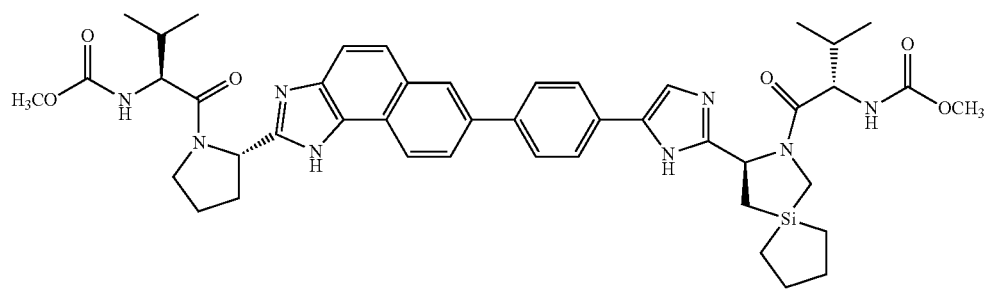
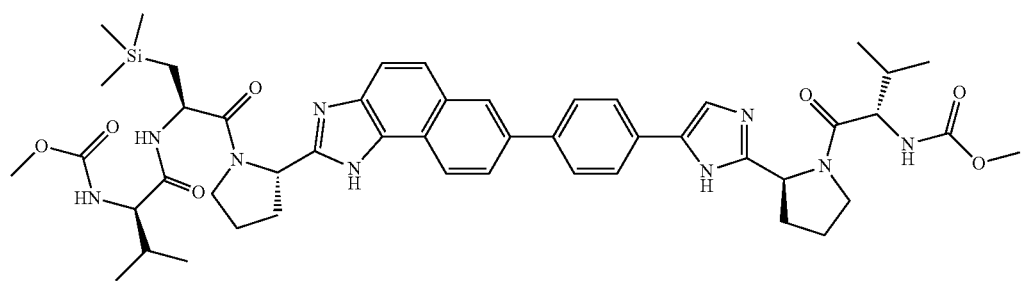

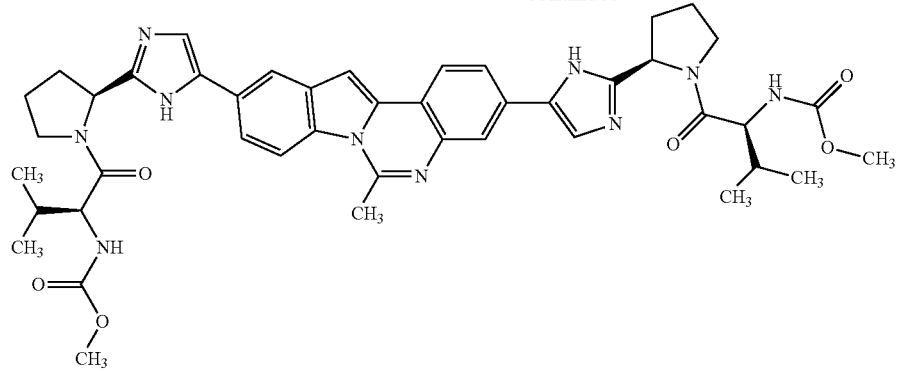
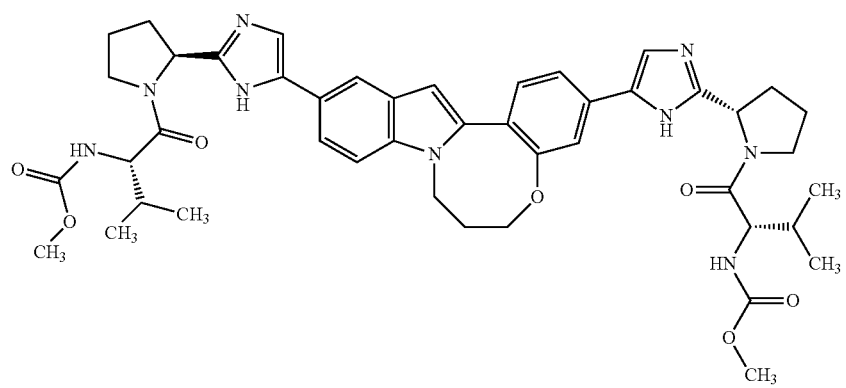
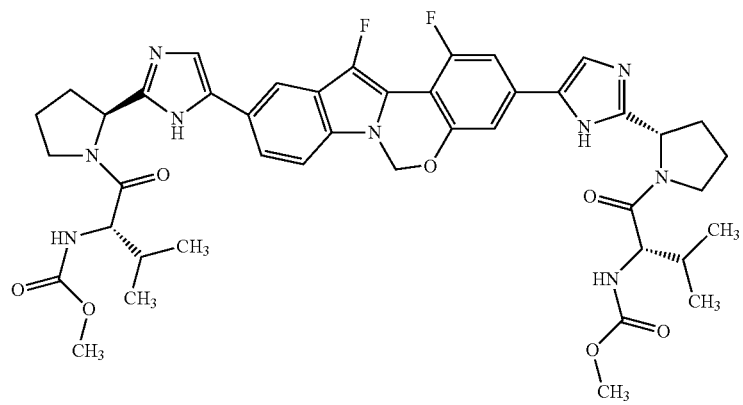
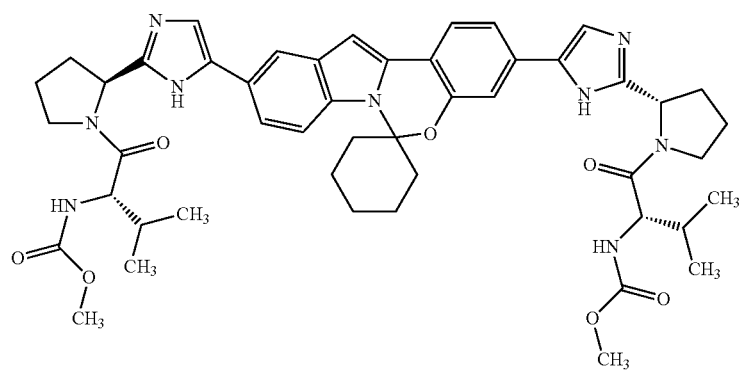

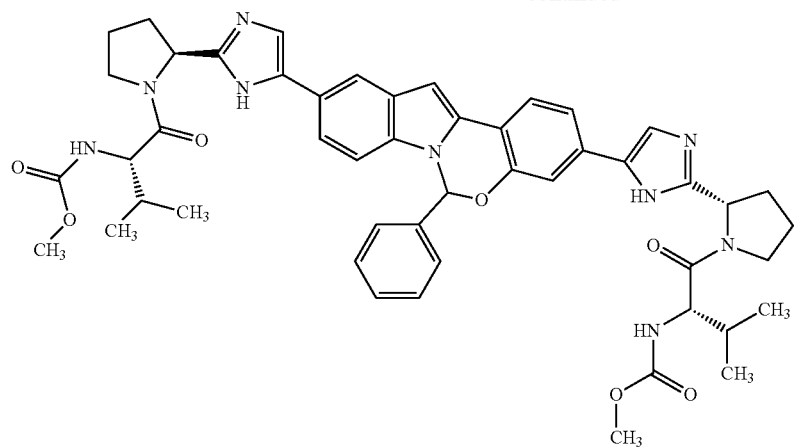
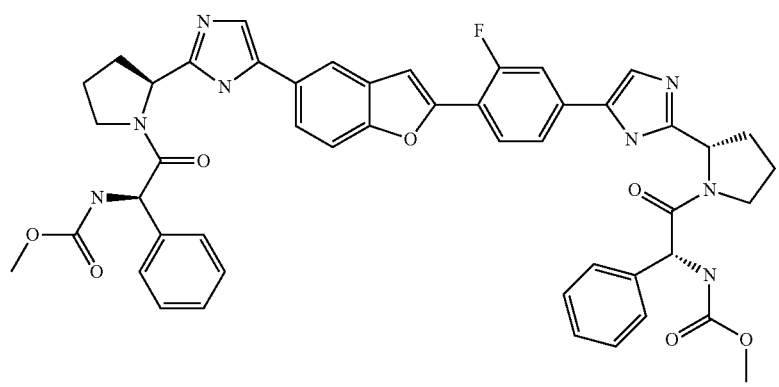
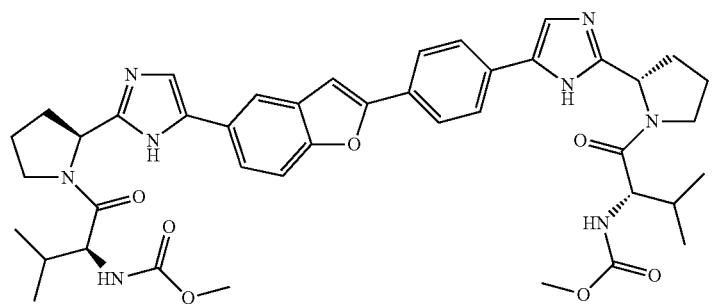
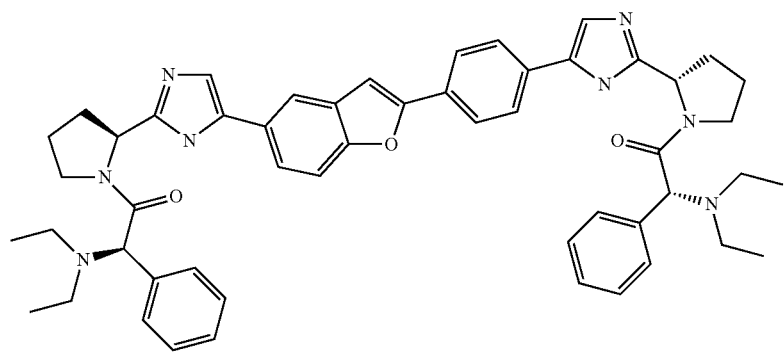

-continued

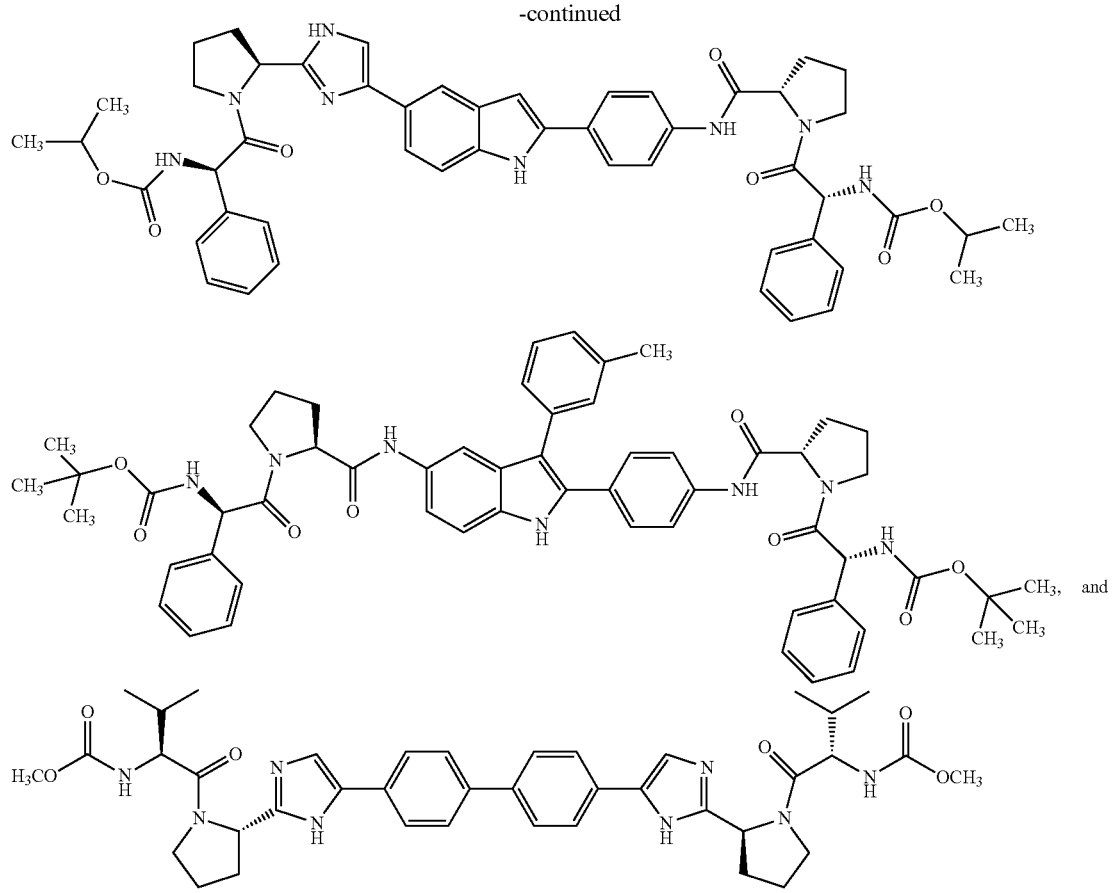

and pharmaceutically acceptable salts thereof.

HCV replicase inhibitors useful in the present compositions and methods include, but are not limited to, those disclosed in U.S. Patent Publication No. US20090081636.

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the 2'-Disubstituted Nucleoside Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one 2'-Disubstituted Nucleoside Derivative(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

Due to their activity, the 2'-Disubstituted Nucleoside Derivatives are useful in veterinary and human medicine. As described above, the 2'-Disubstituted Nucleoside Derivatives are useful for treating or preventing HCV infection in a patient in need thereof.

When administered to a patient, the 2'-Disubstituted Nucleoside Derivatives can be administered as a component of a composition that comprises a pharmaceutically acceptable carrier or vehicle. The present invention provides pharmaceutical compositions comprising an effective amount of at least one 2'-Disubstituted Nucleoside Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as *acacia*, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 2'-Disubstituted Nucleoside Derivatives are administered orally.

In another embodiment, the one or more 2'-Disubstituted Nucleoside Derivatives are administered intravenously.

In one embodiment, a pharmaceutical preparation comprising at least one 2'-Disubstituted Nucleoside Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the 2'-Disubstituted Nucleoside Derivative(s) by weight or volume. In various embodiments, the present compositions can contain, in one embodiment, from about 1% to about 70% or from about 5% to about 60% of the 2'-Disubstituted Nucleoside Derivative(s) by weight or volume.

The quantity of 2'-Disubstituted Nucleoside Derivative in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 2'-Disubstituted Nucleoside Derivatives will be regulated according to the judgment of the attending clinician considering such factors as age, condition and size of the patient as well as severity of the symptoms being treated. Generally, a total daily dosage of the 2'-Disubstituted Nucleoside Derivatives range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one 2'-Disubstituted Nucleoside Derivative or a pharmaceutically acceptable salt thereof; (ii) one or more additional therapeutic agents that are not a 2'-Disubstituted Nucleoside Derivative; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and wto additional therapeutic agents, each of which are independently selected from the group consisting of HCV antiviral agents, immunomodulators, and anti-infective agents.

Methods for Making the Compounds of Formula (I):

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A-L below. Alternative synthetic pathways and analogous structures will be apparent to those skilled in the art of organic synthesis.

Scheme A shows a method useful for making nucleoside compounds of formula A12 or A13, which correspond to the Compounds of Formula (I), wherein $R^1$ is H, $R^2$ is H, $R^3$ is $CH_3$, $R^5$ is H, and A is $N_3$ or $NH_2$

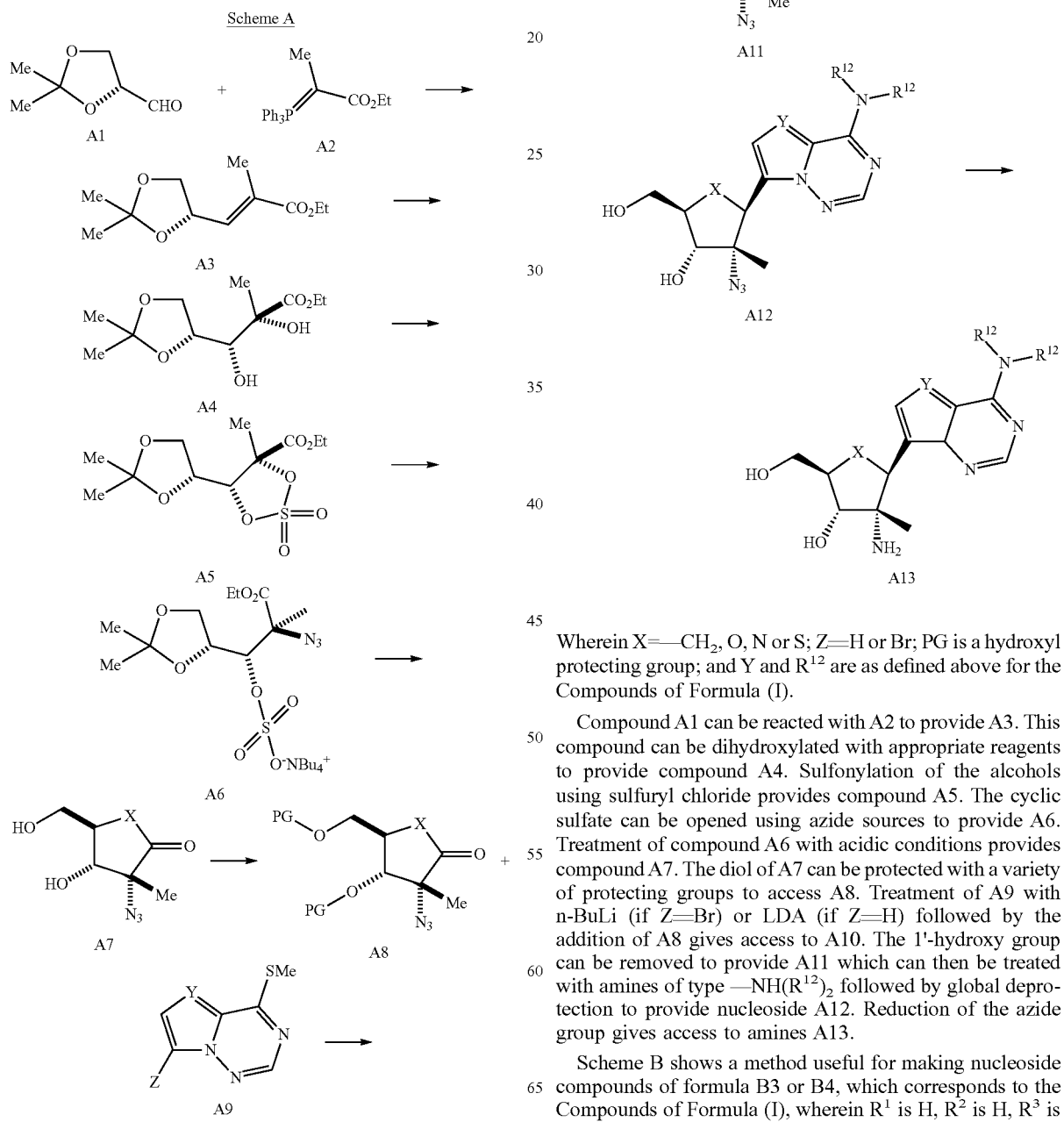

Wherein X=—$CH_2$, O, N or S; Z=H or Br; PG is a hydroxyl protecting group; and Y and $R^{12}$ are as defined above for the Compounds of Formula (I).

Compound A1 can be reacted with A2 to provide A3. This compound can be dihydroxylated with appropriate reagents to provide compound A4. Sulfonylation of the alcohols using sulfuryl chloride provides compound A5. The cyclic sulfate can be opened using azide sources to provide A6. Treatment of compound A6 with acidic conditions provides compound A7. The diol of A7 can be protected with a variety of protecting groups to access A8. Treatment of A9 with n-BuLi (if Z=Br) or LDA (if Z=H) followed by the addition of A8 gives access to A10. The 1'-hydroxy group can be removed to provide A11 which can then be treated with amines of type —NH($R^{12}$)$_2$ followed by global deprotection to provide nucleoside A12. Reduction of the azide group gives access to amines A13.

Scheme B shows a method useful for making nucleoside compounds of formula B3 or B4, which corresponds to the Compounds of Formula (I), wherein $R^1$ is H, $R^2$ is H, $R^3$ is $CH_3$, $R^5$ is H, and A is $N_3$ or $NH_2$.

Scheme C shows a method useful for making nucleoside compounds of formula C5 or C6, which correspond to other Compounds of Formula (i), wherein $R^2$ is H, $R^3$ is $CH_3$, $R^5$ is H, and A is $N_3$ or $NH_2$.

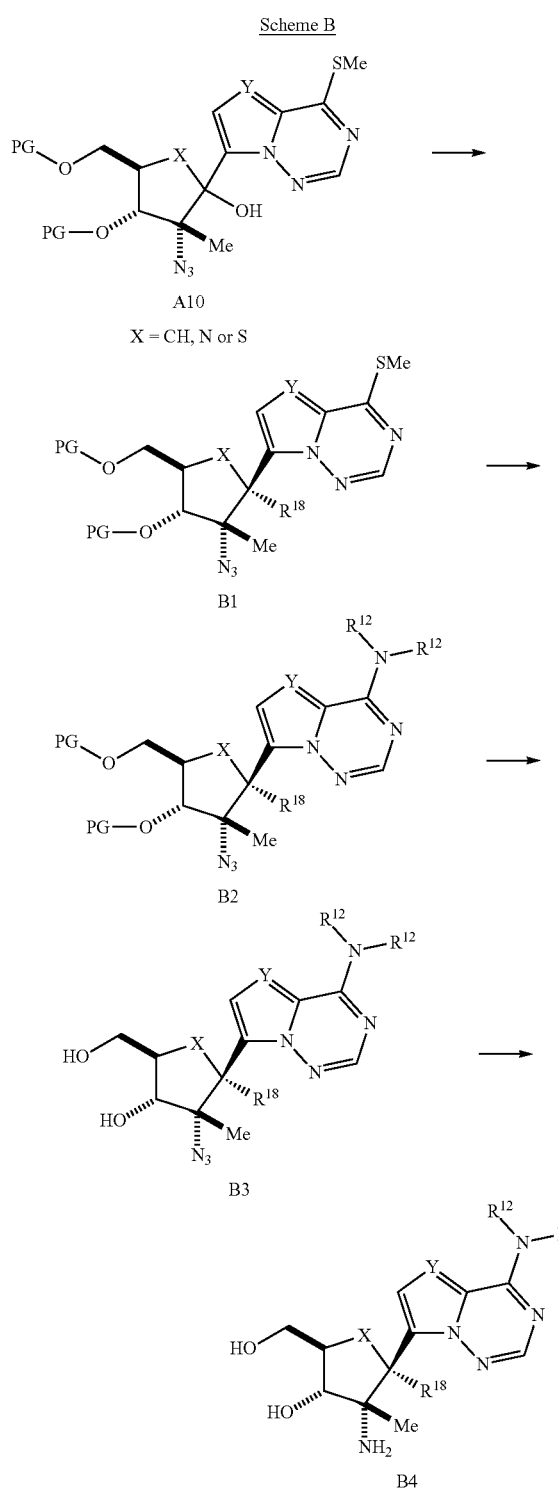

A10
X = CH, N or S

B1

B2

B3

B4

Wherein X=—$CH_2$, O, N or S; PG is a hydroxyl protecting group and Y, $R^{18}$, and $R^{12}$ are as defined above for the Compounds of Formula (I).

Compounds of structure A10 can be treated under Lewis acidic conditions in the presence of compounds such as TMS-$R^{18}$ to provide compounds of type B1. Compounds of type B1 can be treated with amines of type —$NH(R^{12})_2$ to provide B2. Global deprotection of B2 provides nucleoside B3. Reduction of the azide group gives access to amines B4.

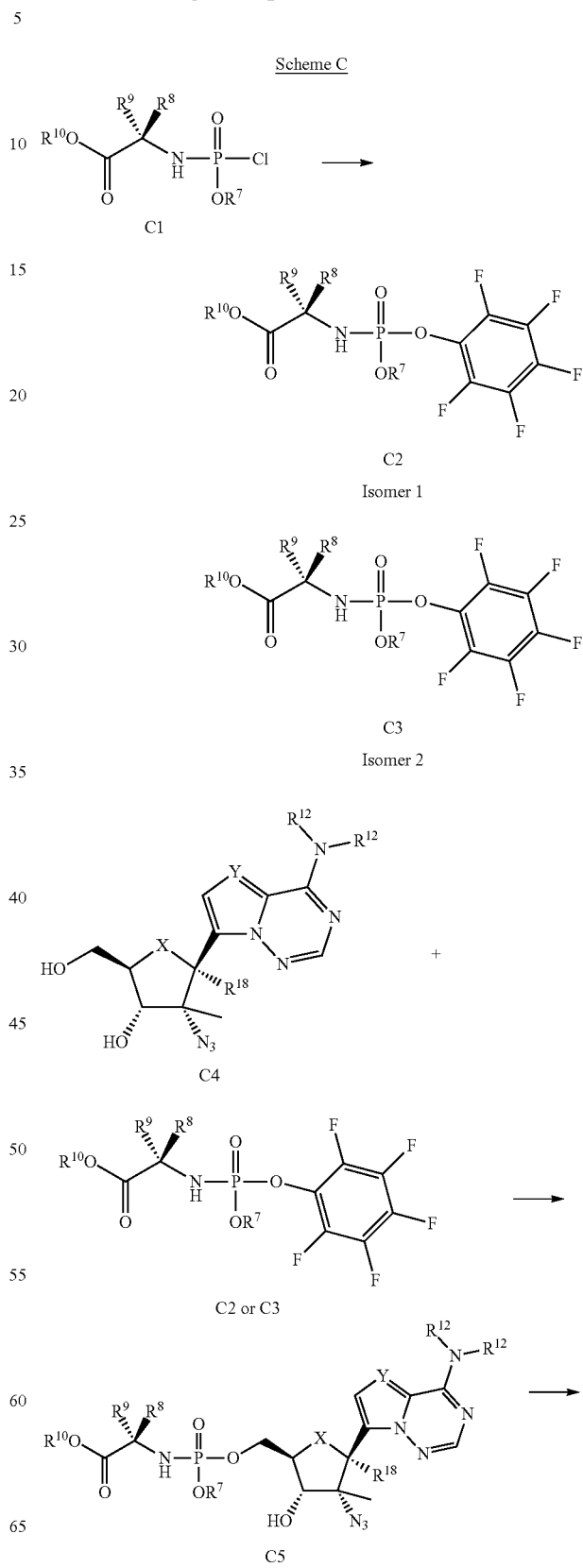

Scheme C

C1

C2
Isomer 1

C3
Isomer 2

C4

C2 or C3

C5

-continued

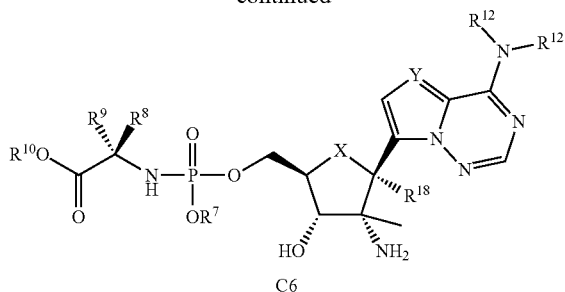

C6

Wherein X=—CH$_2$, O, N or S; and Y, R$^7$, R$^8$, R$^9$, R$^{10}$, R$^{12}$ and R$^{18}$ are as defined above for the Compounds of Formula (I).

A compound C1 can be reacted with pentafluoro phenol to produce two isomers C2 and C3. These isomers can be individually reacted with C4 to produce compounds of structure C5. Reduction of the azide group gives access to amines C6.

Scheme D shows a method useful for making nucleoside compounds of formula D2 or D3, which correspond to the Compounds of Formula (I), wherein R$^3$ is CH$_3$, R$^5$ is H, and R$^1$ and R$^2$ join to form a group having the formula

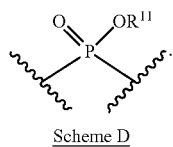

Scheme D

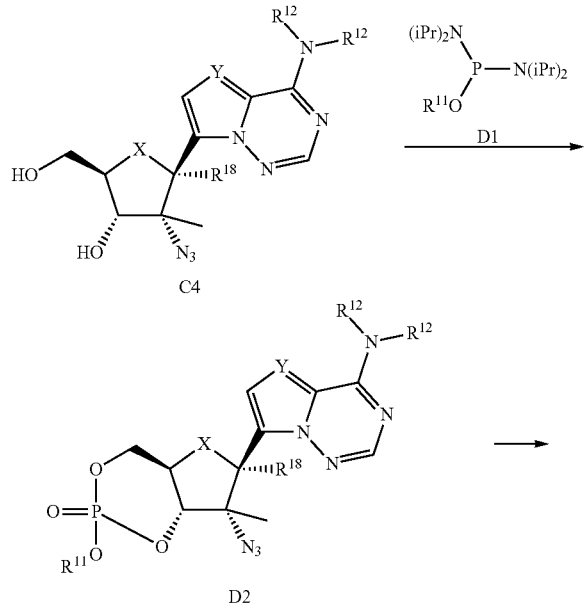

Wherein X=—CH$_2$, O, N or S; and Y, R$^{11}$, R$^{12}$, and R$^{18}$ are as defined above for the Compounds of Formula (I).

A compound of formula C4 can be reacted with a phosphoramidate compound of formula D1 followed by oxidation with, for example, m-chloroperbenzoic acid to provide a cyclic phosphate ester of formula D2. Reduction of the azide group gives access to amines D3.

Scheme E shows a method useful for making nucleoside compounds of formula E1 or E2, which correspond to the Compounds of Formula (I), wherein R1 is

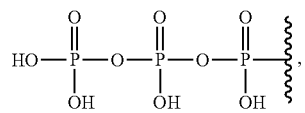

R$^2$ is H, R$^3$ is CH$_3$, R$^5$ is H, and A is N$_3$ or NH$_2$

Scheme E

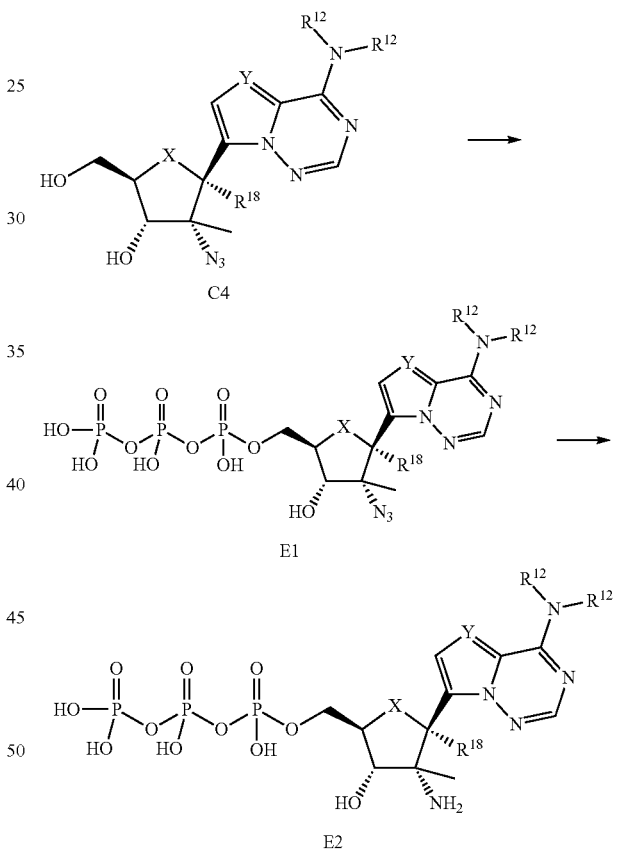

Wherein X=—CH$_2$, O, N or S; and R$^{12}$, R$^{18}$ and Y are as defined above for the Compounds of Formula (I).

Nucleosides such as C4 can be converted to the triphosphate E1 by treatment with phosphorus oxychloride followed by pyrophosphate. Reduction of the azide group gives access to amines E2.

Compounds of formula A12, A13, B3, B4, C5, C6, D2, D3, E1, and E2 may be further elaborated using methods that would be well-known to those skilled in the art of organic synthesis or, for example, the methods described in the Examples below, to make the full scope of the Compounds of Formula (I).

One skilled in the art of organic synthesis will recognize that the synthesis of compounds with multiple reactive functional groups, such as —OH and NH$_2$, may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

The starting materials used and the intermediates prepared using the methods set forth in Schemes A-E may be isolated and purified if desired using conventional techniques, including but not limited to filtration, distillation, crystallization, chromatography and alike. Such materials can be characterized using conventional means, including physical constants and spectral data.

Non-limiting examples of the Compounds of Formula (I) include compounds 1-25 as set forth in the Examples below, and pharmaceutically acceptable salts thereof.

EXAMPLES

General Methods

Solvents, reagents, and intermediates that are commercially available were used as received. Reagents and intermediates that are not commercially available were prepared in the manner as described below. $^1$H NMR spectra were obtained on a Varian VNMR System 400 (400 MHz) and are reported as ppm downfield from Me$_4$Si with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The parent ion is given. Flash chromatography on silica gel was performed using prepacked normal phase silica from Isco, Biotage, Inc. or bulk silica from Fisher Scientific. Unless otherwise indicated, flash chromatography on silica gel was performed using a gradient elution of hexanes/ethyl acetate, from 100% hexanes to 100% ethyl acetate.

Example 1

Preparation of Int-1h

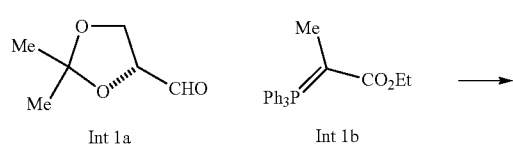

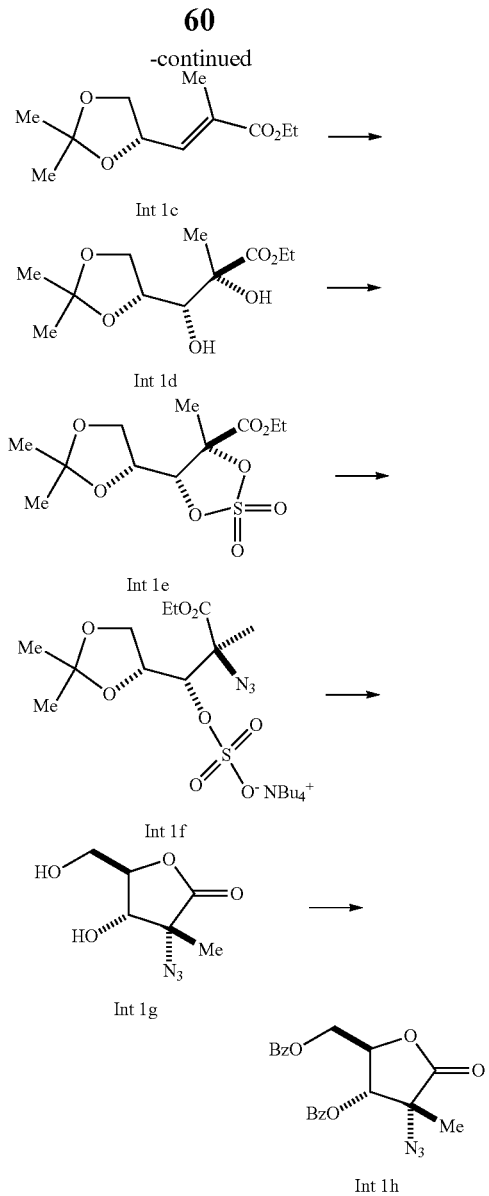

Step A: Synthesis of Intermediate Compound Int 1c

To a stirred solution of Int 1b (15.9 kg, 43.95 mol) in DCM (44.2 L) was added a solution of Int 1a (6.0 kg, 46.15 mol) in DCM (12 L) slowly with stirring at 0-5° C. over 1.5 hours. The resulting solution was stirred for 3 hours at 0-5° C. The resulting mixture was concentrated in vacuo. The residue was treated with petroleum-ether (50 L) to provide a precipitate. The solid was removed by vacuum filtration and the filtrate was distilled under reduced pressure (4 mm Hg) and the fraction at 110-140° C. was collected to provide Int 1c as a light yellow liquid (8.2 kg, 82.5%).

Step B: Synthesis of Intermediate Compound Int 1d

To a stirred solution of Int 1c (4.2 kg, 19.63 mol), glycol (4.9 kg, 78.50 mol), NaHCO$_3$ (5.0 kg, 58.89 mol) and water (8.4 L) in acetone (44.0 L) was added KMnO$_4$ (3.3 kg, 20.61 mol) in portions at −10° C. over 2 hours. The resulting solution was stirred for 1 hour at −10° C. in a liquid nitrogen bath. The reaction was then quenched by the addition of NaHSO$_3$ solution (6.0 L). The resulting solid was removed by filtration. The filtrate was diluted with H₂O (20 L) and extracted with ethyl acetate (4×3 L). The combined organic layers were dried over anhydrous Na₂SO₄, filtered and concentrated in vacuo. The residue obtained was treated with hexanes (20 L) −10° C. The resulting solid was collected by filtration and dried at 45° C. to provide Int 1d as a white solid (3.2 kg, 65.7%).

Step C: Synthesis of Intermediate Compound Int 1e

A stirred solution of Int 1d (6.2 kg, 25.00 mol) in dichloromethane (49.6 L) was treated with NEt₃ (7.6 kg, 75.00 mol). The resulting solution was treated with thionyl chloride (3.9 kg, 1.30 equivalents) dropwise with stirring at 25° C. over 3 hours. The resulting solution was stirred for 1 hour at 25° C. and then quenched by the addition of H₂O (15 L). The organic phase was washed with aqueous 10% NaHCO₃ (25 L) and then treated with aqueous NaOCl (124 L) and acetonitrile (6.2 L). The resulting mixture was stirred for an additional 48 hours at 15° C. and then quenched by the addition of aqueous Na₂SO₃ (45 L). The organic phase was washed with aqueous Na₂SO₃ (20 L) and brine (20 L). The organic phase was dried over anhydrous Na₂SO₄, filtered and concentrated in vacuo to provide Int 1e as a light brown liquid (4.5 kg, 58.5%).

Step D: Synthesis of Intermediate Compound Int 1f

To a solution of Int 1e (4.5 kg, 14.52 mol) in acetone (27.0 L) and water (9.0 L) was added NaN₃ (943.6 g, 14.52 mol). The resulting solution was stirred for 16 hours at 50° C. and then the reaction was cooled and diluted with ethyl acetate (50 L). The resulting mixture was treated with an aqueous solution of K₂HPO₄.3H₂O (5.1 kg in 45.0 L H₂O, 22.50 mol) and Bu₄NHSO₄ (5.2 kg, 15.25 mol). The resulting mixture was stirred for an additional 1 hour, and then extracted with ethyl acetate (20 L). The organic layer was dried over anhydrous Na₂SO₄, filtered and concentrated in vacuo resulting in Int 1f as a light yellow solid that was used in the next step without purification. (5.0 kg)

Step E: Synthesis of Intermediate Compound Int 1g

To a 50 L reactor were charged Int 1f (5.0 kg, 8.42 mol), HCl (36%, 1.5 L), and ethanol (25.0 L). The resulting solution was stirred for 5 hours at 83° C. and then was concentrated in vacuo. The pH value of the residual solution was adjusted to 7 with aqueous NaHCO₃ (10%). The resulting solution was extracted with ethyl acetate (30 L). The organic layer was dried over anhydrous Na₂SO₄, filtered and concentrated in vacuo. The residue was applied onto a silica gel column and eluted with ethyl acetate/hexane (1:1-6:1) to provide Int 1g as a white solid (1.1 kg, 40% for 2 steps).

Step F: Synthesis of Intermediate Compound Int 1h

To a stirred solution of Int 1 g (100 g, 534 mmol) in acetonitrile (500 mL) was added triethylamine (119 g, 1.17 mol) and DMAP (3.92 g, 32.1 mmol). The reaction was cooled to −10° C. and then treated with benzoyl chloride (136 mL, 1.17 mol) by additional funnel maintaining the reaction temperature below 20° C. After all starting material was consumed, the reaction was charged with water (3 L) and extracted with ethyl acetate (4×1 L). The combined organic layers were dried over Na₂SO₄, filtered and concentrated in vacuo. The white solid obtained (Int 1h) was used in the next step without purification (122.5 g, 58%).

Example 2

Preparation of Compound 2

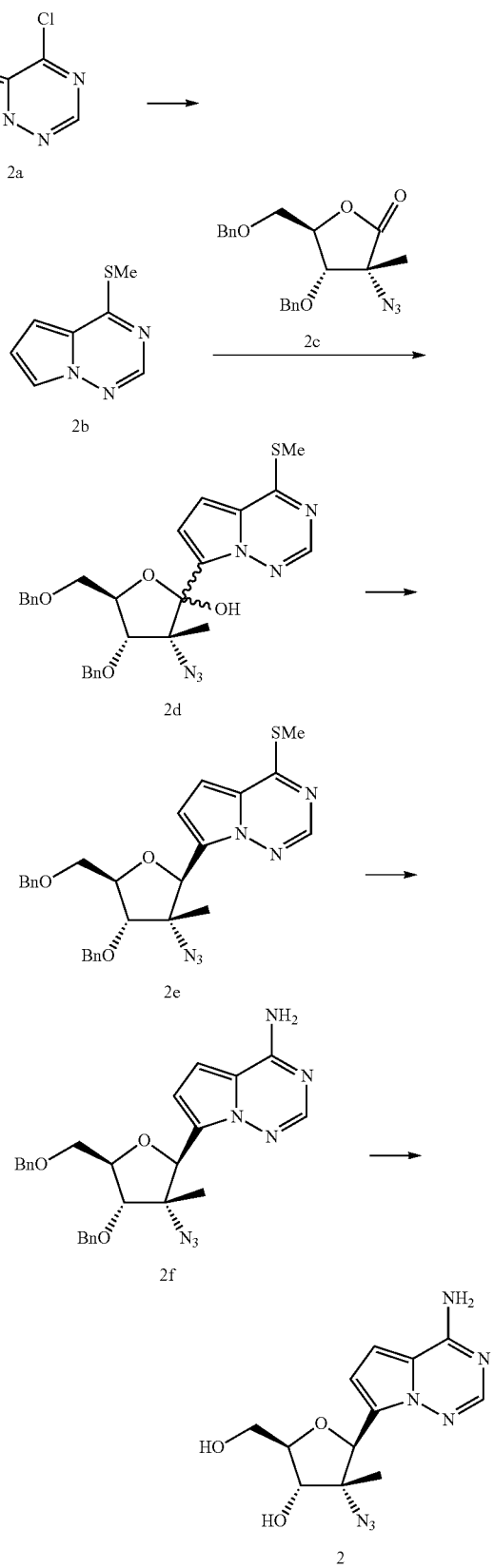

The synthesis of compound 2a can be found in WO2011/150356A1, 2011

Step A—Synthesis of Compound 2b

Into a 500-mL round-bottom flask, was placed a solution of 4-chloropyrrolo[2,1-f][1,2,4]triazine (17 g, 110.70 mmol) and (methylsulfanyl)sodium (15 g, 214.01 mmol) in tetrahydrofuran (300 mL). The resulting solution was stirred overnight at room temperature. The solids were filtered out. The resulting mixture was concentrated in vacuo. The residue was applied onto a silica gel column and eluted with ethyl acetate/petroleum ether (1:10). This resulted in 9 g (49%) of compound 2b as a yellow solid. LC-MS (ES, m/z): 166 [M+H]$^+$ Step B—Synthesis of Compound 2c Into a 250-mL round-bottom flask purged and maintained with an inert atmosphere of argon, was placed a solution of Int-1g (8.0 g, 42.78 mmol) in DMF (100 mL). This was followed by the addition of sodium hydride (3.4 g, 85.00 mmol), in portions at −25° C. in 15 minutes. The resulting solution was stirred for 30 minutes at −25° C., and then BnBr (16 g, 93.57 mmol) was added dropwise with stirring in 10 minutes. After the resulting solution was stirred for an additional 2 hours at 25° C., the reaction mixture was cooled down with an ice/salt bath. The pH value of the solution was adjusted to 7 with acetic acid. The residue was dissolved in ethyl aceatate, washed with H$_2$O, dried over anhydrous sodium sulfate and concentrated in vacuo. The residue was applied onto a silica gel column with ethyl acetate/petroleum ether (1:50-1:5) to give 14.0 g (90%) of compound 2c as light yellow oil. LC-MS: (ES, m/z): 368.2 [M+H]$^+$ Step C—Synthesis of Compound 2d Into a 500-mL round-bottom flask purged and maintained with an inert atmosphere of argon, was placed a solution of compound 2b (3 g, 18.16 mmol) in THF (80 mL). This was followed by the addition of LDA/THF (9.6 mL, 1.10 equivalents) dropwise with stirring at −78° C. After the resulting solution was stirred for 10 minutes at −78° C. in a liquid nitrogen bath, a solution of compound 2c (6 g, 16.33 mmol) in THF (70 mL) was added dropwise. The resulting solution was stirred for an additional 1 hour while the temperature was maintained at −78° C. in a liquid nitrogen bath. The reaction was then quenched by the addition of saturated NH$_4$Cl, extracted with ethyl acetate, dried over anhydrous Na$_2$SO$_4$ and concentrated in vacuo. The residue was applied onto a silica gel column and eluted with ethyl acetate/petroleum ether (1:2) to give 7.5 g (86%) of compound 2d as a white solid. LC-MS: (ES, m/z): 555.30 [M+Na]$^+$ Step D—Synthesis of Compound 2e Into a 250-mL round-bottom flask purged and maintained with an inert atmosphere of argon, was placed a solution of 2d (4.5 g, 8.45 mmol) and triethylsilane (2.95 g, 25.37 mmol) in DCM (100 mL). The resulting solution was stirred for 30 minutes at room temperature, then BF$_3$.OEt$_2$ was added (3.6 g, 3.00 equivalents) at 0° C. After the resulting solution was stirred for an additional 1.5 hours at room temperature, the reaction was quenched by the addition of 100 mL of saturated sodium bicarbonate. The resulting solution was extracted with dichloromethane, dried over anhydrous Na$_2$SO$_4$ and concentrated in vacuo. The residue was applied onto a silica gel column and eluted with ethyl acetate/petroleum ether (1:5) to give 4.3 g (89%) of compound 2e as a white solid. LC-MS: (ES, m/z): 517.0 [M+H]$^+$ Step E—Synthesis of Compound 2f Into a 100-mL sealed tube, was placed compound 2e (4 g, 7.74 mmol), ammonia (70 mL) in NH$_3$(l)/propan-2-ol (10 mL). After the resulting solution was stirred overnight at 80° C. in an oil bath, it was concentrated in vacuo. The residue was applied onto a silica gel column and eluted with dichloromethane/methanol (15:1) to give 3.2 g (80%) of compound 2f as a white solid. LC-MS: (ES, m/z): 486.2 [M+H]$^+$ Step F—Synthesis of Compound 2

Into a 50-mL round-bottom flask purged and maintained with an inert atmosphere of argon, was placed a solution of compound 2f (200 mg, 0.41 mmol) in DCM (10.0 mL). This was followed by the addition of BCl$_3$/CH$_2$Cl$_2$ (1.65 mL, 4.00 equivalents) at −78° C. After the resulting solution was stirred for 1 hour at −40° C. in a liquid nitrogen bath, the reaction was quenched by the addition of 30 mL of saturated sodium bicarbonate. The pH value of the solution was adjusted to 7. The resulting solution was extracted with dichloromethane, dried over anhydrous sodium sulfate and concentrated in vacuo. The residue was applied onto a silica gel column and eluted with dichloromethane/methanol (10:1) to give 40 mg (32%) of compound 2 as a white solid. LC-MS: (ES, m/z): 306.05 [M+H]$^+$, $^1$H-NMR: (300 MHz, CD$_3$OD, ppm): δ 7.81 (s, 1H), 6.88 (d, J=4.5, 1H), 6.82 (d, J=4.5, 1H), 5.55 (s, 1H), 4.07-4.10 (m, 1H), 3.91-3.98 (m, 2H), 3.77-3.82 (m, 1H), 1.09 (s, 3H).

The following compounds of the present invention were made using the methods described in the Example above and substituting the appropriate reactants and/or reagents.

| Compd # | Structure | Starting Material | LC-MS or MS (M + H) |
|---|---|---|---|
| 3 | (structure shown) | Int-1g | 307 |
| 4 | (structure shown) | Int-1g | 307 |

Example 3

Preparation of Compound 5

Step A—Synthesis of Compound 5

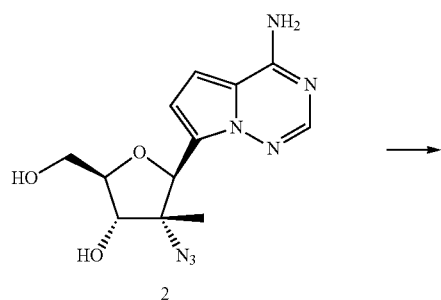

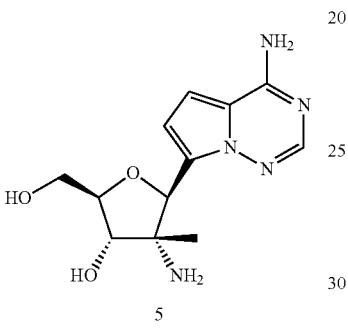

Into a 50-mL round-bottom flask, was placed a solution of compound 2 (20 mg, 0.07 mmol) in ethanol (10 mL), Palladium carbon (10 mg). The resulting mixture was stirred for 2 hours at room temperature under $H_2$. The solids were filtered out and the filtrate was concentrated in vacuo. The crude product (10 mg) was purified by Prep-HPLC with the following conditions (1#-Pre-HPLC-011(Waters)): Column, Atlantis Prep OBD $T_3$ Column, 19*150 mm, 5 um; mobile phase, Water with 10 mmol $NH_4HCO_3$ and $CH_3CN$ (1.0% $CH_3CN$ up to 19.0% in 6 min, up to 95.0% in 1 min, down to 1.0% in 1 min); Detector, UV 254 & 220 nm. This resulted in 4.3 mg (24%) of compound 5 as a white solid. LC-MS: (ES, m/z): 280.1 [M+H]$^+$, $^1$H-NMR: (300 MHz, $CD_3OD$, ppm): δ 7.79 (s, 1H), 6.89 (d, J=4.2, 1H), 6.82 (d, J=4.2, 1H), 5.42 (s, 1H), 3.88-3.96 (m, 2H), 3.77-3.83 (m, 2H), 0.90 (s, 3H).

The following compounds of the present invention were made using the methods described in the Example above and substituting the appropriate reactants and/or reagents.

| Compd # | Structure | Starting Material | LC-MS or MS (M + H) |
|---|---|---|---|
| 6 | 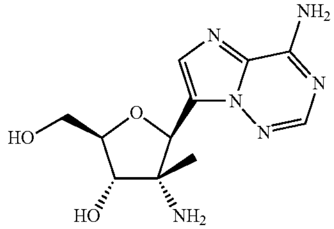 [SMILES: C[C@@]1(N)[C@H](O)[C@@H](CO)O[C@H]1c1cnc2c(N)ncnn12] | Compound 3 | 281 |
| 7 | | Compound 4 | 281 |

Example 4

Preparation of Compound 8

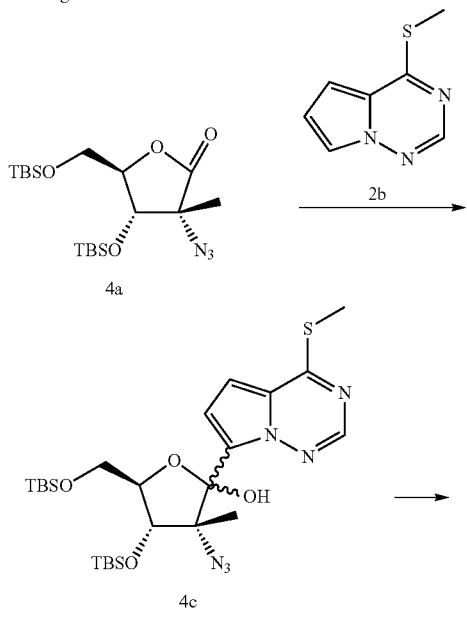

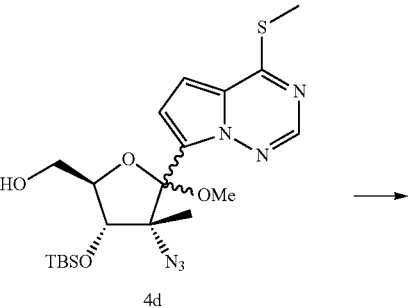

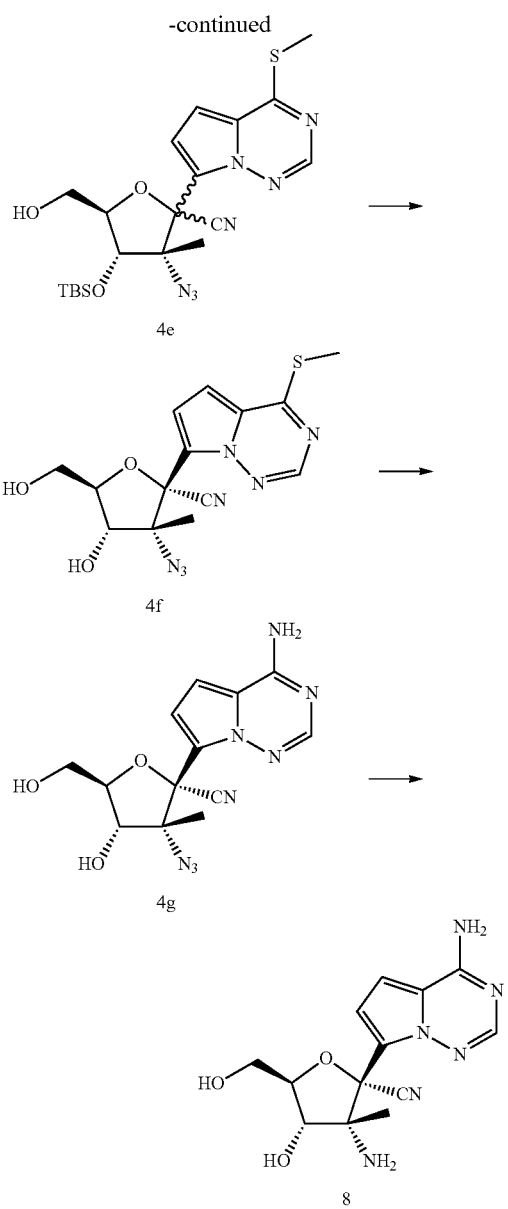

Step A—Synthesis of Compound 4a

Into a 250-mL round-bottom flask purged and maintained with an inert atmosphere of argon, was placed a solution of Int-1g (5 g, 26.72 mmol) and imidazole (9.1 g, 5.00 equivalents) in DMF (5 mL). Then tert-butyl(chloro)dimethylsilane (24.2 g, 160.56 mmol) was added. After the resulting solution was stirred overnight at 50° C., it was diluted with ethyl acetate, washed with water, brine, dried over anhydrous sodium sulfate and concentrated in vacuo. The residue was applied onto a silica gel column and eluted with ethyl acetate/petroleum ether (1/30) to give 10 g (90%) of compound 4a as colorless oil. LC-MS: (ES, m/z): 416.6 [M+H]$^+$ Step B—Synthesis of Compound 4c Into a 500-mL 3-necked round-bottom flask purged and maintained with an inert atmosphere of argon, was placed a solution of 2b (4.97 g, 30.12 mmol) in THF (100 mL). This was followed by the addition of LDA (22.5 mL, 1.50 equiv, 2 mol/L) dropwise with stirring at −78° C. After the resulting solution was stirred for 15 minutes at −78° C., a solution of compound 4a (15.0 g, 36.14 mmol) in THF (50 mL) was added dropwise with stirring at −78° C. The resulting solution was stirred for an additional 30 minutes at −78° C. and then quenched by the addition of saturated NH$_4$Cl. The resulting solution was extracted with dichloromethane, dried over anhydrous sodium sulfate and concentrated in vacuo. The residue was applied to a silica-gel column and eluted with ethyl acetate/petroleum ether (1/20) to give 10 g (57%) of compound 4c as a solid. LC-MS: (ES, m/z): 481.1, [M+H]$^+$ Step C—Synthesis of Compound 4d Into a 500-mL 3-necked round-bottom flask purged and maintained with an inert atmosphere of argon, was placed a solution of compound 4c (10 g, 17.24 mmol) in methanol (200 ml). This was followed by the addition of sulfuric acid (1.7 g, 17.35 mmol) dropwise with stirring at 5-10° C. The resulting solution was stirred for 1 hour at 5-10° C. in a water/ice bath. The pH value of the solution was adjusted to 7 with triethylamine, and then concentrated in vacuo. The residue was diluted with DCM, washed with water, dried over anhydrous sodium sulfate and concentrated in vacuo to give 6.0 g (73%) of compound 4d as a white solid, which was used for the next reaction directly. LC-MS: (ES, m/z): 486.1, [M+H]$^+$ Step D—Synthesis of Compound 4e Into a 500-mL 3-necked round-bottom flask purged and maintained with an inert atmosphere of argon, was placed a solution of compound 4d (5.0 g, 10.42 mmol) and trimethylsilanecarbonitrile (5.15 g, 52.02 mmol) in DCM (100 ml). After the resulting solution was stirred for 30 minutes at 0° C., BF$_3$Et$_2$O (2.2 g, 15.49 mmol) was added dropwise with stirring at 0° C. The resulting solution was stirred for 10 minutes at 0° C. The pH value of the solution was adjusted to 7 with triethylamine. The reaction was then quenched by the addition of saturated sodium bicarbonate and diluted with DCM. The resulting mixture was washed with water, dried over anhydrous sodium sulfate and concentrated in vacuo to give 2.5 g (51%) of compound 4e as a white solid, which was used for the next reaction directly. LC-MS: (ES, m/z): 476.1, [M+H]$^+$ Step E—Synthesis of Compound 4f Into a 250-mL round-bottom flask purged and maintained with an inert atmosphere of argon, was placed a solution of compound 4e (3.0 g, 6.32 mmol) and TBAF (3.3 g, 12.64 mmol) in THF (50 ml). The resulting solution was stirred for 30 minutes at room temperature, and then concentrated in vacuo. The residue was applied onto a silica gel column and eluted with ethyl acetate/petroleum ether (1:1) to give 1.8 g (79%) of compound 4f as a light yellow solid. LC-MS: (ES, m/z): 362.0 [M+H]$^+$ Step F—Synthesis of Compound 4g Into a 10-mL sealed tube, was placed a solution of compound 4f (1.0 g, 2.77 mmol) in NH$_3$/i-PrOH (9 mL). After the resulting solution was stirred overnight at 60° C. in an oil bath, it was concentrated in vacuo. The residue was applied onto a silica gel column and eluted with dichloromethane/methanol (10:1) to give 600 mg (66%) of compound 4g as a white solid. LC-MS: (ES, m/z): 331.0 [M+H]+

Step G—Synthesis of Compound 8

Into a 50-mL round-bottom flask, was placed a solution of compound 4g (23.1 mg, 0.07 mmol) in ethanol (10 mL), 10% palladium carbon (10 mg). The resulting mixture was stirred for 2 hours at room temperature under $H_2$. The solids were filtered out and the filtrate was concentrated in vacuo. The crude product (10 mg) was purified by Prep-HPLC with the following conditions (1#-Pre-HPLC-011(Waters)): Column, Atlantis Prep OBD $T_3$ Column, 19*150 mm, 5 um; mobile phase, Water with 10 mmol $NH_4HCO_3$ and $CH_3CN$ (1.0% $CH_3CN$ up to 19.0% in 6 min, up to 95.0% in 1 min, down to 1.0% in 1 min); Detector, UV 254 & 220 nm. This resulted in 8.5 mg (40%) of compound 8 as a white solid. LC-MS: (ES, m/z): 305.2 [M+H]+ 1H-NMR: (400 MHz, $CD_3OD$, ppm): δ7.92 (s, 1H), 6.93 (d, J=4.4 Hz, 1H), 6.90 (d, J=4.8 Hz, 1H), 4.24-4.26 (m, 1H), 3.91-3.98 (m, 1H), 3.81-3.84 (m, 2H), 0.83 (s, 3H).

Example 5

Preparation of Compound 9

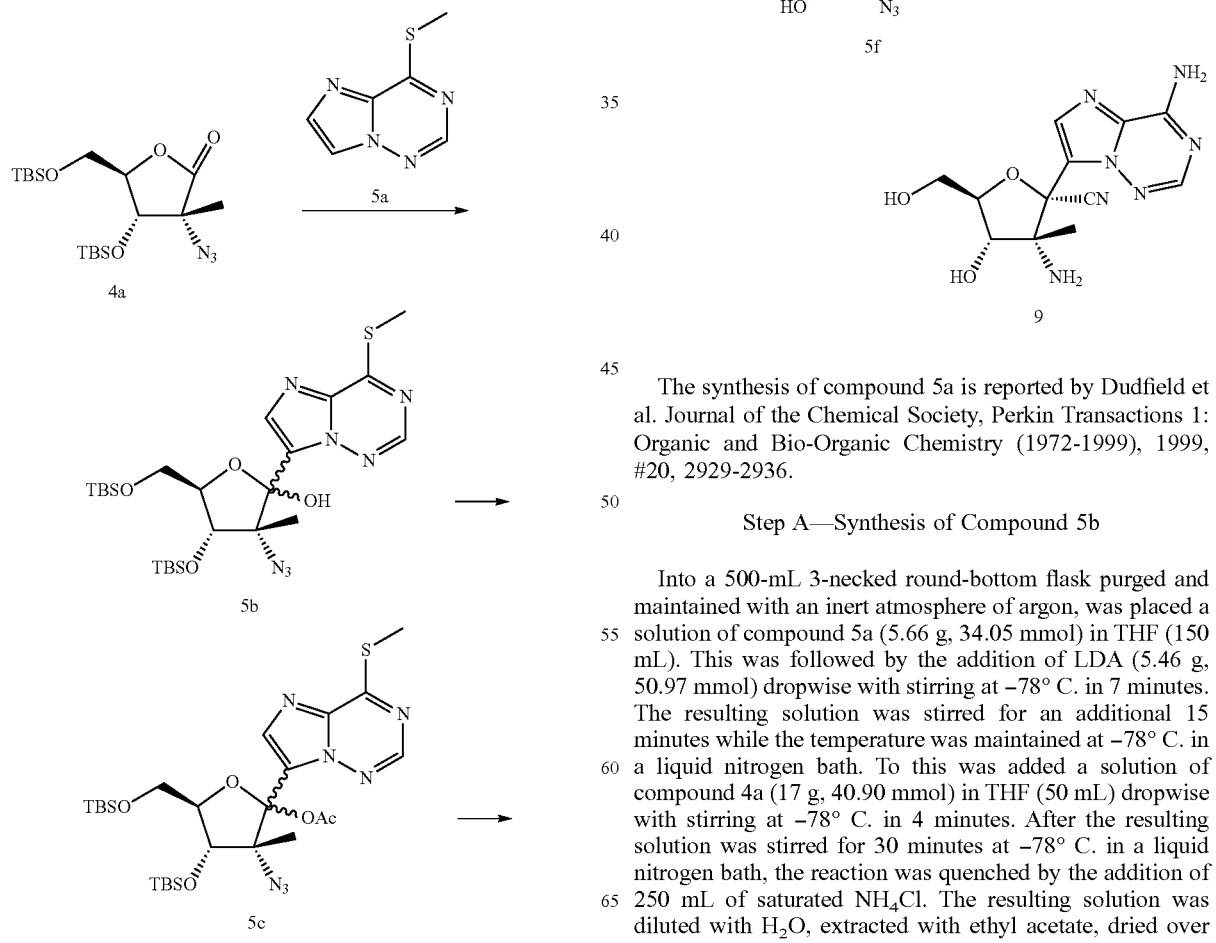

The synthesis of compound 5a is reported by Dudfield et al. Journal of the Chemical Society, Perkin Transactions 1: Organic and Bio-Organic Chemistry (1972-1999), 1999, #20, 2929-2936.

Step A—Synthesis of Compound 5b

Into a 500-mL 3-necked round-bottom flask purged and maintained with an inert atmosphere of argon, was placed a solution of compound 5a (5.66 g, 34.05 mmol) in THF (150 mL). This was followed by the addition of LDA (5.46 g, 50.97 mmol) dropwise with stirring at −78° C. in 7 minutes. The resulting solution was stirred for an additional 15 minutes while the temperature was maintained at −78° C. in a liquid nitrogen bath. To this was added a solution of compound 4a (17 g, 40.90 mmol) in THF (50 mL) dropwise with stirring at −78° C. in 4 minutes. After the resulting solution was stirred for 30 minutes at −78° C. in a liquid nitrogen bath, the reaction was quenched by the addition of 250 mL of saturated $NH_4Cl$. The resulting solution was diluted with $H_2O$, extracted with ethyl acetate, dried over anhydrous sodium sulfate and concentrated in vacuo. The residue was applied onto a silica gel column and eluted with ethyl acetate/petroleum ether (1:50-1:5) to give 9 g (45%) of compound 5b as a white solid. LC-MS: (ES, m/z): 582.6 [M+H]⁺

Step B—Synthesis of Compound 5c

Into a 500-mL 3-necked round-bottom flask purged and maintained with an inert atmosphere of argon, was placed a solution of compound 5b (30 g, 51.56 mmol) and 4-dimethylaminopyridine (3.12 g, 25.54 mmol) in pyridine (300 mL). This was followed by the addition of Ac₂O (30 mL) dropwise with stirring at 25° C. in 5 minutes. After the resulting solution was stirred for 2 hours at 50° C. in an oil bath, it was concentrated in vacuo. The residue was applied onto a silica gel column and eluted with ethyl acetate/petroleum ether (1:50-1:5) to give 32 g (99%) of compound 5c as a white solid. LC-MS: (ES, m/z): 624.2 [M+H]⁺, ¹H-NMR: (300 MHz, CDCl₃, ppm): δ8.40 (s, 1H), 7.85 (s, 1H), 4.66-4.64 (m, 1H), 4.31-4.27 (m, 1H), 4.07-4.02 (d, J=15 Hz, 1H), 3.80-3.75 (d, J=15 Hz, 1H), 2.70 (s, 3H), 2.08 (s, 3H), 1.68 (s, 3H), 0.93 (m, 18H), 0.23-0.15 (m, 12H)

Step C—Synthesis of Compound 5d

Into a 500-mL 3-necked round-bottom flask purged and maintained with an inert atmosphere of argon, was placed a solution of compound 5c (9.2 g, 14.75 mmol) in DCM (200 mL). This was followed by the addition of TMSCN (17.86 g, 12.00 equivalents) dropwise with stirring at 0° C. in 5 minutes and then BF₃Et₂O (6.3 g, 3.00 equivalents) dropwise with stirring at 0° C. in 10 minutes. The resulting mixture was stirred for 1 hour at 0° C., and then quenched by the addition of saturated NH₄Cl. The resulting solution was diluted with of DCM, washed with brine, dried over anhydrous sodium sulfate and concentrated in vacuo. The residue was applied onto a silica gel column and eluted with EA/PE (1:50-1:5) to give 7.5 g (86%) of compound 5d as a white solid. LC-MS: (ES, m/z): 591.3 [M+H]⁺

Step D—Synthesis of Compound 5e

Into a 250-mL round-bottom flask purged and maintained with an inert atmosphere of argon, was placed a solution of compound 5d (7.5 g, 12.69 mmol) and TBAF (6.65 g, 25.43 mmol, 2.00 equiv) in THF (80 mL). The resulting solution was stirred for 0.5 hours at 25° C. and then concentrated in vacuo. The residue was applied onto a silica gel column and eluted with ethyl acetate:petroleum ether (1:50-2:1) to give 1.5 g (33%) of compound 5e as a white solid. LC-MS: (ES, m/z): 363.0 [M+H]⁺, ¹H-NMR (400 MHz, CDCl₃, ppm): δ8.62 (s, 1H), 8.08 (s, 1H), 4.33-4.25 (m, 2H), 4.21-4.09 (m, 1H), 4.00-3.92 (d, J=32 Hz, 1H), 2.76 (s, 3H), 1.56 (s, 3H).

Step E—Synthesis of Compound 5f

Into a 80-mL sealed tube purged and maintained with an inert atmosphere of argon, was placed compound 5e (1.5 g, 4.14 mmol). This was followed by the addition of NH₃/i-PrOH (80 mL) at −78° C. in a liquid nitrogen bath. The resulting solution was stirred for 5 hours at 40° C. in an oil bath and then concentrated in vacuo. The residue was applied onto a silica gel column and eluted with ethyl acetate/petroleum ether (1:10-2:1) to give 500 mg (36%) of compound 5f as a white solid. LC-MS (ES, m/z): 332.2 [M+H]⁺

Step F—Synthesis of Compound 9

Into a 50-mL round-bottom flask purged and maintained with an inert atmosphere of argon, was placed a solution of 5f (340 mg, 1.03 mmol) and PPh₃ (457 mg, 1.74 mmol) in methanol/H₂O (5:1) (20 mL). After the resulting solution was stirred for 4 hours at 50° C. in an oil bath, it was concentrated in vacuo. The residue was applied onto a silica gel column and eluted with dichloromethane/methanol (50:1-5:1) to give 260 mg (83%) of compound 9 as a white solid. LC-MS: (ES, m/z): 306.2 [M+H]⁺, ¹H-NMR: (300 MHz, DMSO, ppm): δ8.43 (s, 1H), 8.34 (s, 1H), 8.18 (s, 1H), 7.70 (S, 1H), 5.85 (d, J=4.5 Hz, 1H), 5.09-5.03 (m, 1H), 4.09 (s, 1H), 3.83-3.72 (m, 2H) 3.68-3.61 (m, 1H), 0.78 (s, 3H).

Example 6

Preparation of Compound 10

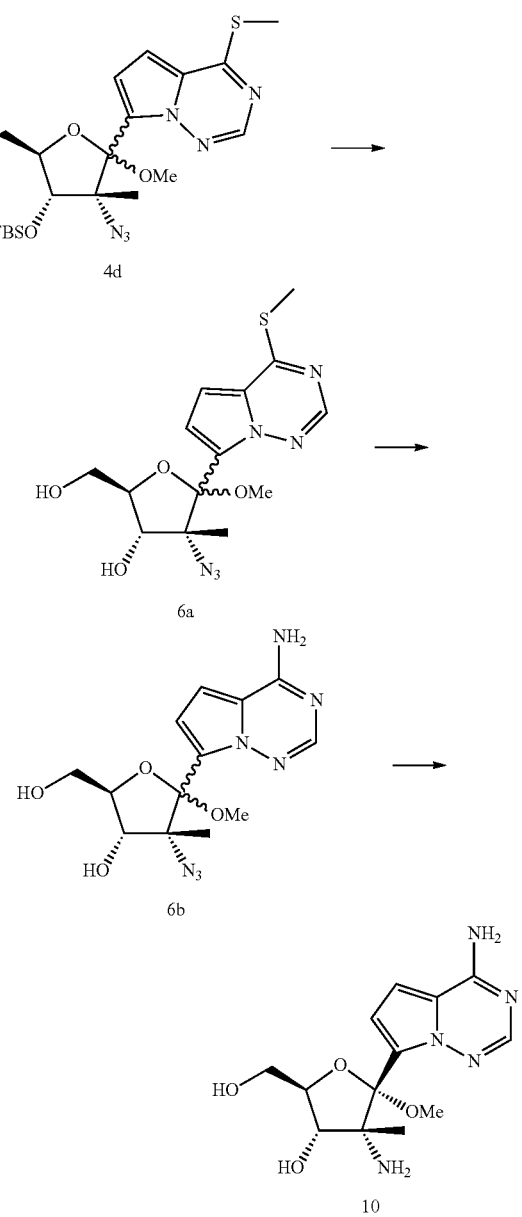

Step A—Synthesis of Compound 6a

Into a 250-mL round-bottom flask purged and maintained with an inert atmosphere of argon, was placed a solution of 4d (1.6 g, 3.33 mmol) and TBAF (1.74 g, 6.67 mmol) in THF (120 ml). After the resulting solution was stirred for 1 hour at room temperature, it was concentrated in vacuo. The residue was applied onto a silica gel column and eluted with ethyl acetate/petroleum ether (1:1) to give 1.0 g (82%) of compound 6a as a white solid. LC-MS: (ES, m/z): 367.2 [M+H]+

Step B—Synthesis of Compound 6b

Into a 80-mL sealed tube, was placed a solution of compound 6a (1.3 g, 3.55 mmol) in NH$_3$/i-PrOH (70 mL). After the resulting solution was stirred overnight at 80° C. in an oil bath, it was concentrated in vacuo. The crude product was purified by re-crystallization from methanol to give 800 mg (67%) of compound 6b as a white solid. LC-MS: (ES, m/z): 336.2[M+H]+

Step C—Synthesis of Compound 10

Into a 50-mL round-bottom flask, was placed a solution of compound 6b (23.5 mg, 0.07 mmol) and palladium/carbon (10 mg) in ethanol (10 mL). The resulting mixture was stirred for 2 hours at room temperature under H$_2$. The solids were filtered out and the filtrate was concentrated in vacuo. The crude product (10 mg) was purified by Prep-HPLC with the following conditions (1#-Pre-HPLC-011(Waters)): Column, Atlantis Prep OBD T$_3$ Column, 19*150 mm, 5 um; mobile phase, Water with 10 mmol NH$_4$HCO$_3$ and CH$_3$CN (1.0% CH$_3$CN up to 19.0% in 6 min, up to 95.0% in 1 min, down to 1.0% in 1 min); Detector, UV 254 & 220 nm. This resulted in 10.8 mg (40%) of compound 10 as a white solid. LC-MS: (ES, m/z): 310.1[M+H]+, $^1$H-NMR: (400 MHz, CD$_3$OD, ppm): δ7.79 (s, 1H), 6.80-6.92 (m, 2H), 4.00-4.07 (m, 2H), 3.80-3.85 (m, 1H), 3.67-3.79 (m, 1H), 3.23 (s, 3H), 1.38 (s, 3H).

Example 7

Preparation of Compound 11

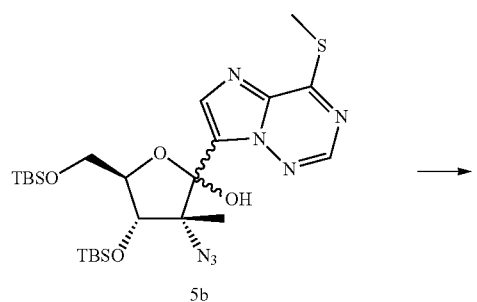

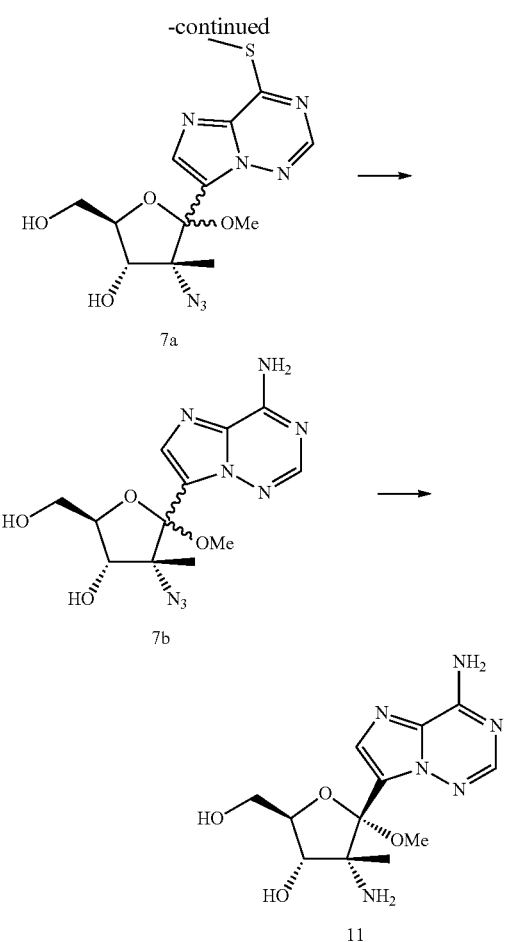

Step A—Synthesis of Compound 7a

Into a 25-mL 3-necked round-bottom flask purged and maintained with an inert atmosphere of argon, was placed a solution of compound 5b (1.0 g, 1.72 mmol) in methanol (10 mL). This was followed by the addition of sulfuric acid (0.4 mL) dropwise with stirring at 0-5° C. in 2 minutes. The resulting solution was stirred overnight at 25° C. The pH value of the solution was adjusted to 7 with TEA. The resulting mixture was concentrated in vacuo and the residue was applied onto a silica gel column and eluted with dichloromethane/methanol (50:1-5:1) to give 250 mg (40%) of compound 7a as a white solid. LC-MS: (ES, m/z): 368.2[M+H]+

Step B—Synthesis of Compound 7b

Into a 10-mL sealed tube, was placed compound 7a (200 mg, 0.54 mmol). This was followed by the addition of NH$_3$/i-PrOH (10 mL) at −78° C. in a liquid nitrogen bath. The resulting solution was stirred for 5 hours at 40° C. in an oil bath and then concentrated in vacuo. The residue was applied onto a silica gel column and eluted with dichloromethane/methanol (50:1-5:1) to give 150 mg (82%) of compound 7b as a white solid. LC-MS: (ES, m/z): 337.2 [M+H]+

Step C—Synthesis of Compound 11

Into a 50-mL round-bottom flask (1 atm) purged and maintained with an inert atmosphere of $H_2$, was placed compound 7b (50 mg, 0.11 mmol), 10% palladium/carbon (10 mg), and methanol (20 mL). After the resulting solution was stirred for 0.5 hours at room temperature, the solids were filtered out and the filtrate was concentrated in vacuo. The crude product was purified by Flash-Prep-HPLC to give 20 mg (52%) of compound 11 as a white solid. LC-MS (ES, m/z): 333.3 [M+Na]+, $^1$H-NMR: (400 MHz, MeOD, ppm): δ8.12 (s, 1H), 7.69 (s, 1H), 4.13-4.15 (m, 1H), 4.03-4.09 (m, 1H), 3.83-3.89 (m, 1H), 3.59-3.72 (m, 1H), 3.5 (s, 3H), 1.39 (s, 3H).

Example 8

Preparation of Compound 12 and 13

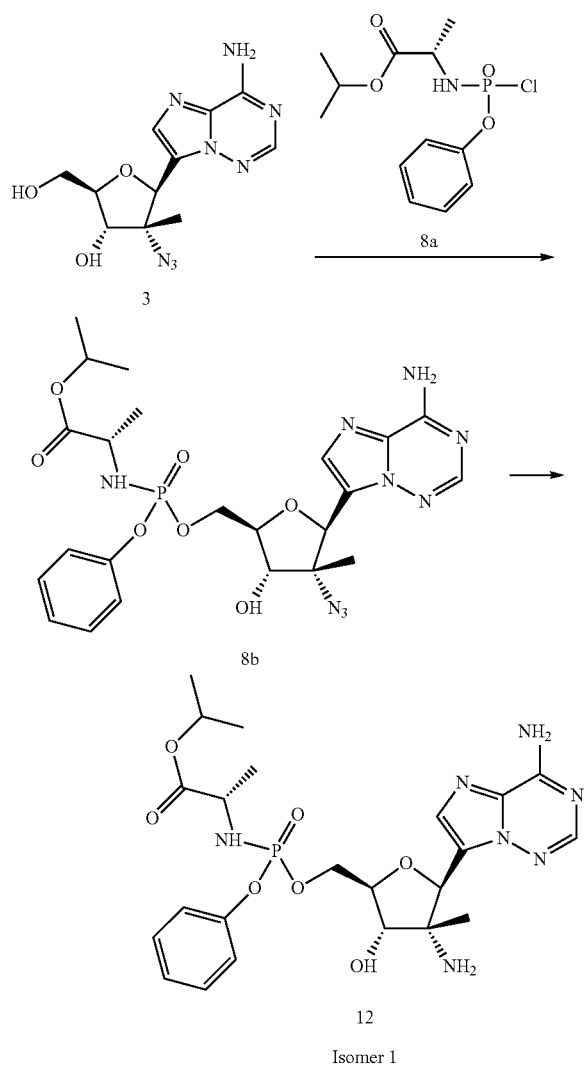

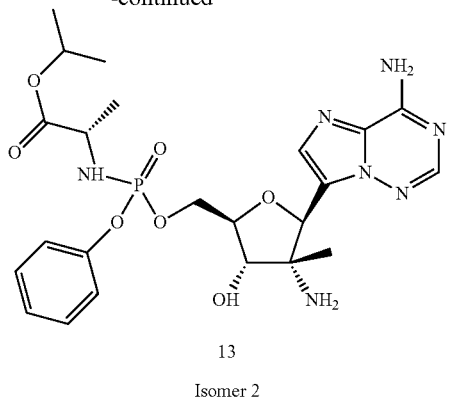

Phosphorylamino chloride reactants of type 8a can be made using the methods described in U.S. Pat. No. 7,879,815.

Step A—Synthesis of Compound 8b

Into a 100-mL round-bottom flask purged and maintained with an inert atmosphere of argon, was placed a solution of compound 3 (500 mg, 1.63 mmol) and compound 8a (548 mg, 1.79 mmol) in DMF (10 mL). This was followed by the addition of tert-butyl(chloro)magnesium (1.06 mL, 1.10 equivalents) dropwise with stirring at −40° C. in 10 minutes. After the resulting solution was stirred for 1.5 hour from −40° C. to room temperature, the reaction was quenched by the addition of saturated ammonium chloride (0.5 mL). The resulting solution was extracted with dichloromethane. The combined organic layers were dried over sodium sulfate and concentrated in vacuo. The residue was applied onto a silica gel column and eluted with dichloromethane/methanol (8:1) to give 500 mg (mixture of two isomers at phosphorus) of compound 8b as a white solid.

Step B—Synthesis of Compounds 12 and 13

Into a 50-mL round-bottom flask, was placed a mixture of compound 8b (500 mg) and Pd(OH)$_2$/C (250 mg) in ethyl acetate/ethanol (1:1, v/v, 10 mL). After the resulting solution was stirred overnight at room temperature under $H_2$ atmosphere, the solids were filtered out and the filtrate was concentrated in vacuo. The residue was applied onto a silica gel column and eluted with dichloromethane/methanol (8:1). The crude product (250 mg) was purified by Prep-HPLC with the following conditions (1#-Pre-HPLC-001(SHIMADZU)): Column, SunFire Prep C18 OBD Column, 5 um, 19*150 mm; mobile phase, water. This resulted in 122 mg of compound 12 (isomer 1) and 130 mg of compound 13 (isomer 2) as white solids. LC-MS 12 (ES, m/z): 550.1 [M+H]+, $^1$H-NMR 12: (400 MHz, MeOD, ppm): δ8.08 (s, 1H), 7.64 (s, 1H), 7.36 (t, J=8.0 Hz, 2H), 7.27 (d, J=8.8 Hz, 2H), 7.19 (t, J=7.2 Hz, 1H), 5.38 (s, 1H), 5.00 (m, 1H), 4.50 (m, 1H), 4.39 (m, 1H), 4.12 (d, J=1.6 Hz, 1H), 3.96 (m, 2H), 1.33 (d, J=7.2 Hz, 3H), 1.24 (dd, J=6.4, 1.6 Hz, 6H), 0.95 (s, 3H).

The following compounds of the present invention were made using the methods described in the Example above and substituting the appropriate reactants and/or reagents.

| Compd # | Structure | Starting Material | LC-MS or MS (M + H) |
|---|---|---|---|
| 14 | 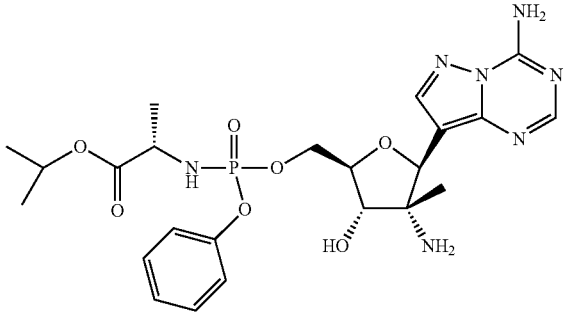 [SMILES: CC(C)OC(=O)[C@H](C)NP(=O)(OC[C@H]1O[C@@H](c2cnn3c(N)ncnc23)[C@](C)(N)[C@@H]1O)Oc1ccccc1] | Compound 4 | 550 |
| 15 | 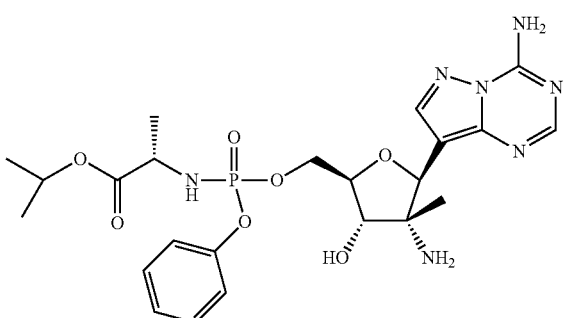 | Compound 4 | 550 |

Example 9

Preparation of Compound 16 and 17

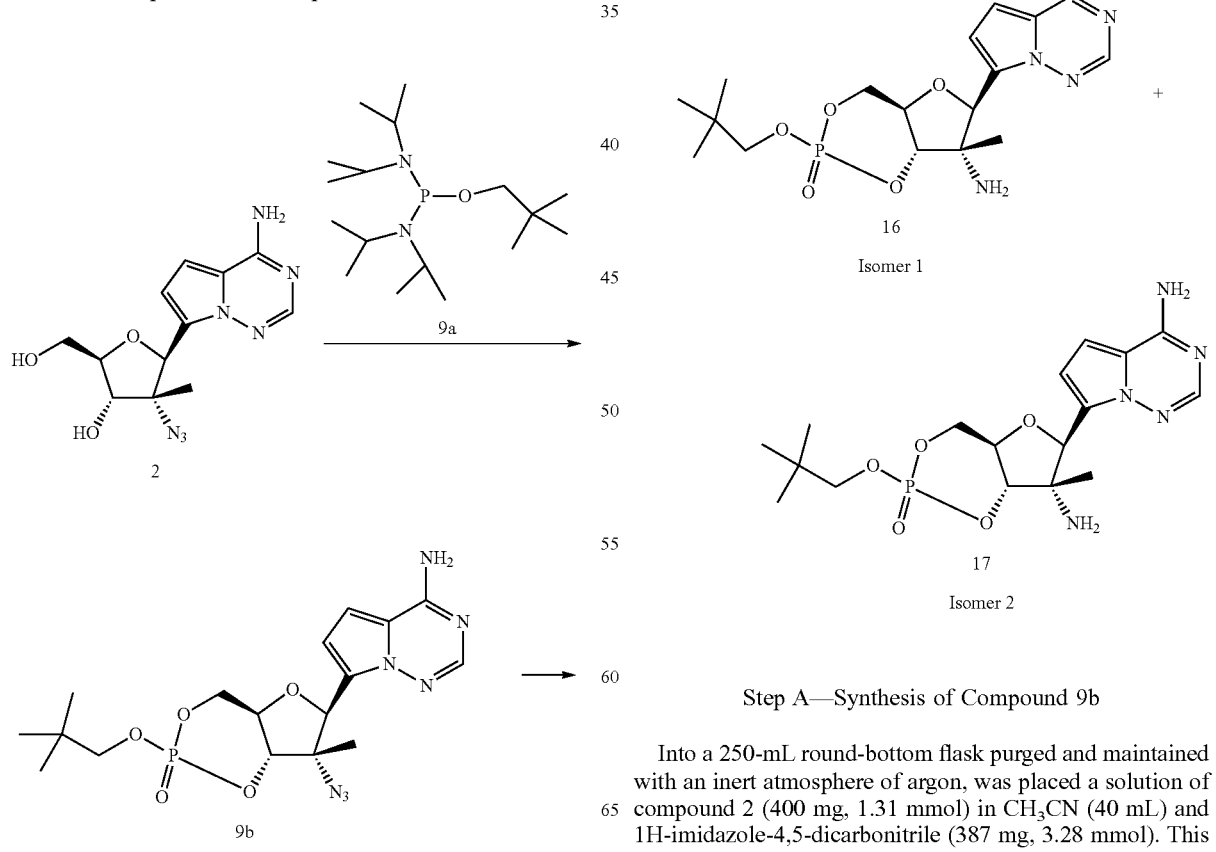

Step A—Synthesis of Compound 9b

Into a 250-mL round-bottom flask purged and maintained with an inert atmosphere of argon, was placed a solution of compound 2 (400 mg, 1.31 mmol) in $CH_3CN$ (40 mL) and 1H-imidazole-4,5-dicarbonitrile (387 mg, 3.28 mmol). This was followed by the addition of a solution of compound 9a (542 mg, 1.70 mmol, 1.30 equiv) in THF (15 mL) dropwise with stirring at 0° C. in 5 minutes. After the resulting solution was stirred for 16 hours at 28° C., it was concentrated in vacuo. The residue was dissolved in THF/Py/H$_2$O (78/20/2) (5 mL) and 1M I$_2$ in THF/Py/H$_2$O (78/20/2) was added. The resulting solution was stirred at 0° C. for 20 minutes and then the reaction was concentrated under vacuum. The residue was applied onto a silica gel column and eluted with dichloromethane/methanol (100:1-20:1) to give 100 mg (17%) of compound 9b as a white solid (mixture of two isomers at P). LC-MS: (ES, m/z): 438.1 [M+H]$^+$ Step B—Synthesis of Compounds 16 and 17

Into a 150-mL round-bottom flask, was placed a solution of compound 9b (100 mg, 0.23 mmol) in ethanol (40 mL). Pd(OH)$_2$/C (20 mg, 0.14 mmol, 0.62 equiv) was added and the resulting solution was stirred for 3 hours at 25° C. under hydrogen. After the reaction finished, the solids were filtered out and the filtrate was concentrated in vacuo. The crude product (95 mg) was purified by Prep-HPLC with the following conditions (1#-Pre-HPLC-011(Waters)): Column, SunFire Prep C18, 19*150 mm Sum; mobile phase, water and acetonitrile (20.0% acetonitrile up to 79.0% in 8 min, up to 100.0% in 1 min, down to 20.0% in 1 min); Detector, UV 254 & 220 nm. This resulted in 22 mg (22%) of compound 16 as a white solid and 33 mg (33%) of compound 17 as a white solid. LC-MS 16: (ES, m/z): 412.0 [M+1-1]$^+$, $^1$H-NMR 16: (CD$_3$OD, ppm): δ7.84 (s, 1H), 6.90 (d, J=4.4 Hz, 1H), 6.67 (d, J=4.4 Hz, 1H), 5.56 (s, 1H), 4.88-4.71 (m, 1H), 4.66-4.57 (m, 2H), 4.52-4.48 (m, 1H), 3.93-3.85 (m, 2H), 1.01 (s, 9H), 0.97 (s, 3H). P-NMR (CD$_3$OD, ppm): δ −2.96 (s).

The following compounds of the present invention were made using the methods described in the Example above and substituting the appropriate reactants and/or reagents.

| Compd # | Structure | Starting Material | LC-MS or MS (M + H) |
| --- | --- | --- | --- |
| 18 | 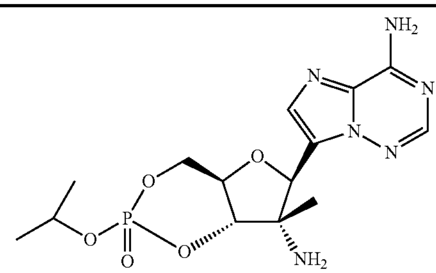 | Compound 3 | 385 |
| 19 | 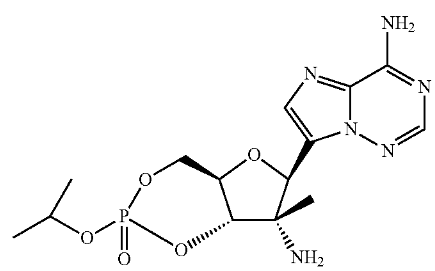 | Compound 83 | 385 |
| 20 | 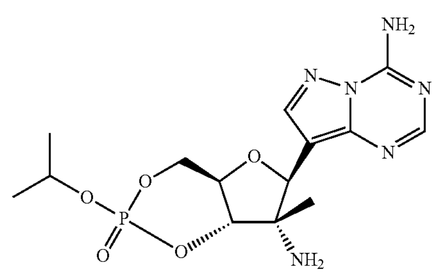 | Compound 4 | 385 |
| 21 | 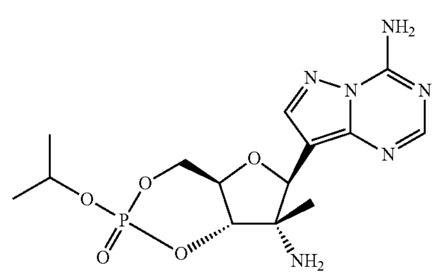 | Compound 4 | 385 |

Example 10

Preparation of Compound 22 and 23

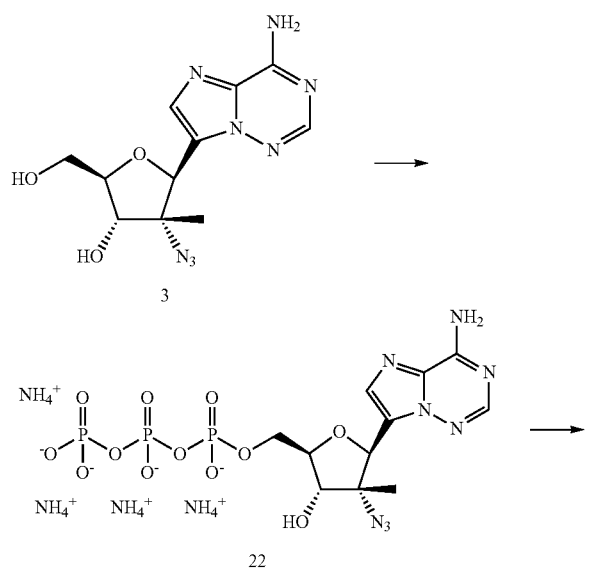

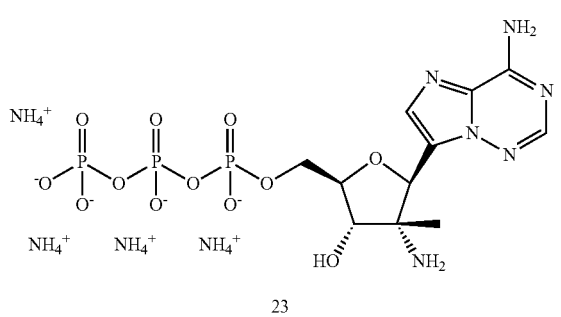

Step A—Synthesis of Compound 22

Into a 10-mL round-bottom flask purged and maintained with an inert atmosphere of argon, was placed a solution of compound 3 (30.6 mg, 0.10 mmol) and proton sponge (42.8 mg, 0.20 mmol) in trimethyl phosphate (1.5 mL). The resulting solution was stirred for 0.5 hours at room temperature, and then phosphoryl chloride (30.6 mg, 0.20 mmol) was added dropwise with stirring at 0° C. After 1 hour at 0° C., a solution of pyrophosphate (345.2 mg, 0.63 mmol) in N,N-dimethylformamide (1 mL) and tributylamine (92.8 mg, 0.50 mmol) was added. The resulting solution was stirred for 40 minutes at 0° C., and then quenched by the addition of 5 ml of 1M triethylammonium bicarbonate buffer. After the resulting solution was stirred for additional 0.5 hours at room temperature, it was concentrated in vacuo. The combined residue was chromatographed on Sephadex DEAE A-25($HCO_3^-$) column, eluted gradiently with 0-2.0 M triethylammonium bicarbonate buffer, the collected fractions were concentrated in vacuo. The crude product (50 mg) was purified by Prep-HPLC with the following conditions (1#-Pre-HPLC-011(Waters)): Column, Atlantis Prep OBD T3 Column, 19*150 mm, 5 um; mobile phase, water with 50 mL ammonium bicarbonate and acetonitrile (1% acetonitrile up to 10% in 9.5 min, up to 95% in 1.5 min, down to 1% in 1.5 min); Detector, UV 254 & 220 nm. This resulted in 11.8 mg (19%) of compound 22 as a white solid. LC-MS: (ES, m/z): 545.0 [M–H]$^-$, $^1$H-NMR: (300 MHz, $D_2O$, ppm): δ8.03 (s, 1H), 7.75 (s, 1H), 5.44 (s, 1H), 4.11-4.34 (m, 4H), 1.14-1.24 (m, 3H) P-NMR: (121 MHz, $D_2O$, ppm): δ −6.21 (d, J=18.51 Hz, 1P), −10.94 (d, J=18.39 Hz, 1P), −21.51 (d, J=17.18 Hz, 1P).

Step B—Synthesis of Compound 23

Into a 10-mL round-bottom flask, was placed a solution of compound 22 (5.46 mg, 0.009 mmol) in water (2 mL), triethylammonium bicarbonate buffer (1M) was employed to adjust the pH to 7-8. To the solution dithiothreitol (41.6 mg, 0.27 mmol) was added. After the resulting solution was stirred overnight at room temperature, it was concentrated in vacuo. The crude product was purified by Prep-HPLC with the following conditions (1#-Pre-HPLC-011(Waters)): Column, Atlantis Prep OBD T3 Column, 19*150 mm, 5 um; mobile phase, water with 50 mM ammonium bicarbonate and acetonitrile (up to 95% in 2 min); Detector, UV 254 & 320 nm. This resulted in 3.5 mg (67%) of compound 23 as a white solid. LC-MS: (ES, m/z): 521.0[M+H]$^+$, H-NMR: (300 MHz, $D_2O$, ppm): δ7.99 (s, 1H), 7.70 (s, 1H), 5.49 (s, 1H), 4.02-4.23 (m, 4H), 1.04 (s, 3H), P-NMR: (121 MHz, $D_2O$, ppm): δ −10.75 (s, 1P), −11.29 (d, J=18.75 Hz, 1P), −22.91 (s, 1P)

The following compounds of the present invention were made using the methods described in the Example above and substituting the appropriate reactants and/or reagents.

| Compd # | Structure | Starting Material | LC-MS or MS (M − H) |
|---|---|---|---|
| 24 | 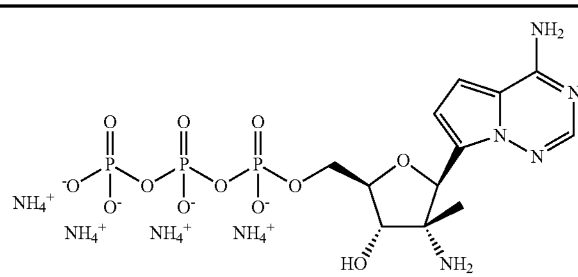 | Compound 2 | 514 |

-continued
| Compd # | Structure | Starting Material | LC-MS or MS (M − H) |
|---|---|---|---|
| 25 | 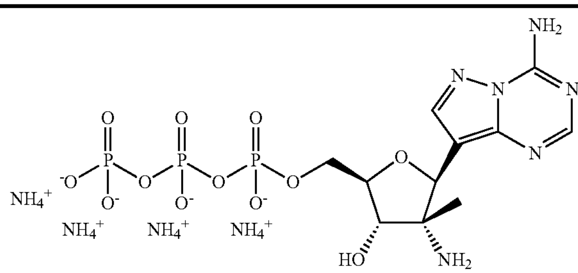 | Compound 4 | 515 |
| 1 | 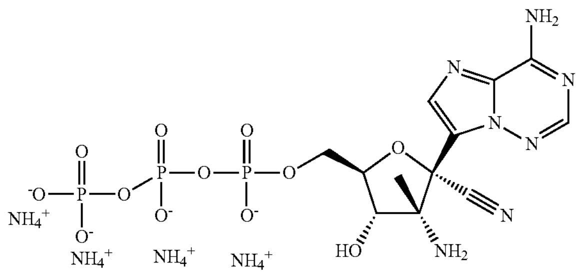 | Compound 5f | 540 |
Example 11
Preparation of Compound 4
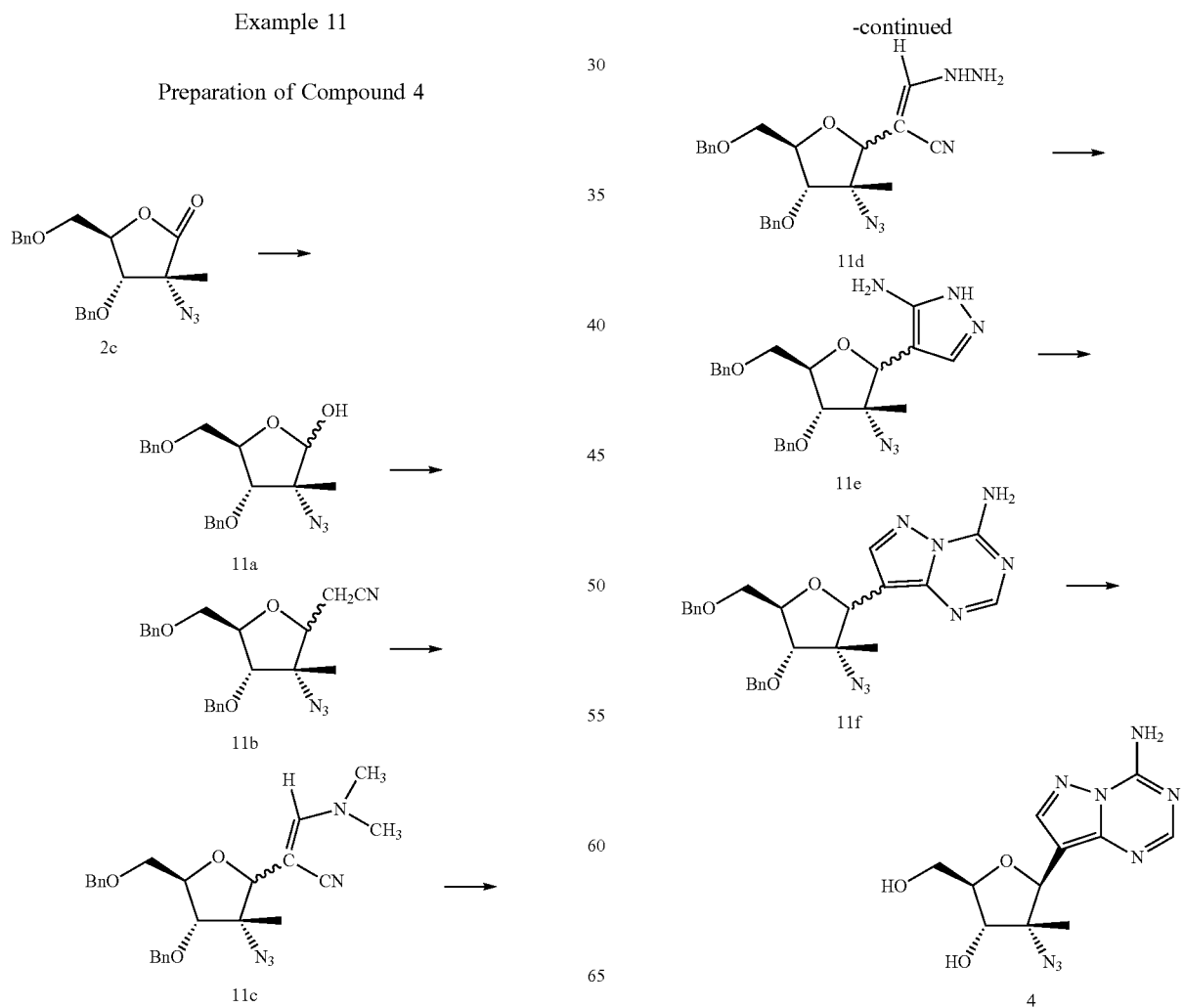

Step A—Synthesis of Compound 11a

Into a 50-mL round-bottom flask purged and maintained with an inert atmosphere of argon, was placed a solution of compound 2c (800 mg, 2.18 mmol) in THF (6 mL). This was followed by the addition of a solution of Li(t-BuO)$_3$AlH (890 mg, 3.50 mmol) in THF (8 mL) dropwise with stirring at −20° C. After the resulting solution was stirred for 30 minutes at −20° C. and another 3 hours at 30° C., the reaction mixture was cooled down with an ice/salt bath and quenched by the addition of acetic acid. The resulting solution was diluted with H$_2$O, extracted with ethyl acetate, dried over anhydrous sodium sulfate and concentrated in vacuo. The residue was applied onto a silica gel column and eluted with ethyl acetate/petroleum ether (1:25-1:4) to give 0.72 g (90%) of compound 11a as light yellow oil. LC-MS: (ES, m/z): 392.1 [M+Na]$^+$

Step B—Synthesis of Compound 11b

Into a 2000-mL round-bottom flask purged and maintained with an inert atmosphere of argon, was placed (EtO)$_2$OPCH$_2$CN (15.1 g, 85.24 mmol) and ethylene glycol dimethyl ether (250 mL). This was followed by the addition of sodium hydride (2.68 g, 67.00 mmol), in portions at 0° C. The resulting solution was stirred for 20 minutes at 0° C. To this was added a solution of compound 11a (17.5 g, 47.37 mmol) in ethylene glycol dimethyl ether (250 mL) dropwise with stirring at 0° C. in 30 minutes. After the resulting solution was stirred 2 hours at 30° C., the reaction mixture was cooled down to 0° C. and then quenched by the addition of acetic acid. The resulting solution was diluted with H$_2$O, extracted with ether, dried over sodium sulfate and concentrated in vacuo. The residue was applied onto a silica gel column and eluted with PE:EtOAc (20:1-5:1) to give 16.75 g (90%) of compound 11b as light yellow oil. LC-MS: (ES, m/z): 393.3 [M+H]$^+$

Step C—Synthesis of Compound 11c

Into a 150-mL round-bottom flask purged and maintained with an inert atmosphere of argon, was placed a solution of compound 11b (5.5 g, 14.01 mmol), t-BuOCH[N(CH$_3$)$_2$]$_2$ (9.8 g, 56.23 mmol), and Me$_2$NCHO (1.5 mL) in DCM (30 mL). After the resulting solution was stirred for 24 hours at 29° C., it was concentrated in vacuo. The residue was applied onto a silica gel column and eluted with ethyl acetate/petroleum ether (1:10-4:1) to give 4.7 g (75%) of compound 11c as light yellow oil. $^1$H-NMR-EBR0004-981-4 (mixture of two isomer): (400 MHz, CDCl$_3$, ppm): δ7.28-7.40 (m, 10H), 6.69 and 6.51 (s, 1H), 4.47-4.72 (m, 4H), 4.08-4.14 (m, 2H), 3.63-3.69 (m, 2H), 3.50 (m, dd, T=10.8 Hz, 2.8 Hz, 1H), 3.16 (s, 3H), 3.08 (s, 3H), 1.48, 1.46 (s, 3H)

Step D—Synthesis of Compound 11d

Into a 250-mL round-bottom flask purged and maintained with an inert atmosphere of argon, was placed a solution of compound 11c (4.5 g, 10.06 mmol), NH$_2$NH$_2$.H$_2$O (15.75 g, 252.00 mmol, 80%), and NH$_2$NH$_2$.HCl (11.25 g, 164.23 mmol) in methanol (120 mL). After the resulting solution was stirred for 24 hours at 75° C., the resulting mixture was concentrated in vacuo. The residue was dissolved in DCM, washed with H$_2$O, dried over sodium sulfate and concentrated in vacuo to give 4.2 g (crude) of compound 11d as light yellow oil, which was used for the next step without purification.

Step E—Synthesis of Compound 11e

Into a 25-mL round-bottom flask, was placed compound 11d (50 mg, 0.12 mmol) in acetonitrile (4 mL). After the resulting solution was stirred for 20 hours at 95° C., it was concentrated in vacuo. The residue was applied onto a silica gel column and eluted with dichloromethane/methanol (50:1-10:1) to give 36 mg (72%) of compound 11e as a light yellow solid. LC-MS (ES, m/z): 435.06 [M+H]$^+$

Step F—Synthesis of Compound 11f

Into a 25-mL round-bottom flask purged and maintained with an inert atmosphere of argon, was placed a solution of NCNHCHOCH$_3$ (33 mg, 0.39 mmol) in toluene (2 mL). This was followed by the addition of a solution of compound 11e (28 mg, 0.06 mmol) in toluene (3 mL) dropwise with stirring at 25° C. After the resulting solution was stirred for 4 hours at 95° C., it was concentrated in vacuo. The residue was applied onto a silica gel column and eluted with dichloromethane/methanol (50:1-10:1) to give 25 mg (80%) of compound 11f as a colorless solid. LC-MS (ES, m/z): 487.1 [M+H]$^+$

Step G—Synthesis of Compound 4

Into a 100-mL round-bottom flask purged and maintained with an inert atmosphere of argon, was placed a solution of compound 11f (1.35 g, 2.77 mmol) in DCM (15 mL). This was followed by the addition of BCl$_3$ (1M in DCM) (1.3 g, 11.09 mmol) dropwise with stirring at −78° C. in 5 minutes. After the resulting solution was stirred for 1 hour at −78° C. and an additional 1 hour at −50° C., the reaction was quenched by the addition of 2 mL of cold methanol. The pH value of the solution was adjusted to 7 with saturated sodium bicarbonate. The resulting mixture was concentrated in vacuo and the residue was purified by Prep-HPLC with the following conditions (1#-Pre-HPLC-011(Waters)): Column, Atlantis Prep OBD T$_3$ Column, 19*150 mm, 5 um; mobile phase, Water with 10 mmol NH$_4$HCO$_3$ and CH$_3$CN (1.0% CH$_3$CN up to 19.0% in 6 min, up to 95.0% in 1 min, down to 1.0% in 1 min); Detector, UV 254 & 220 nm. This resulted in 180 mg (21%) of compound 4 as a colorless solid. LC-MS: (ES, m/z): 307.10 [M+H]$^+$, $^1$H-NMR: (400 MHz, CD$_3$OD, ppm): δ8.18 (s, 1H), 8.07 (s, 1H), 5.15 (s, 1H), 4.21 (d, J=8.0 Hz, 1H), 3.91-3.99 (m, 2H), 3.81 (dd, J=12.0 Hz, 4.4 Hz, 1H), 1.17 (s, 3H).

Example 12

Cell-Based HCV Replicon Assay

To measure cell-based anti-HCV activity of selected compounds of the present invention, replicon cells were seeded at 5000 cells/well in 96-well collagen I-coated Nunc plates in the presence of the test compound. Various concentrations of test compound, typically in 10 serial 2-fold dilutions, were added to the assay mixture, with the starting concentration ranging from 250 μM to 1 μM. The final concentration of dimethylsulfoxide was 0.5% fetal bovine serum was 5%, in the assay media. Cells were harvested on day 3 by the addition of 1× cell lysis buffer (Ambion cat #8721).

The replicon RNA level was measured using real time PCR (Taqman assay). The amplicon was located in 5B. The PCR primers were: 5B.2F, ATGGACAGGCGCCCTGA (SEQ ID. NO. 1); 5B.2R, TTGATGGGCAGCTTGGTTTC (SEQ ID. NO. 2); the probe sequence was FAM-labeled CACGCCATGCGCTGCGG (SEQ ID. NO. 3). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 minutes, 95° C. for 10 minutes, 40 cycles of 95° C. for 15 sec, 60° C. for 1 minute. The ΔCT values ($CT_{5B}$-$CT_{GAPDH}$) were plotted against the concentration of test compound and fitted to the sigmoid dose-response model using XLfit4 (MDL). $EC_{50}$ was defined as the concentration of inhibitor necessary to achieve ΔCT=1 over the projected baseline; $EC_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from petroleum ether Applied Biosystems. Such an assay procedure was described in detail in e.g. Malcolm et al., *Antimicrobial Agents and Chemotherapy* 50: 1013-1020 (2006).

HCV replicon assay data was calculated for the compounds of the present invention using this method and replicon $EC_{50}$ data obtained is provided in the table below.

| Compound | 1b $EC_{50}$ (μM) |
| --- | --- |
| 2 | >100 |
| 3 | >100 |
| 4 | >100 |
| 5 | >100 |
| 6 | >100 |
| 7 | >100 |
| 8 | >100 |
| 9 | >100 |
| 10 | >100 |
| 11 | >100 |
| 12 | 16 |
| 13 | 1.3 |
| 14 | >100 |
| 15 | 28 |
| 16 | >100 |
| 17 | >100 |
| 18 | >100 |
| 19 | >100 |
| 20 | >100 |
| 21 | >100 |

The triphosphate forms or the compounds in the table would be expected to inhibit NS5B polymerase activity. The observed replicon activity can be impacted by different factors including efficiency of initial phosphorylation, the ability to enter the cell and processing of the prodrug.

Example 13

Inhibition of HCV NS5B Polymerase by Nucleoside Triphosphate Analogs

To measure inhibition of the enzymatic activity of the HCV NS5B RNA-dependent RNA polymerase by the nucleoside triphosphate compounds of the present invention, a radiolabeled nucleotide incorporation assay was used. This assay is a modified version of the assay described in International Publication No. WO2002/057287. Briefly, 50 μL reactions containing 20 mM HEPES (pH 7.3); 7.5 mM DTT; 20 units/ml RNasIN; 1 μM each of ATP, GTP, UTP and CTP; 20 μCi/mL [$^{33}$P]-CTP; 10 mM MgCl; 60 mM NaCl; 100 μg/ml BSA; 0.021 μM DCoH heteropolymer RNA template; and 5 nM NS5B (1b-BKΔ55) enzyme were incubated at room temperature for 1 hour. The assay was then terminated by the addition of 500 mM EDTA (50 μL). The reaction mixture was transferred to a Millipore DE81 filter plate and the incorporation of labeled CTP is determined using Packard TopCount. Compound $IC_{50}$ values can then be calculated from experiments with 10 serial 3-fold dilutions of the inhibitor in duplicate. The intrinsic potency (Ki) of an NTP inhibitor is derived from its NS5B $IC_{50}$ using the Cheng-Prusoff equation for a competitive inhibitor, as described in Cheng et al., *Biochem Pharmacol* 22:3099-3108 (1973): $Ki=IC_{50}/(1+[S]/K_m)$, where [S]=1 μM, and $K_m$ is the concentration of cognate NTP yielding half-maximal enzyme activity in the assay absent exogenous inhibitors.

Data was obtained using this method for the NTP analogs of selected compounds below of the present invention, and is set forth below.

| Compd # | Structure | $IC_{50}$ (μM) |
| --- | --- | --- |
| 22 | 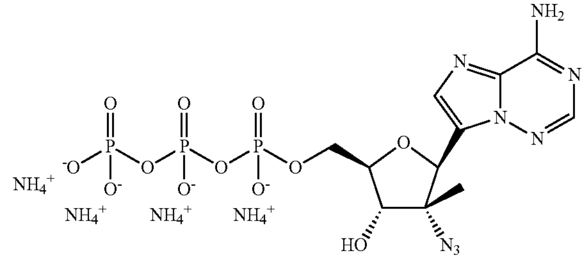 | 0.93 |

-continued

| Compd # | Structure | IC$_{50}$ (μM) |
|---|---|---|
| 23 | 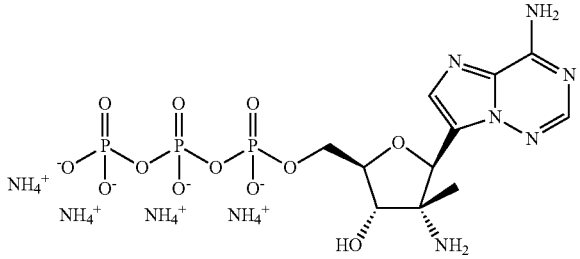 | 6.7 |
| 24 | 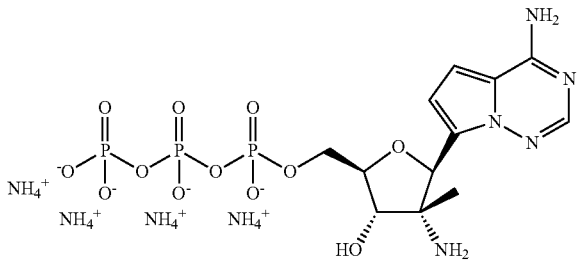 | 1.1 |
| 25 | 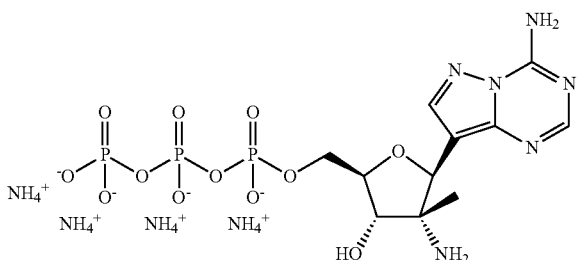 | 51 |

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

The invention claimed is:

1. A compound having the formula (I):

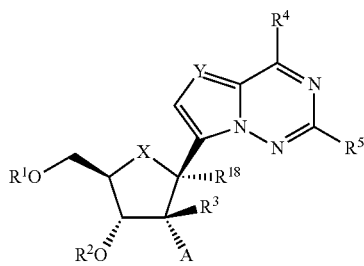

(I)

or a pharmaceutically acceptable salt thereof, wherein:

A is $-NH_2$;
X is O, N, S or $CH_2$;
Y is N or $-C(R^6)-$;
$R^1$ is H,

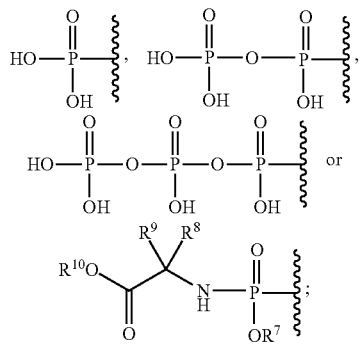

$R^2$ is H, $-C(O)-(C_1-C_6$ alkyl) or

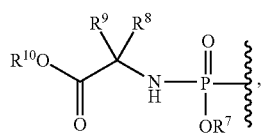

or $R^1$ and $R^2$ join to form a group having the formula:

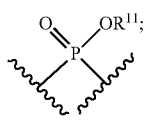

$R^3$ is $C_1-C_6$ alkyl, $C_1-C_6$ haloalkyl, $C_1-C_6$ hydroxyalkyl, $C_2-C_6$ alkenyl, $C_2-C_6$ alkynyl or $C_3-C_7$ cycloalkyl;

$R^4$ and $R^5$ are each independently selected from H, $-OR^{12}$, $-NHC(O)OR^{12}$, $-NHC(O)N(R^{12})_2$, $-N(R^{12})_2$ and $-NHC(O)R^{12}$;

$R^6$ is H, $C_1-C_6$ alkyl, $C_1-C_6$ haloalkyl, $C_1-C_6$ hydroxyalkyl, halo, $-OR^{12}$, $-SR^{12}$, $-N(R^{12})_2$, $C_3-C_7$ cycloalkyl, $C_6-C_{10}$ aryl, 5- or 6-membered monocyclic heteroaryl or 9- or 10-membered bicyclic heteroaryl;

$R^7$ is H, $C_6-C_{10}$ aryl, 5- or 6-membered monocyclic heteroaryl, 9- or 10-membered bicyclic heteroaryl, or $-(C_1-C_3$ alkylene)-$C(O)O-(C_1-C_6$ alkyl), wherein said $C_6-C_{10}$ aryl group, said 5- or 6-membered monocyclic heteroaryl group and said 9- or 10-membered bicyclic heteroaryl group can be optionally substituted with $R^{13}$, $R^8$ is H, $C_1-C_6$ alkyl, $C_3-C_7$ cycloalkyl, phenyl or benzyl, wherein said $C_1-C_6$ alkyl can be optionally substituted with a group selected from halo, $-OR^{12}$, $-SR^{12}$, guanidino, $-N(R^{12})_2$, $-C(O)OR^{12}$, $-C(O)N(R^{12})_2$, $-NHC(O)R^{12}$, 5- or 6-membered monocyclic heteroaryl and 9- or 10-membered bicyclic heteroaryl, and wherein said phenyl group and said benzyl group can be optionally substituted with up to 2 groups, each independently selected from $C_1-C_6$ alkyl, halo and $-OR^{12}$;

$R^9$ is H, $C_1-C_6$ alkyl, $C_3-C_7$ cycloalkyl, phenyl or benzyl, wherein said $C_1-C_6$ alkyl can be optionally substituted with a group selected from halo, $-OR^{12}$, $-SR^{12}$, guanidino, $-N(R^{12})_2$, $-C(O)OR^{12}$, $-C(O)N(R^{12})_2$, $-NHC(O)R^{12}$, 5- or 6-membered monocyclic heteroaryl and 9- or 10-membered bicyclic heteroaryl, and wherein said phenyl group and said benzyl group can be optionally substituted with up to 2 groups, each independently selected from $C_1-C_6$ alkyl, halo and $-OR^{12}$;

$R^{10}$ is H, $C_1-C_{20}$ alkyl, $C_2-C_{20}$ alkenyl, $-(C_1-C_3$ alkylene)$_m$-$(C_3-C_7$ cycloalkyl), $-(C_1-C_3$ alkylene)$_m$-$(C_6-C_{10}$ aryl) or $-(C_1-C_3$ alkylene)$_m$-adamantyl, wherein said $C_1-C_{20}$ alkyl group, said $C_2-C_{20}$ alkenyl group, said $C_6-C_{10}$ aryl group and said adamantyl group can be optionally substituted with up to three groups, each independently selected from halo, $-OR^{12}$, $-C(O)OR^{12}$, CN, $NO_2$, $C_1-C_6$ haloalkyl, $C_1-C_6$ hydroxyalkyl, $C_3-C_7$ cycloalkyl, $C_6-C_{10}$ aryl, 5- or 6-membered monocyclic heteroaryl, 9- or 10-membered bicyclic heteroaryl, $-N(R^{12})_2$, $-C(O)N(R^{12})_2$$-SR^{12}$, $-S(O)R^{12}$, $-S(O)_2R^{12}$, $-S(O)_2N(R^{12})_2$, $-NHC(O)R^{12}$, $-NHC(O)OR^{12}$ and $-NHC(O)N(R^{12})_2$;

$R^{11}$ is H, $C_1-C_{20}$ alkyl, $C_2-C_{20}$ alkenyl, $-(C_1-C_3$ alkylene)$_m$-$(C_3-C_7$ cycloalkyl), $C_3-C_7$ cycloalkyl, $-(C_1-$ $C_3$ alkylene)$_m$-$C_6$-$C_{10}$ aryl or —($C_1$-$C_3$ alkylene)$_m$-adamantyl, 5- or 6-membered monocyclic heteroaryl, 9- or 10-membered bicyclic heteroaryl, wherein said $C_1$-$C_{20}$ alkyl group, said $C_2$-$C_{20}$ alkenyl group, said $C_6$-$C_{10}$ aryl group, said adamantyl group, said 5- or 6-membered monocyclic heteroaryl group and said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5- or 6-membered monocyclic heteroaryl, 9- or 10-membered bicyclic heteroaryl, halo, —OR$^{12}$, —SR$^{12}$, —S(O)R$^{12}$, —S(O)$_2$R$^{12}$, —S(O)$_2$N(R$^{12}$)$_2$, $C_1$-$C_6$ haloalkyl, $C_1$-$C_6$ hydroxyalkyl, —O—($C_1$-$C_6$ haloalkyl), —CN, —NO$_2$, —N(R$^{12}$)$_2$, —C(O)OR$^{12}$, —C(O)N(R$^{12}$)$_2$ and —NHC(O)R$^{12}$, —NHC(O)OR$^{12}$ and —NHC(O)N(R$^{12}$)$_2$;

each occurrence of R$^{12}$ is independently H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl)$_m$-($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -5- or 6-membered monocyclic heteroaryl group or said 9- or 10-membered bicyclic heteroaryl group can be optionally substituted with R$^{16}$;

R$^{13}$ represents from one to five substituent groups, each independently selected from $C_1$-$C_6$ alkyl, halo, —OR$^{12}$, —SR$^{12}$, $C_1$-$C_6$ haloalkyl, $C_1$-$C_6$ hydroxyalkyl, —O—($C_1$-$C_6$ haloalkyl), —CN, —NO$_2$, —N(R$^{12}$)$_2$, —C(O)OR$^{12}$, —C(O)N(R$^{12}$)$_2$ and —NHC(O)R$^{12}$, or any two R$^{13}$ groups on adjacent ring carbon atoms can combine to form —O—R$^{14}$—O—;

R$^{14}$ is [C(R$^{15}$)$_2$]$_n$—;

each occurrence of e is independently H or $C_1$-$C_6$ alkyl;

R$^{16}$ represents from one to five substituent groups, each independently selected from $C_1$-$C_6$ alkyl, $C_2$-$C_6$ alkenyl, $C_2$-$C_6$ alkynyl, halo, —OR$^{17}$, —SR$^{17}$, $C_1$-$C_6$ haloalkyl, $C_1$-$C_6$ hydroxyalkyl, —O—($C_1$-$C_6$ haloalkyl), —CN, —NO$_2$, —N(R$^{17}$)$_2$, —C(O)OR$^{17}$, —C(O)N(R$^{17}$)$_2$ and —NHC(O)R$^{17}$;

each occurrence of R$^{17}$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl)$_m$-($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl);

R$^{18}$ is H, $C_1$-$C_6$ alkyl, —O($C_1$-$C_6$ alkyl), $C_1$-$C_6$ alkynyl, $C_1$-$C_6$ alkenyl, or CN; and each occurrence of m is independently 0 or 1, and each occurrence of n is independently 1, 2, or 3.

2. The compound of claim 1, wherein X is O.

3. The compound of claim 2, wherein R$^3$ is methyl.

4. The compound of claim 1 having the formula:

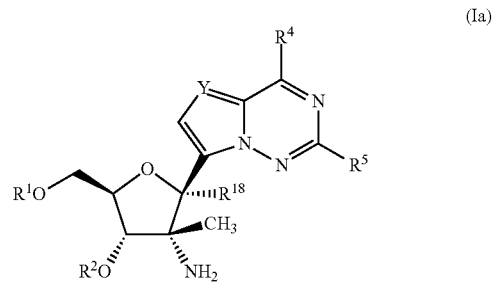

(Ia)

or a pharmaceutically acceptable salt thereof,
wherein:
R$^1$ is H,

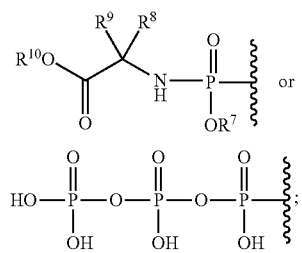

R$^2$ is H, or R$^1$ and R$^2$ join to form a group having the formula:

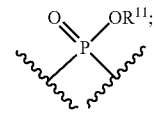

R$^4$ is H, OH or —N(R$^{12}$)$_2$;

R$^5$ is H or NH$_2$,

R$^{18}$ is H, —CN or —OCH$_3$;

R$^7$ is —($C_1$-$C_3$ alkylene)-C(O)O—($C_1$-$C_6$ alkyl) or phenyl, wherein said phenyl group can be optionally substituted with a halo group;

R$^8$ and R$^9$ are each independently H or $C_1$-$C_6$ alkyl;

R$^{10}$ is $C_1$-$C_6$ alkyl; and

R$^{11}$ is $C_1$-$C_6$ alkyl or $C_3$-$C_7$ cycloalkyl.

5. The compound of claim 4, wherein R$^1$ is:

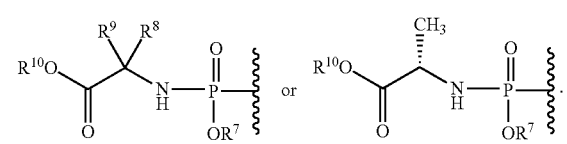

6. The compound of claim 4, wherein R$^1$ and R$^2$ join to form a group having the formula:

95
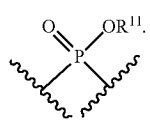
7. The compound of claim 5, wherein $R^1$ is:
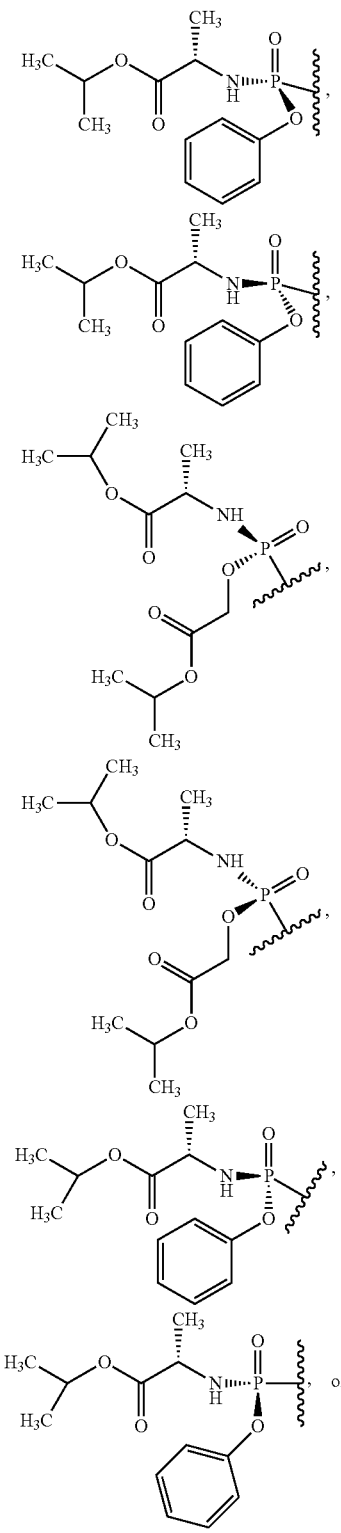
96
-continued
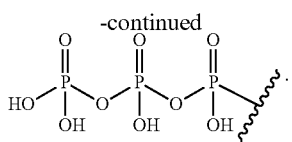
8. The compound of claim 6, wherein $R^1$ and $R^2$ join to form a group having the structure:
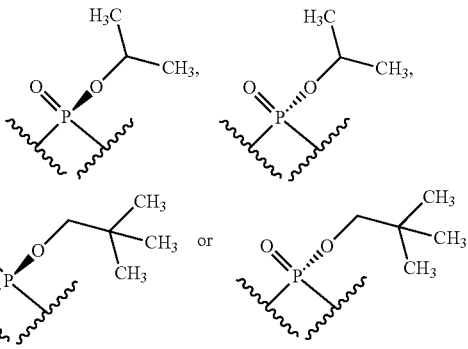
9. The compound of claim 4, wherein Y is N or CH, $R^4$ is $NH_2$ and $R^5$ is H.
10. The compound of claim 1 having the structure:
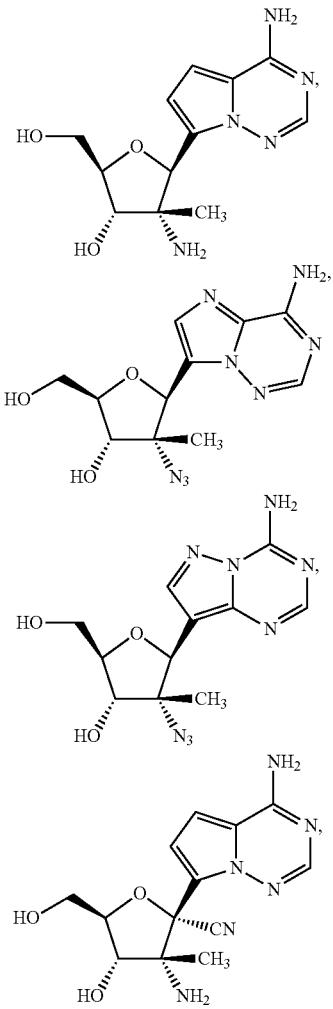

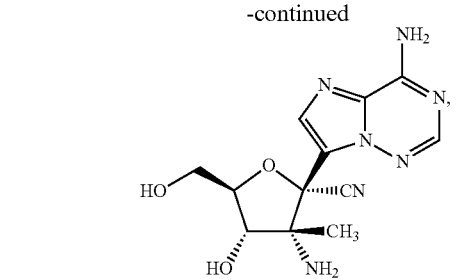
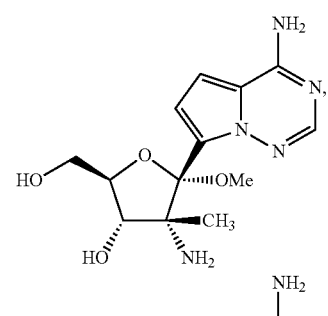
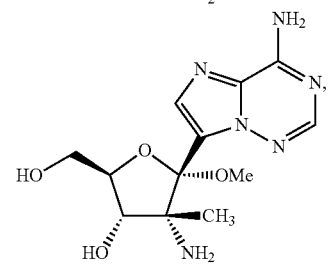
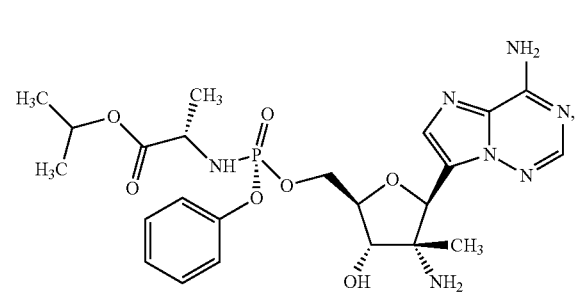
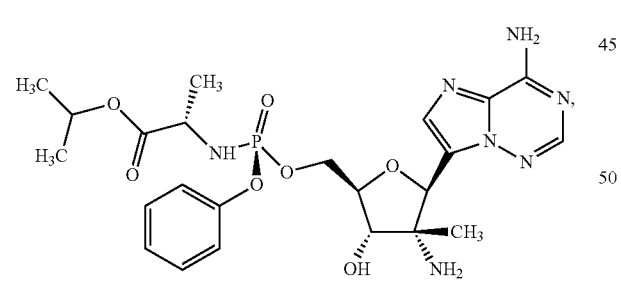
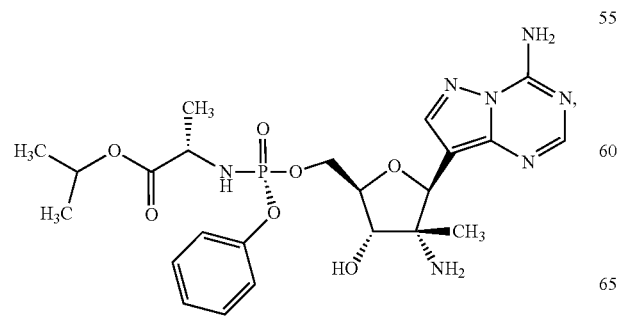
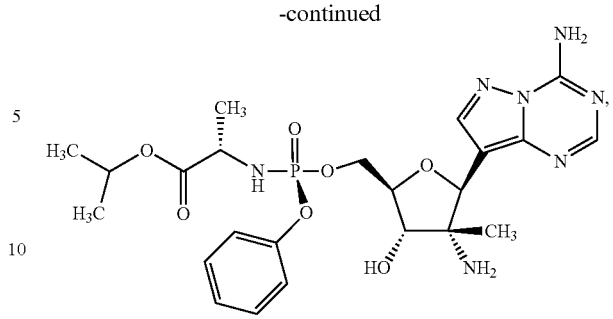
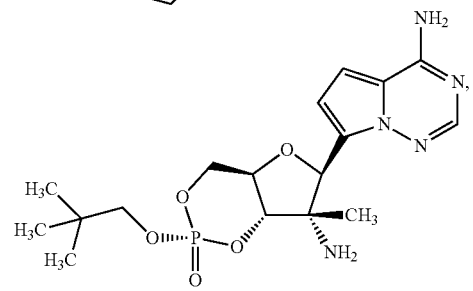
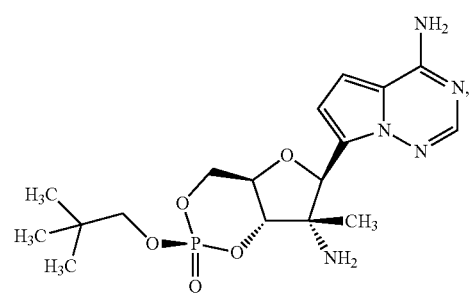
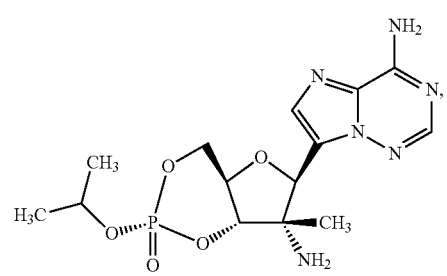
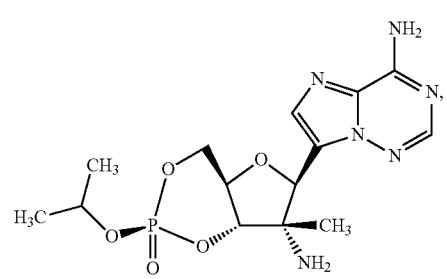
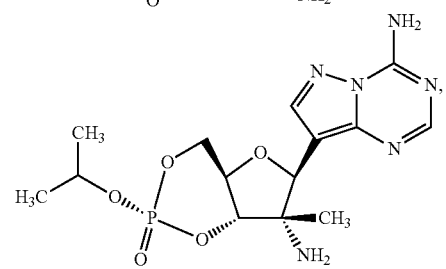

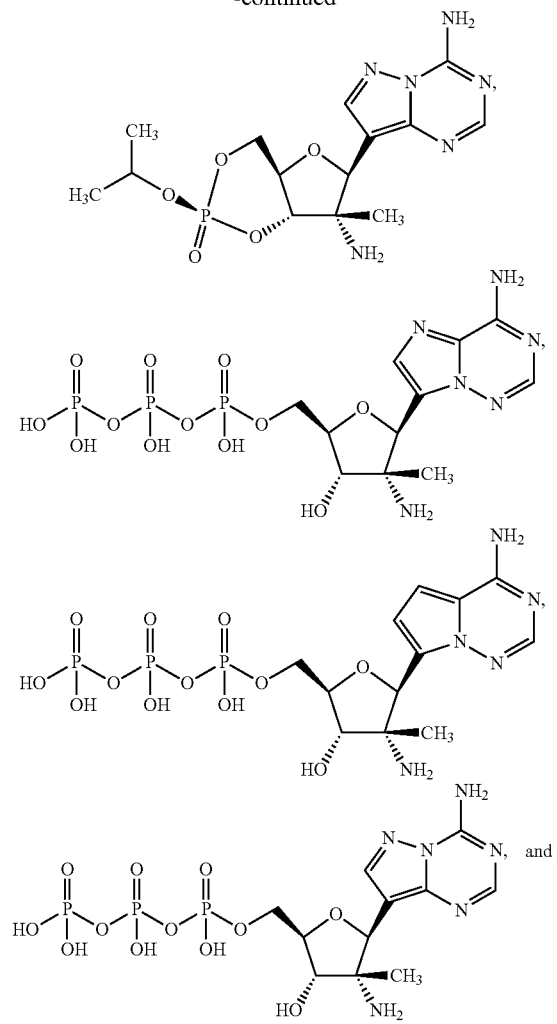

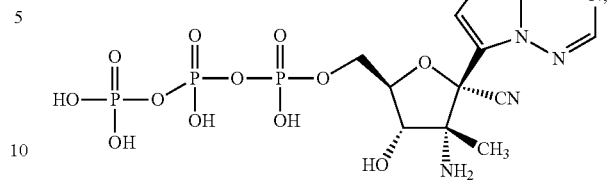

or a pharmaceutically acceptable salt thereof.

11. A pharmaceutical composition comprising an effective amount of the compound of claim 1 or a pharmaceutically acceptable salt thereof, and a pharmaceutically acceptable carrier.

12. The pharmaceutical composition according to claim 11, further comprising a second therapeutic agent selected from the group consisting of HCV antiviral agents, immunomodulators, and anti-infective agents.

13. The pharmaceutical composition according to claim 12, further comprising a third therapeutic agent selected from the group consisting of HCV protease inhibitors, HCV NS5A inhibitors and HCV NS5B polymerase inhibitors.

14. A method of treating a patient infected with HCV comprising the step of administering an amount of (i) the compound according to claim 1, or a pharmaceutically acceptable salt thereof, or (ii) a pharmaceutical composition comprising said compound and a pharmaceutically acceptable carrier effective to treat infection by HCV in said patient.

15. The method according to claim 14, further comprising the step of administering pegylated-interferon alpha and an HCV protease inhibitor to said patient.

16. The method according to claim 14 further comprising the step of administering ribavirin to said patient.

* * * * *